United States Patent
Liu et al.

(10) Patent No.: US 10,745,670 B2
(45) Date of Patent: Aug. 18, 2020

(54) IN VITRO PRODUCTION OF EXPANDED POTENTIAL STEM CELLS

(71) Applicant: GENOME RESEARCH LIMITED, Hinxton Cambridgeshire (GB)

(72) Inventors: Pentao Liu, Hinxton Cambridgeshire (GB); David Ryan, Hinxton Cambridgeshire (GB); Xuefei Gao, Hinxton Cambridgeshire (GB); Wei Wang, Hinxton Cambridgeshire (GB); Jian Yang, Hinxton Cambridgeshire (GB)

(73) Assignee: GENOME RESEARCH LIMITED, Hinxton, Cambridgeshire (GB)

( * ) Notice: Subject to any disclaimer, the term of this patent is extended or adjusted under 35 U.S.C. 154(b) by 0 days.

(21) Appl. No.: 15/527,269

(22) PCT Filed: Nov. 17, 2015

(86) PCT No.: PCT/EP2015/076871
§ 371 (c)(1),
(2) Date: May 16, 2017

(87) PCT Pub. No.: WO2016/079146
PCT Pub. Date: May 26, 2016

(65) Prior Publication Data
US 2018/0201904 A1   Jul. 19, 2018

(30) Foreign Application Priority Data

Nov. 17, 2014 (GB) .................................. 1420385.5
Aug. 5, 2015 (GB) .................................. 1513869.6

(51) Int. Cl.
| | |
|---|---|
| C12N 5/00 | (2006.01) |
| C12N 5/074 | (2010.01) |
| C12N 5/0735 | (2010.01) |
| A01K 67/027 | (2006.01) |
| C12N 5/073 | (2010.01) |

(52) U.S. Cl.
CPC ........ *C12N 5/0696* (2013.01); *A01K 67/0275* (2013.01); *C12N 5/0605* (2013.01); *C12N 5/0606* (2013.01); *A01K 2217/05* (2013.01); *C12N 2500/38* (2013.01); *C12N 2500/99* (2013.01); *C12N 2501/105* (2013.01); *C12N 2501/16* (2013.01); *C12N 2501/235* (2013.01); *C12N 2501/33* (2013.01); *C12N 2501/415* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2501/727* (2013.01); *C12N 2501/999* (2013.01); *C12N 2506/45* (2013.01)

(58) Field of Classification Search
CPC ............................ C12N 5/0696; C12N 5/0606
See application file for complete search history.

(56) References Cited

U.S. PATENT DOCUMENTS

2017/0275593 A1* 9/2017 Hanna .................. C12N 5/0606

FOREIGN PATENT DOCUMENTS

| WO | 2011019953 A1 | 2/2011 |
| WO | 2014174470 A1 | 10/2014 |

OTHER PUBLICATIONS

Klimanskaya et al. Nature 443:481-485, 2006 Corrections and Amendments, p. 512 (Year: 2006).*
Gafni, et al., "Derivation of novel human ground state naive pluripotent stem cells", Nature 504, 282-300 (2013).
Niakan, et al., "Derivation of extraembryonic endoderm stem (XEN) cells from mouse embryos and embryonic stem cells", Nat Protoc 8(6), 1028-1041 (2013).
Patent Cooperation Treaty, International Searching Authority, Search Report and Written Opinion for PCT/EP2015/076871, 13 pages, Feb. 22, 2016.
Takashima, et al., "Resetting Transcription Factor Control Circuitry toward Ground-State Pluripotency in Human", Cell 158, 1254-1269 (2014).
Theunissen, et al., "Systematic Identification of Culture Conditions for Induction and Maintenance of Naive Human Pluripotency", Cell Stem Cell 15, 1-17 (2014).

* cited by examiner

*Primary Examiner* — Marcia S Noble
(74) *Attorney, Agent, or Firm* — Leason Ellis LLP

(57) ABSTRACT

A culture medium is provided which is capable of establishing expanded potential stem cell (EPSC) lines which resemble naive or ground state ES cells, but are also able to differentiate into placenta trophoblasts and the embryo proper. Methods are provided using the medium for the in vitro conversion and maintenance of cells, including pluripotent cells into EPSCs.

7 Claims, 36 Drawing Sheets

FIG. 17A
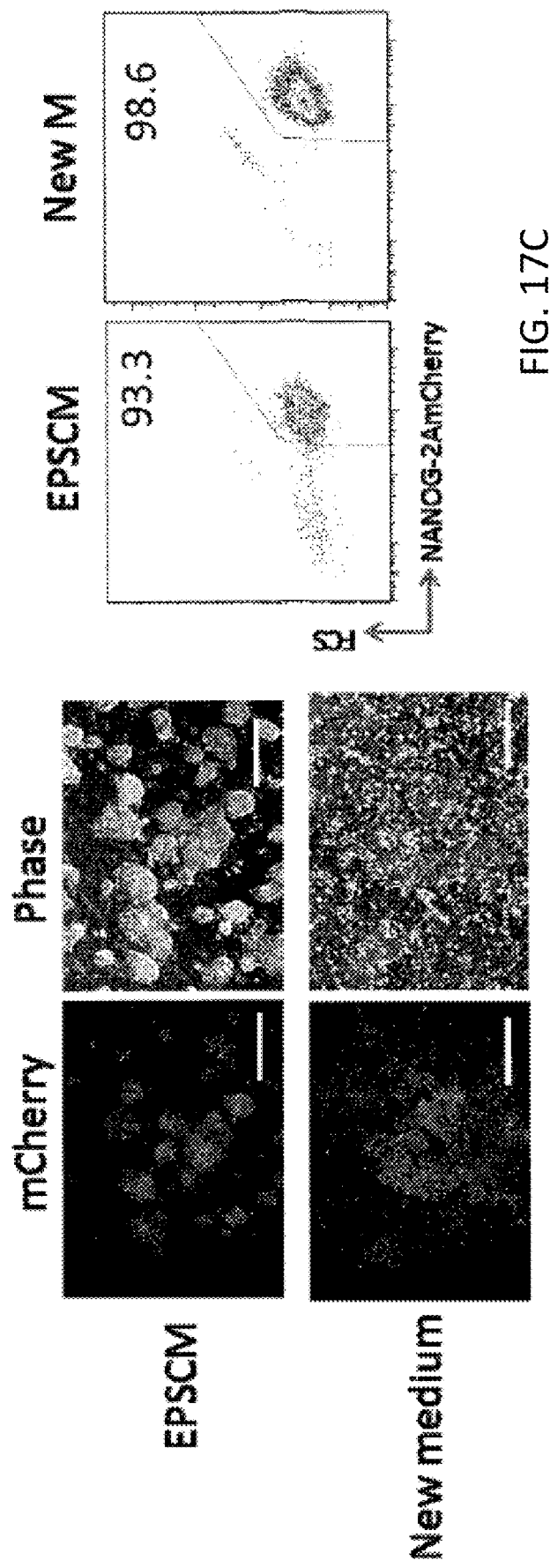
FIG. 17C
FIG. 17B

IN VITRO PRODUCTION OF EXPANDED POTENTIAL STEM CELLS

FIELD

This invention relates to the in vitro conversion of cells from mouse or human, or pluripotent cells into expanded potential stem cells (EPSCs), which have the ability to differentiate to cells of the embryo proper and extraembryonic tissues.

BACKGROUND

Mammalian embryonic development begins when a sperm and an egg fuse to form a zygote. The zygote undergoes a fixed number of divisions, generating cells known as blastomeres. Blastomeres of up to the 8 cells (8C) stage embryo have the capacity to differentiate to all lineages in the embryo proper and extraembryonic tissues and are considered totipotent (Ishiuchi et al 2013).

The 8C embryo undergoes compaction, and blastomeres acquire apicobasal polarity (Zernicka-Goetz 2005). Subsequent cell divisions produce two of the earliest lineages: the trophectoderm epithelium (TE) cells which are restricted to the trophoblast lineage and are essential for the formation of the placenta, and the inner cell mass (ICM) which are pluripotent and give rise to all cell types of the embryo proper, as well as to extra-embryonic endoderm and mesoderm (Gardner 1985, Rossant et al 2009, Yamanaka et al 2006).

Embryonic stem (ES) cells are derived from the inner cell mass (ICM). Although these cells are capable of differentiating into all germ cell layers of the embryo when returned to the blastocyst environment, they are generally unable to contribute to the trophoblast lineage.

Conversely, trophoblast stem cells, which are derived from the trophectoderm can efficiently differentiate into trophoblasts in vitro and in vivo. However, they are unable to differentiate into all germ cell layers of the embryo.

Currently, the only way to experimentally generate toti-potent-like or totipotent cells is through somatic cell nuclear transfer (SCNT), which involves injecting a somatic nucleus into an enucleated oocyte.

In mice, a recent report identified in standard ES cell culture a transitional subpopulation of cells that doesn't express pluripotency genes such as Pou5f1 (Oct4), Sox2 and Nanog, and are thought to correspond to the totipotent 2-cell stage (2C) blastomeres (Macfarlan et al 2012). Another study (Morgani et al 2013) found a specific cell population expressing Hhex in mouse ES cells cultured in 2i and LIF (2i/LIF), a defined condition that maintain the pluripotency network at an intrinsically stable ground state (Wray et al 2010, Ying et al 2008). These rare cells were shown to contribute to extra-embryonic lineages in chimera and to have features of 16-cell embryo or the morula (Morgani et al 2013).

Although human embryonic stem cells have also been reported to differentiate to trophoblasts in vitro under certain conditions, there is debate as to whether these in vitro differentiated trophoblasts are bona fide trophoblasts (see, Roberts R M et al 2014)

When cultured in vitro, human embryonic stem cells show distinct molecular and biological characteristics compared to the paradigmatic embryonic stem cells from mouse. The terminology 'naïve' (or 'ground state') and 'primed' was introduced to describe the observed differences, with mouse ESCs being 'naïve' and resembling the early epiblast, while human ESCs are 'primed' and resemble the later developmental stage of the egg cylinder or embryonic disc (Nichols and Smith, 2009).

Recently, several researchers have reported alternative conditions for inducing a more 'naïve' pluripotent state in conventional human embryonic stem cells, for example, by culturing in a cocktail of inhibitors (summarised in Theunissen et al 2014). However, although cells produced by these methods display some characteristics which are comparable to naive cells, there are also significant differences. For example, Theunissen et al 2014, who use a six inhibitor+ LIF+activin (6i/L/A) cocktail to reset pluripotent stem cells to a more naïve state still report X chromosome inactivation. This is in contrast to the naïve cell state where both X chromosomes are active. Takashima et al 2014 also report differences in epigenetic markers in 6i/L/A-cultured cells, and instead propose that a more naïve or ground state may be instated in human pluripotent stem cells following short term expression of NANOG and KLF2 transgenes.

Despite these findings, it remains unclear whether it is possible to experimentally generate and maintain mammalian cells that have features of cleavage blastomeres and the potential to contribute to both the embryonic lineages and trophoblasts.

SUMMARY

The present inventors have developed a culture medium capable of establishing expanded potential stem cell (EPSC) lines which resemble naïve or ground state ES cells, but are also able to differentiate into placenta trophoblasts and the embryo proper.

The present culture medium, termed Expanded Potential Stem Cell Media (EPSCM), is capable of establishing stable and homogeneous cultures of EPSC lines from mammalian embryonic stem (ES) and induced pluripotent stem (iPS) cells, directly from in vitro cultured preimplantation embryos or individual blastomeres, or by reprogramming somatic cells. The EPSCM is effective to generate EPSCs from various mammalian species including the paradigmatic mouse and also humans.

Our EPSCM appears to act by stabilising the cells cultured in the medium into a state comparable to a 4C blastomeres (our data show that the EPSCs generated using our medium have molecular and functional features of 4C blastomeres). This is a state which is otherwise transient, difficult to capture, culture or manipulate. Therefore, these cells likely serve as better donors in non-human animal cloning, and better stem cells in producing non-human transgenic animals. Significantly, our EPSC cultures are homogenous and stable, rather than rare and transient as has previously been observed. EPSCs are converted from pluripotent stem cells without the use of transgenes and self-renew in vitro when cultured in EPSCM. The resulting EPSC lines are transgene-independent. EPSCs resemble naïve or ground state ES cells, for example, female EPSCs show X chromosome reactivation EPSCs can be distinguished from standard mammalian ES cells by distinct molecular features described herein.

EPSCs will be valuable for studying early embryonic cell plasticity, for exploring distinct pluripotent states which may be conserved across multiple mammalian species and are thus easier to be captured or maintained in vitro, and for expanding the utility of stem cells in therapies. EPSCs will be useful in research and R&D as well as medicine and agriculture (for example reproduction and cloning of non-human animals). In particular human EPSCs hold great promise for regenerative medicine.

Aspects of the Invention

An aspect of the invention provides a method for producing a population of expanded potential stem cells (EPSCs) which comprises:
(i) Providing a population of pluripotent cells,
(ii) Culturing the population in an expanded potential stem cell medium (EPSCM), wherein the EPSCM comprises one or more of:
a RAS-ERK inhibitor,
a Src Kinase family (SFK) inhibitor,
a GSK3 inhibitor,
a Wnt inhibitor or Axin stabilizer,
and optionally LIF, IGF-II or Activin or its functional equivalent, to produce a population of EPSCs. In some aspects the EPSCM may further comprise one or more of a Jun N-Terminal Kinase (JNK) inhibitor, and/or a p38 inhibitor.

An aspect of the invention provides a method for producing a population of expanded potential stem cells (EPSCs) which comprises:
(i) Providing a population of pluripotent cells,
(ii) Culturing the population in an expanded potential stem cell medium (EPSCM), wherein the EPSCM comprises one or more of:
a RAS-ERK inhibitor,
a Src Kinase family (SFK) inhibitor,
a GSK3 inhibitor,
a Wnt inhibitor,
a p38 inhibitor,
a JNK inhibitor to produce a population of EPSCs.

Another aspect of the invention provides an expanded potential stem cell culture medium (EPSCM) comprising a basal cell nutrient medium and one or more of:
a RAS-ERK inhibitor,
a Src Kinase family (SFK) inhibitor,
a GSK3 inhibitor,
a Wnt inhibitor,
and optionally LIF, IGF-II or Activin or its functional equivalent. In some aspects the EPSCM may further comprise one or more of a Jun N-Terminal Kinase (JNK) inhibitor, and/or a p38 inhibitor.

Another aspect of the invention provides an expanded potential stem cell culture medium (EPSCM) comprising a basal cell nutrient medium and one or more of:
a RAS-ERK inhibitor,
a Src Kinase family (SFK) inhibitor,
a GSK3 inhibitor,
a Wnt inhibitor,
a p38 inhibitor, and a Jun N-Terminal Kinase (JNK) inhibitor.

The medium may comprise any two, three, four, five or all inhibitors selected from:
a RAS-ERK inhibitor,
a Jun N-Terminal Kinase (JNK) inhibitor,
a p38 inhibitor,
a Src Kinase family (SFK) inhibitor,
a GSK3 inhibitor, and
a Wnt inhibitor.

The medium may comprise all six inhibitors set out above.

The medium may comprise any two or three out of the following four inhibitors
a RAS-ERK inhibitor,
a Src Kinase family (SFK) inhibitor,
a GSK3 inhibitor, and
a Wnt inhibitor.

The medium may further comprise a well defined basal medium, such as Albumax or N2B27.

The EPSCs produced may be mammalian, preferably human.

The EPSCs may be used in a method of generating a transgenic non-human animal.

The animal may be a mouse, rat, pig, cow or any other non-human animal described herein.

A method of making a transgenic non-human animal may comprise the steps of: generating a population of EPSCs, optionally genetically manipulating the EPSCs, for example by genome editing such as CRISPR/CAS9; injecting the generated EPSCs into a blastocyst to generate a chimera and culturing the blastocyst under conditions suitable to develop into a non-human animal.

The invention also provides an isolated population of EPSCs produced by a method described herein and a population of isolated EPSCs for use in a method of treatment of the human or animal body.

The population of EPSCs may be cultured or maintained in the EPSCM.

The invention further provides an EPSC maintenance medium for culturing or maintaining converted EPSCs, comprising one or more of a Ras-ERK inhibitor, a Src Kinase family (SFK) inhibitor a GSK3 inhibitor, and a Wnt inhibitor. The medium may further comprise one or more of a Jun N-Terminal Kinase (JNK) inhibitor, a p38 inhibitor. The medium may optionally comprise one or more of a notch modulator, an integrin modulator, and a Hippo modulator.

Other aspects of the invention are described herein.

BRIEF DESCRIPTION OF FIGURES

FIG. 1A: ES cell (E14) colonies in gelatinized 6-well dishes (Top panels. Scale bar 50 μM), or grown on SNL feeders (bottom panels. Scale bar 100 μM). Expression of pluripotency genes FIG. 1B or lineage differentiation genes FIG. 1C in ESCs cultured in EPSCM. Relative expression of these genes is normalized to Gadph. Data are mean±s.d. FIG. 1D: Rapid up-regulation of trophoblast transcription factor genes Cdx2 and Eomes in EPSCs cultured in TS cell medium. Only meso-endoderm markers (T and Gata6) increased in ESCs (2i/LIF or M15). Expression was normalized to un-differentiated ESCs/EPSCs in M15, 2i/LIF or EPSCM, respectively. Data are mean±s.d. Experiments were repeated three times. FIG. 1E: Contribution of EPSCs to both the ICM and the trophectoderm in vivo. EPSCs cultured in 2i/LIF gradually lose the capacity to contribute to the TE.

FIG. 2A: Development of 8-cell mouse embryos in EPSCM or in M15 (scale bar=50 μm). FIG. 2B Immunofluorescence detection of Oct4 and Cdx2 in embryos cultured in EPSCM. (scale bar=25 μm and 100 μm for the late outgrowths). Oct4+ small cells emerged from the edge of the "filled" blastocysts. In the outgrowths, many cells initially expressed Cdx2 but subsequently all cells became uniformly Oct4+ and Cdx2-. FIG. 2C: Derivation of EPSC lines from single blastomeres. Single 8C blastomeres were seeded in individual wells of a 96-well plate on feeders in EPSCM. Temporal progression of the blastomere was imaged (scale bar=50 μm). P1: passage 1 of a primary outgrowth. FIG. 2D: Expression of Oct4 and Cdx2 in the primary outgrowth from a single blastomere (scale bar=100 μm). Most cells were Oct4$^+$ and Cdx2$^-$. FIG. 2E: Efficiency of derivation of stable EPSC lines from single blastomeres. FIG. 2F: Contribution of EPSCs (mCherry$^+$) derived from pre-implantation embryos or iPSCs to both the ICM and the TE in the blastocysts.

FIG. 4A: Unsupervised hierarchical clustering of the population transcriptomes. Mouse ES lines derived in 2i/LIF media (DR4 and DR9) or EPSC lines derived in EPSCM media (DR25 and DR10) were cultured in M15, 2i/LIF and EPSCM, respectively. The heatmap represents the inter-sample correlation coefficient calculated by Spearman rank correlation method. Clustering was done by complete linkage and genes with maximum expression less than 5 normalized counts were removed. FIG. 4B: PCA of the single-cell transcriptomes of EPSCs, or ESCs (M15 and 2i/LIF) was plotted in 3D spaces defined by the first three principal components. FIG. 4C: Volcano plot of the differential gene analysis result between EPSCs and 2i/LIF ESCs. Genes significantly up-regulated in EPSCs and 2i/LIF ESCs were labelled in purple and green, respectively. Key pluripotency factors were marked in red. FIG. 4D: Boxplots comparing the expression of pluripotency factors in EPSCs or in ESCs. The expression of these genes shows higher fluctuation in M15 ESCs than in 2i/LIF ESCs or in EPSCs. The bar and diamond in the box mark the median and mean of each group. FIG. 4E: Comparison of expression variability of pluripotency genes in EPSCs and ESCs. The variability is compared by the ratio of the coefficient of variation (CV) of these genes compared to that of 2i/LIF ESCs. FIG. 4F: Boxplots comparing the global transcriptome variability of EPSCs and ES cells. The variability is quantified by the $\log_{10}$ (squared coefficient of variation) of individual genes in these cells. The bar and diamond in the box mark the median and mean of each group. Wilcoxon rank sum test with continuity correction * $p<0.001$, NS: $p>0.05$. FIG. 4G: Three-dimensional scatter plot showing the relationship of pre-implantation embryos, 2i/LIF ESCs and EPSCs in the space defined by the first three principal components. FIG. 4H: Bar chart showing the normalized enrichment scores of EPSCs and 2i/LIF ES cells in the expression of embryonic stage-specific gene sets. nominal p value <0.01. The normalized count matrix of the single-cell EPSC and 2i/LIF ES cell dataset are used as input matrix. The definition of stage-specific gene set is described in Method. FIG. 4I: PCA of EPSCs and the ES cells or iPS cells reported to have totipotent-like features. Only protein coding genes are included in this analysis. Transcriptomes used: 2i/LIF ES cells: DR4 and DR9; EPSCs: DR10 and DR25; M15: DR10 and DR25 cultured in M15

FIG. 5A: FACS analysis of mCherry$^+$ placenta cells. FIG. 5B: Expression of trophoblast genes in sorted mCherry$^+$ placenta cells from an EPSC chimera. Expression was normalized to fetal brain. mCherry$^-$ placenta cells were used as the control. Data are mean±s.d. FIG. 5C: Detection of polyploidy placenta cells. A distinct population of 8N cells was found in mCherry$^+$ placental cells in EPSC chimeras FIG. 5D.

FIG. 6B shows the primary human iPSC colonies after switching to EPSCM. FIG. 6C shows stable human EPSC (h-EPSC) lines established in EPSCM.

(FIG. 10D)

RNA-seq data from standard H1 was downloaded from ENCODE project. Significantly differentially expressed genes (p<0.05,|log 2 fold change|>1) include key pluripotency genes such as NANOG, TBX3, DPPA3, and KLF4.

Figure 15:
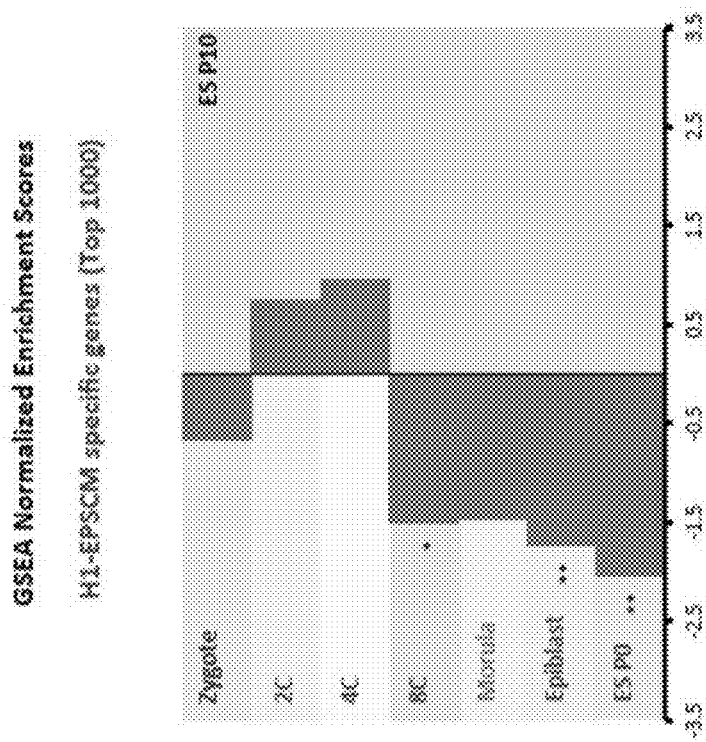

FIG. 15 shows that EPSC-specific gene set enrichment is different in pre-implantation stages of human embryos. The top 1000 genes that were up-regulated in EPSCs compared to H1 cells were used as an EPSC-specific gene set and the expression was compared between P10 hESC and different embryonic stages from Yan et al. Differential genes were tested by Cuffdiff2 between EPSCs. Nominal p-value **=<0.01, *=0.05.

Figure 16B:
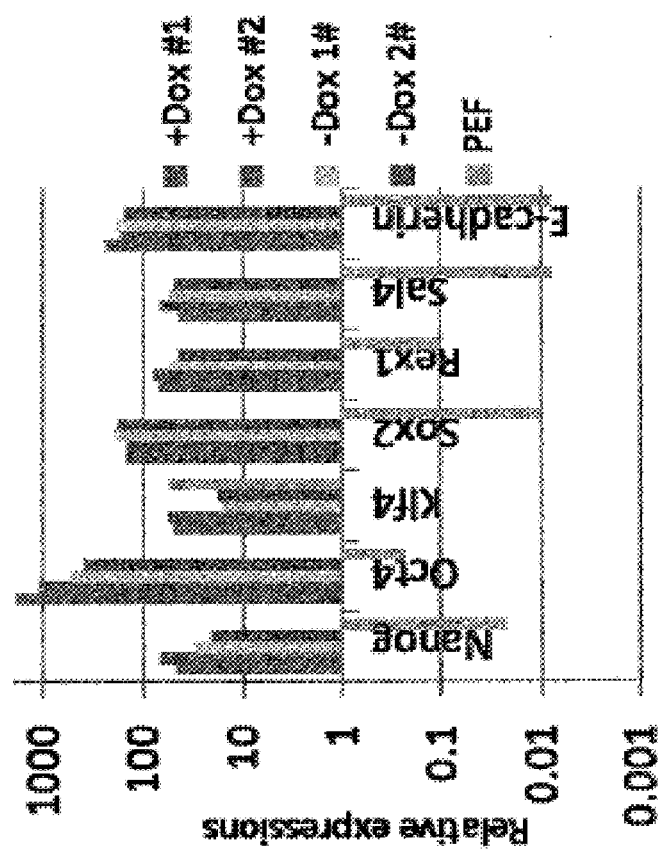
Figure 16A:
Figure 16C:
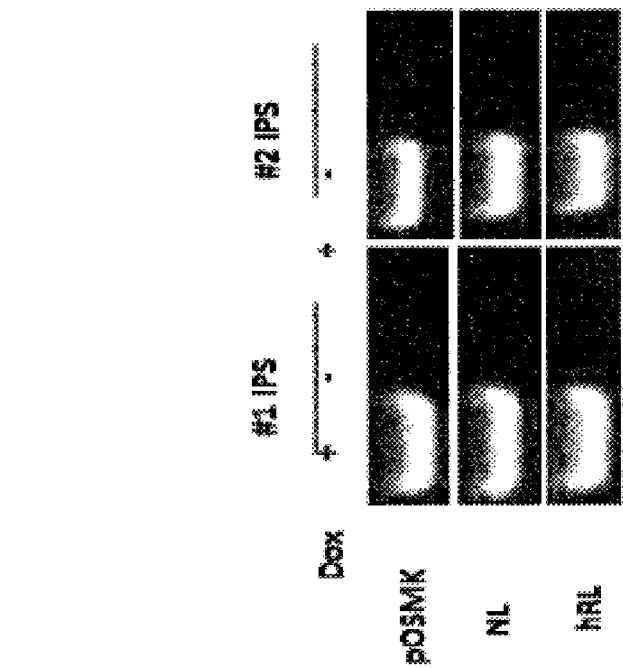
Figure 16D:
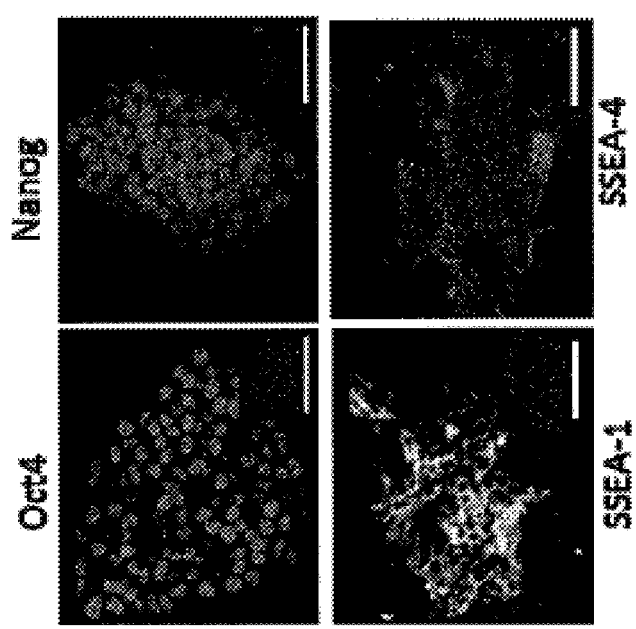

FIGS. 16A-16D show that the EPSCM maintains porcine iPSCs (piPSCs) without leaky expression of exogenous factors or transgene-independent. FIG. 16A: A representative piPSC colony growing in Dox free medium on STO feeder cells. These iPSCs were produced by expressing eight reprogramming factors (Oct4 (pig), Sox2 (pig), Klf4 (pig), cMyc (pig), Nanog (pig), RARG (human), LRH1 (human), LIN28 (Human), Dox-inducible. FIG. 16B: qRT-PCR analysis of expression of selected pluripotency genes in piPSC cultured in the Dox or Dox-free condition. The expression levels were normalised to one thousandth of GAPDH expression. FIG. 16C: RT-PCR analysis to detect expression of exogenous reprogramming factors in piPSC with or without Dox. No detectable leaky expression of exogenous reprogramming factors was found. OSMK: Oct4, Sox2, Klf4 and c-Myc; NL: Nanog and LIN28; hRL: RARG and LIN28. FIG. 16D: Immunofluorescence staining of pluripotency markers in piPSCs: OCT4, NANOG, and surface marker SSEA-1and SSEA4. Nuclei were stained with DAPI (blue). Scale bar: 50 μm.

FIGS. 17A-17C shows that the EPSCM maintains human EPSCs. FIG. 17A: The human EPSCs are NANOG-mCherry reporter cells where the mCherry cassette is targeted to the human NANOG locus. FIG. 17B: Maintenance of the reporter cells under the standard EPSCM condition or the new medium. Scale bar: 200 μm. FIG. 17C: Flow cytometry analysis of NANOG expression in the reporter cells cultured under the standard EPSCM condition or the new medium.

DETAILED DESCRIPTION

This invention relates to the production of expanded potential stem cells (EPSCs) from populations of pluripotent cells. EPSCs have 'naïve' or ground state properties and have an expanded potential to differentiate into extraembryonic cell lines (trophoblasts and extraembryonic endoderm in the yolk sac) as well as cells of the embryo proper which are derived from the inner cell mass of the blastocyst.

EPSCs may be consistently produced from different pluripotent cell lines which are cultured in expanded potential stem cell media (EPSCM). EPSCs have been successfully differentiated into a range of cell types including pancreatic cells, neurons and T-cells as described herein.

EPSCs may be useful for studying the mechanisms of development and EPSCs or cells differentiated therefrom are expected to have applications in medicine, particularly regenerative medicine. EPSCs are expected to have utility in research and R&D, for example in disease modelling, screening for therapeutics, testing toxicity, studying genetic diseases and studying reproductive biology. EPSCs are also expected to have utility in non-human animal reproduction and cloning and therapeutic human reproduction and cloning (for example cloning of human cells or tissues). EPSCs have much higher gene targeting efficiency compared to ESCs and also allow for more efficient generation of transgenic (non-human) animals. EPSCs can therefore be used in methods of generating transgenic non-human animals. One utility of EPSCs of non-human animals is cloning, or somatic cell nuclear transfer (SCNT). For example, EPSCs which are genetically modified or have undergone genome editing can be used as donors for SCNT.

A method of making a transgenic non-human animal may comprise generating a population of EPSCs, optionally genetically manipulating the EPSCs, for example by genome editing techniques. Methods for genetically manipulating cells are well-known and include CRISPR/CAS9. The method may further comprise injecting the generated EPSCs into a blastocyst to generate a chimera and then culturing the blastocyst under conditions suitable to develop into a non-human animal.

A population of expanded potential stem cells (EPSCs) may be produced as described herein by culturing a population of pluripotent cells (PSCs) in an expanded potential stem cell medium (EPSCM) to produce a population of EPSCs.

Pluripotent cells are cells which exhibit an undifferentiated phenotype and are potentially capable of differentiating into any foetal or adult cell type of any of the three germ layers (endoderm, mesoderm and endoderm). A pluripotent cell is distinct from a totipotent cell and generally cannot give rise to extraembryonic cell lineages. The population of pluripotent cells may be clonal i.e. genetically identical cells descended from a single common ancestor cell.

Preferably, the pluripotent cells are human pluripotent cells (hPSCs).

Pluripotent cells may include embryonic stem cells (ESCs) and non-embryonic stem cells, for example foetal and adult stem cells, and induced pluripotent stem cells (iPSCs). In some embodiments, the pluripotent cells are not hESCs. In some embodiments the pluripotent stem cells are not 'primed' pluripotent stem cells, such as epiblast stem cells (EpiSCs).

Embryonic stem cells may be obtained using conventional techniques. For example, ESCs cells may be obtained from a cultured ESC cell line, for example a hESC line. Numerous cultured hESC lines are publically available from repositories (e.g. NIH Human Embryonic Stem Cell Registry), such as CHB-1 to CHB-12, RUES1 to RUES3, HUES1 to HUES28, HUES45, HUES48, HUES49, HUES53, HUES62 to HUES66, WA01 (H1), WA07 (H7), WA09 (H9), WA13 (H13), WA14 (H14), NYUES1 to NYUES7, MFS5, and UCLA1 to UCLA3. Further examples of suitable human embryonic stem cell lines are described in Thomson J A et al Science 282: 1145-1147 (1998); Reubinoff et al. Nat Biotechnol 18:399-404 (2000); Cowan, C. A. et al. N. Engl. J. Med. 350, 1353-1356(2004), Gage, F. H., et al. Ann. Rev. Neurosci. 18 159-192 (1995); and Gotlieb (2002) Annu. Rev. Neurosci 25 381-407); Carpenter et al. Stem Cells. 5(1): 79-88 (2003). Potentially clinical grade hESCs are described in Klimanskaya, I. et al. Lancet 365, 1636-1641 (2005) and Ludwig, T. E. et al. Nat. Biotechnol. 24, 185-187 (2006). Suitable hESCs may be obtained for use in the invention without either destroying a human embryo or using a human embryo for an industrial or commercial purpose. For example, hESCs may be obtained by blastomere biopsy techniques (Klimanskaya (2013) Semin Reprod Med. 31(1):49-55; Cheung et al 2008, Klimanskaya et al Nature (2006) 444(7118)481-5).

iPSCs are pluripotent cells which are derived from non-pluripotent, differentiated ancestor or antecedent cells. Suitable ancestor cells include somatic cells, such as adult fibroblasts and peripheral blood cells. Ancestor cells are typically reprogrammed by the introduction of pluripotency genes (or RNA encoding them) or their corresponding proteins into the cell, or by re-activating the endogenous pluripotency genes. The genes, RNA encoding them, or proteins may be introduced into the differentiated cells by any suitable technique, including plasmid or more preferably, viral transfection or direct protein delivery. Pluripotency genes include members of the Oct family, such as Oct or Sox family 4 (also known as oct3/4), Sox2 and Sox1. Other genes, for example Klf genes, such as Klf-1, -2, -3, -4 and -5; Myc genes such as C-myc, L-myc and N-myc; nanog; Lrh genes such as Lhr1, and Rar genes such as Rara or rar-g and Lin28 may also be introduced into the cell to increase induction efficiency. Following introduction of the pluripotency genes or proteins, the ancestor cells may be cultured. Cells expressing pluripotency markers may be isolated and/or purified to produce a population of iPSCs. Techniques for the production of iPSCs are well-known in the art (Yamanaka et al Nature 2007; 448:313-7; Yamanaka 6 2007 Jun. 7; 1(1):39-49; Kim et al Nature. 2008 Jul. 31; 454(7204):646-50; Takahashi Cell. 2007 Nov. 30; 131(5): 861-72. Park et al Nature. 2008 Jan. 10; 451(7175):141-6; Kimet et al Cell Stem Cell. 2009 Jun. 5; 4(6):472-6; Vallier, L., et al. Stem Cells, 2009. 9999(999A), Wang W, et al. PNAS. (2011) 108; 45; 18283-8.

Thus, a population of pluripotent stem cells may be obtained by reprogramming non-pluripotent cells, such as somatic cells into induced pluripotent stem cells (iPSCs) by introducing pluripotency genes or their corresponding proteins, or by reactivating the endogenous pluripotency genes, using techniques which are known in the art and discussed herein.

The pluripotency genes or proteins may comprise one, two, three, four, five or six of an OCT family member, KLF family member, MYC family member, LRH family member, RAR family member.

The OCT family member may be Oct4.

The Klf family member may be klf1, klf2, klf 4 or klf 5. Preferably klf 4. Each of these related family members have been shown to be capable of generating iPS cells.

The myc family member may be c-myc, n-myc or L-myc or NANOG. Preferably c-myc or nanog. Each of these related family members have been shown to be capable of generating iPS cells. However, several authors have also reported that c-myc is not necessary for the generation of iPS cells. Therefore, in some embodiments the pluripotency genes or proteins do not include c-myc.

The Lrh family member may be LRH1.

The Rar family member may be Rar-a or Rar-g. Each of these related family members have been shown to be capable of generating iPS cells.

In one embodiment, pluripotency genes or proteins may comprise oct4, sox2, Klf4 and cmyc (Yamanaka factors).

Pluripotency genes or proteins may comprise oct4, sox2, Klf4, cmyc, Lrh1 and Rarg.

These six pluripotency factors have been shown to induce iPS cells from non-pluripotent cells with high efficiency (Wang et al 2011).

In any of the embodiments described herein the pluripotency genes or proteins may further comprise Nanog and Lin28.

Preferably, the pluripotent cells are iPSCs or ESCs. The pluripotent cells may be a pre-implantation embryo or individual blastocyst. When the pluripotent cells are human, they may be obtained without destruction of a human embryo using known techniques as discussed herein.

The iPSCs may be obtained from a mammalian individual. For example, in some embodiments, the iPSCs may be derived from somatic cells or other antecedent cells obtained from an individual. The iPSCs may be used to produce a population of EPSCs which share the genotype of that individual. In some embodiments the EPSCs or cells differentiated therefrom in vitro produced from an individual, may be useful in studying the mechanisms of a disease condition associated with that individual.

In some embodiments, a population of pluripotent cells may be obtained from a cultured pluripotent cell line. Conventional techniques may be employed for the culture and maintenance of human pluripotent cells (Vallier, L. et al Dev. Biol. 275, 403-421 (2004), Cowan, C. A. et al. N. Engl. J. Med. 350, 1353-1356 (2004), Joannides, A. et al. Stem Cells 24, 230-235 (2006) Klimanskaya, I. et al. Lancet 365, 1636-1641 (2005), Ludwig, T. E. et al. Nat. Biotechnol. 24, 185-187 (2006)). Pluripotent cells for use in the present methods may be grown in defined conditions or on feeder cells. For example, pluripotent cells may be conventionally cultured in a culture dish on a layer of feeder cells, such as irradiated mouse embryonic fibroblasts (MEF), at an appropriate density (e.g. 105 to $10^6$ cells/60 mm dish), or on an appropriate substrate with feeder conditioned or defined medium. Pluripotent cells for use in the present methods may be passaged by enzymatic or mechanical means.

Suitable culture media for pluripotent cells are well-known in the art and include; Knockout Dulbecco's Modified Eagle's Medium (KO-DMEM) supplemented with 20% Serum Replacement, 1% Non-Essential Amino Acids, 1 mM L-Glutamine, 0.1 mM β-mercaptoethanol and 4 ng/ml to 10 ng/ml FGF2; or Knockout (KS) medium supplemented with 4 ng/ml FGF2; or KO-DMEM supplemented with 20% Serum Replacement, 1% Non-Essential Amino Acids, 1 mM L-Glutamine, 0.1 mM β-mercaptoethanol and 4 ng/ml to 10 ng/ml human FGF2; or DMEM/F12 supplemented with 20% knockout serum replacement (KSR), 6 ng/ml FGF2 (PeproTech), 1 mM L-Gln, 100 μm non-essential amino acids, 100 μM 2-mercaptoethanol, 50 U/ml penicillin and 50 mg/ml streptomycin.

In some preferred embodiments, a population of pluripotent cells for use in the present methods may be cultured in a chemically defined medium (CDM) which comprise a chemically defined basal medium supplemented with a serum-free media supplement and/or one or more additional components, for example transferrin, 1-thioglycerol and defined lipids and optionally polyvinyl alcohol; polyvinyl alcohol and insulin; serum albumin; or serum albumin and insulin.

Suitable serum-free media supplements for use in the media described herein include B27 (Brewer et al Brain Res (1989) 494 65-74; Brewer et al J. Neurosci Res 35 567-576 (1993); Brewer et al Focus 16 1 6-9; Brewer et al (1995) J. Neurosci. Res. 42:674-683; Roth et al J Trace Elem Med Biol (2010) 24 130-137) and NS21 (Chen et al J. Neurosci Meths (2008) 171 239-247), and knockout serum replacement (KSR). Serum-free media supplements, such as B27, KSR and N21, are well known in the art and widely available commercially (e.g. Invitrogen; Sigma Aldrich Inc, Life Technologies).

Suitable chemically defined media include CDM-PVA (Johansson and Wiles (1995) Mol Cell Biol 15, 141-151), which comprises a basal medium supplemented with polyvinyl alcohol, insulin, transferrin and defined lipids. For example, a CDM-PVA medium may consist of: 50% Iscove's Modified Dulbecco's Medium (IMDM) plus 50% Ham's F12 with GlutaMAX-1™ or 50% F12 NUT-MIX (Gibco, supplemented with 1% chemically defined lipid concentrate, 450 μM 1-thiolglycerol, 15 μg/ml transferrin, 1 mg/ml polyvinyl alcohol, 7 μg/ml Insulin. Other suitable chemically defined nutrient media include hESC maintenance medium (CDMA) which is identical to the CDM-PVA described above with the replacement of PVA with 5 mg/ml BSA; and RPMI basal medium supplemented with B27 and Activin (for example at least 50 ng/ml).

CDM-PVA media are described in Vallier et al 2009 PLoS ONE 4: e6082. doi: 10.1371; Vallier et al 2009 Stem Cells 27: 2655-2666, Touboul 2010 51: 1754-1765. Teo et al 2011 Genes & Dev. (2011) 25: 238-250 and Peterson & Loring Human Stem Cell Manual: A Laboratory Guide (2012) Academic Press.

In order to maintain pluripotency, the pluripotent cells may be maintained in CDM supplemented with Activin and FGF before culturing in the EPSCM. For example, a CDM may further comprise FGF2 (for example, 10 to 20 ng/ml, e.g. 12 ng/ml) and activin A (for example, 10 ng/ml) (Vallier et al. 2005 J Cell Sci 118:4495-4509; Brons et al Nature. (2007) July 12; 448(7150):191-5).

Suitable techniques for cell culture are well-known in the art (see, for example, Basic Cell Culture Protocols, C. Helgason, Humana Press Inc. U.S. (15 Oct. 2004) ISBN: 1588295451; Human Cell Culture Protocols (Methods in Molecular Medicine S.) Humana Press Inc., U.S. (9 Dec. 2004) ISBN: 1588292223; Culture of Animal Cells: A Manual of Basic Technique, R. Freshney, John Wiley & Sons Inc (2 Aug. 2005) ISBN: 0471453293, Ho W Y et al J Immunol Methods. (2006) 310:40-52, Handbook of Stem Cells (ed. R. Lanza) ISBN: 0124366430) Basic Cell Culture Protocols' by J. Pollard and J. M. Walker (1997), 'Mammalian Cell Culture: Essential Techniques' by A. Doyle and J. B. Griffiths (1997), 'Human Embryonic Stem Cells' by A. Chiu and M. Rao (2003), Stem Cells: From Bench to Bedside' by A. Bongso (2005), Peterson & Loring (2012) Human Stem Cell Manual: A Laboratory Guide Academic Press and 'Human Embryonic Stem Cell Protocols' by K. Turksen (2006). Media and ingredients thereof may be obtained from commercial sources (e.g. Gibco, Roche, Sigma, Europa bioproducts, R&D Systems). Standard mammalian cell culture conditions may be employed for the above culture steps, for example 37° C., 21% Oxygen, 5% Carbon Dioxide. Media is preferably changed every two days and cells allowed to settle by gravity.

A population of pluripotent cells suitable for use in the present methods may be heterogeneous or may be substantially free from one or more other cell types (i.e. homogenous). Preferably they are a homogeneous population of one cell type. Pluripotent cells may, for example, be separated from other cell types, using any technique known to those skilled in the art, including those based on the recognition of extracellular epitopes by antibodies and magnetic beads or fluorescence activated cell sorting (MACS or FACS) including the use of antibodies against extracellular regions of molecules found on stem cells, such as SSEA4.

A population of pluripotent cells for use in the present methods may be cultured in the expanded potential stem cell medium (EPSCM) described herein to produce a population of EPCSs. Once converted, the EPSCs may be cultured in an EPSC maintenance medium (EPSCMM). The maintenance medium may have the same composition as the EPSCM or may have a different composition as described herein, for example, the maintenance medium may contain fewer inhibitors/modulators compared to the EPSCM which was used for converting the cells. Once converted it is believed that EPSCs may not require as many inhibitors/modulators to maintain them in culture as EPSCs.

A suitable EPSCM may comprise or consist of one or more:
a RAS-ERK inhibitor,
a Jun N-Terminal Kinase (JNK) inhibitor,
a p38 inhibitor,
a Src Kinase family (SFK) inhibitor,
a GSK3 inhibitor
a Wnt inhibitor,
a notch modulator,
an integrin modulator, and
a Hippo modulator.

Optionally the EPSCM may also contain LIF and/or IGF-II. The EPSCM may contain a nutrient medium.

A suitable EPSCM or EPSCMM may comprise or consist of a nutrient medium together with one or more of a Ras-ERK inhibitor, a Jun N-Terminal Kinase (JNK) inhibitor, a p38 inhibitor, a Src Kinase family (SFK) inhibitor, a GSK3 inhibitor and a Wnt inhibitor.

A suitable EPSCM or EPSCMM may contain any two or three of the following inhibitors: Ras-ERK inhibitor, a Src Kinase family (SFK) inhibitor a GSK3 inhibitor and a Wnt inhibitor. For example, the EPSCM or EPSCMM may contain an SFK inhibitor and a GSK3 inhibitor.

A suitable EPSCM or EPSCMM may contain the following four inhibitors: Ras-ERK inhibitor, a Src Kinase family (SFK) inhibitor a GSK3 inhibitor and a Wnt inhibitor.

A suitable EPSCM or EPSCMM may contain the following two inhibitors: a Src Kinase family (SFK) inhibitor and a GSK3 inhibitor.

A suitable EPSCM or EPSCMM may contain the following three inhibitors: a Src Kinase family (SFK) inhibitor, a GSK3 inhibitor and a Wnt inhibitor.

The EPSCM may optionally contain one or more of a notch modulator, an integrin modulator, and a Hippo modulator.

Preferably the nutrient medium is a chemically defined nutrient medium.

In some embodiments the EPSCM may comprise the following six inhibitors a Ras-ERK inhibitor, a Jun N-Terminal Kinase (JNK) inhibitor, a p38 inhibitor, a Src Kinase family (SFK) inhibitor a GSK3 inhibitor and a Wnt inhibitor.

An EPSCM containing these six inhibitors has been demonstrated to successfully generate EPSCs from both human and mouse cells.

In some embodiments the EPSCM may comprise a Ras-ERK inhibitor, a Src Kinase family (SFK) inhibitor, a GSK3 inhibitor and a Wnt inhibitor.

An EPSCM containing any two or three of these four factors has been demonstrated to successfully generate EPSCs from both human and mouse cells.

The EPSCM described herein may also contain a nutrient medium. The nutrient medium may be a chemically defined nutrient medium.

The nutrient medium may comprise or consist of a basal medium, which may be a chemically defined basal medium, optionally supplemented with one or more additional defined components, such as vitamins, antibiotics, amino acids, polyvinyl alcohol, 1-thioglycerol, insulin, transferrin and defined lipids.

Suitable chemically defined basal media are described above and include Iscove's Modified Dulbecco's Medium (IMDM), Ham's F12, Advanced Dulbecco's modified eagle medium (DMEM/F12) (Price et al Focus (2003), 25 3-6), RPMI-1640 (Moore, G. E. and Woods L. K., (1976) Tissue Culture Association Manual. 3, 503-508). A preferred chemically defined basal medium is AlbuMax, or AlbumaxII medium.

The basal medium may be knockout serum replacement (KSR).

The basal medium may be supplemented by serum-containing or serum-free culture medium supplements and/or additional components. Suitable supplements and additional components are described above and may include L-glutamine or substitutes, such as GlutaMAX-1™, chemically defined lipids, albumin, 1-thiolglycerol, polyvinyl alcohol, insulin, vitamins, such as vitamin C, antibiotics such as penicillin and/or streptomycin and transferrin.

Suitable chemically defined nutrient media for use in the EPSC medium include CDM-PVA and CDM-BA as described above.

The EPSC medium contains differentiation factors. Differentiation factors are factors which modulate, for example promote or inhibit, a signalling pathway which mediates differentiation in a mammalian cell. Differentiation factors may include growth factors, cytokines and inhibitors. The EPSCM contains defined inhibitors and/or modulators as described herein. The EPSCM may further contain LIF, which is a cytokine and/or IGF-II which is a growth factor.

The addition of LIF and/or IGF-II is not required for the conversion of PSCs to EPSCs but can enhance self-renewal of EPSCs.

Media may be supplemented with effective amounts of the differentiation factors set out above, as described elsewhere herein.

Each of the inhibitors or modulators may be added to the EPSCM to an amount of 0.1 µM to 20 µM; 0.1 µM to 15 µM preferably 0.1 µM to 10 µM. Each of the inhibitors may be added in an amount of 0.1 µM; 0.2 µM; 0.3 µM; 0.4 µM; 0.5 µM, 1 µM 2 µM 3 µM, 4 µM, 5 µM, 6 µM, 7 µM, 8 µM, 9 µM, 10 µM, 11 µM, 12 µM 13 µM, 14 µM or 15 µM.

Preferably, the inhibitors may be added in the following amounts: GSK3 inhibitor 3 µM, Ras-Erk inhibitor 1 µM, JNK inhibitor 4 µM, p38 inhibitor 10 µM, src inhibitor 0.3 µM and wnt inhibitor 5.0 µM.

LIF may be added in an amount of 1 µg/ml to 50 µg/ml; 1 µg/ml to 20 µg/ml; 5 µg/ml to 15 µg/ml. For example, LIF may be added in an amount of 5 µg/ml; 6 µg/ml; 7 µg/ml; 8 µg/ml; 9 µg/ml; 10 µg/ml; 1 µg/ml; 12 µg/ml; 13 µg/ml; 14 µg/ml; or 15 µg/ml. Preferably the LIF is added in an amount of 10 µg/ml.

IGF-II may be added in an amount of 1 µg/ml to 500 µg/ml; 50 µg/ml to 150 µg/ml; 75 µg/ml to 175 µg/ml. For example, LIF may be added in an amount of 5 µg/ml; 10 µg/ml; 15 µg/ml; 20 µg/ml; 25 µg/ml; 30 µg/ml; 35 µg/ml; 40 µg/ml; 45 µg/ml; 50 µg/ml; 55 µg/ml; 60 µg/ml; 65 µg/ml; 70 µg/ml; 75 µg/ml; 80 µg/ml; 85 µg/ml; 90 µg/ml; 95 µg/ml; 100 µg/ml; 105 µg/ml; 110 µg/ml; 115 µg/ml; 120 µg/ml; 125 µg/ml; 130 µg/ml; 135 µg/ml; 140 µg/ml; 145 µg/ml; 150 µg/ml; 175 µg/ml; 200 µg/ml; 250 µg/ml. Preferably the LIF is added in an amount of 100 µg/ml.

The EPSC medium may contain one or more of a Ras-ERK inhibitor, a Jun N-Terminal Kinase (JNK) inhibitor, a p38 inhibitor, a Src Kinase family (SFK) inhibitor, a GSK3 inhibitor, a Wnt inhibitor, a notch modulator, an integrin modulator, and a Hippo modulator.

For example, the EPSCM may contain, one, two, three, four, five, six, seven, eight or nine of the inhibitors and/or modulators listed above. The EPSCM may comprise a RAS-ERK inhibitor, a Jun N-Terminal Kinase (JNK) inhibitor, a p38 inhibitor, a Src Kinase family (SFK) inhibitor, a GSK3 inhibitor and a Wnt inhibitor.

The EPSCM may comprise a Ras-ERK inhibitor, an SFK inhibitor, a GSK3 inhibitor, a JNK inhibitor and a wnt inhibitor A reduced EPSCM lacking the JNK and p38 inhibitors has been demonstrated to successfully confer pluripotent cells with the expended potential in mice.

Therefore, EPSCM may comprise any two or three out of a RAS-ERK inhibitor, a Src Kinase family (SFK) inhibitor, a GSK3 inhibitor and a Wnt inhibitor.

The EPSCM may comprise a GSK3 inhibitor and an SFK inhibitor.

The EPSCM may comprise a Mek1 inhibitor, GSK3 inhibitor and SFK inhibitor.

The EPSCM may comprise a Mek1 inhibitor, GSK3 inhibitor and wnt inhibitor.

The EPSCM may comprise a GSK3 inhibitor, SFK inhibitor and wnt inhibitor.

An EPSCM containing Ras-ERK, SFK, GSK3, JNK and wnt inhibitors has been demonstrated to successfully confer pluripotent cells with the expended potential in pigs and humans.

Therefore, the EPSCM may comprise a Ras-ERK inhibitor, SFK inhibitor, GSK3 inhibitor, JNK inhibitor and a wnt inhibitor. The Ras-Erk inhibitor may be a Mek inhibitor or a Raf inhibitor. The RAS-ERK inhibitor is preferably a Braf inhibitor.

In any of the embodiments herein, the Mek1 inhibitor may be PD0325901, the Braf inhibitor may be SB590885, the GSK3 inhibitor CHIR99021, the wnt inhibitor XAV939 and/or the SFK inhibitor may be Wh-4 or A419259. Other suitable inhibitors are commercially available.

EPSC medium containing these inhibitors and/or modulators is shown herein to result in the production of EPSCs.

Suitable inhibitors or modulators include natural and synthetic small molecule inhibitors or antibodies.

Suitable Ras-ERK, JNK, p38, Src, GSK3 and Wnt pathway inhibitors are known in the art and are commercially available. The Ras-ERK pathway (also known as the MARK/ERK or Ras-Raf-MEK-ERK pathway) is chain of proteins in the cell that communicates a signal from a receptor on the surface of the cell to the DNA in the nucleus of the cell. The major proteins in this pathway are Ras, Raf, MEK and ERK. Inhibiting these proteins will disrupt signalling in this pathway. Thus, the inhibitor may directly or indirectly inhibit Ras, Raf, MEK or ERK such that signalling in this pathway is disrupted. For example, the inhibitor may be a Ras inhibitor, Raf inhibitor, MEK inhibitor or ERK inhibitor.

Preferably the Ras-ERK inhibitor is a MEK inhibitor.

Preferably the Ras-ERK inhibitor is a Raf inhibitor. Preferably the Ras-ERK inhibitor is a Braf inhibitor. The Ras-ERK inhibitor may be a Raf or Mek inhibitor.

Many Ras-ERK inhibitors are known and are commercially available.

Suitable Ras-ERK inhibitors include MEK inhibitors such as PD0325901 (Sigma-Aldrich PZ0162—PD 0325901), a selective, cell permeable MEK1/2 inhibitor that inhibits the activation and downstream signalling of MEK (MEK1 and MEK2). Other MEK inhibitors include PD 334581, PD 198306, PD 184352, Arctigenin, BIX 02189, PD 98059 which are commercially available from Tocris Bioscience( ) Ras inhibitors include Farnesyl Thiosalicylic Acid (catalogue number sc-221800) and FPT Inhibitor II (catalogue number sc-221626), Manumycin A (sc-200857), L-744,832 Dihydrochloride (sc-221800), FTI-276 trifluoroacetate salt (sc-215057) available from ChemCruz Biochemicals Raf inhibitors include SB 590885 (cat no 2651), AZ 628 (cat no 4836), GDC 0879 (cat no 4453), GW 5074 (cat no 1381), L-779 450 (cat no 3185), ML 786 dihydrochloride (cat no 5036) and ZM 336372 (cat no 1321) all available from Tocris Bioscience. Raf inhibitors are preferred types of Ras-ERK inhibitors.

The RAF family of proteins includes 3 isoforms: ARAF, BRAF, and CRAF. Braf is the main activator of MEK and a Braf inhibitor will inhibit MEK activation. Therefore, Braf inhibitors are preferred types of Ras-ERK inhibitors. Braf inhibitors include SB590885 (Tocris Bioscience).

ERK inhibitors include ERK Inhibitor III (catalogue number sc-221595), XMD 8-92 triflate (sc-361408) from ChemCrux Biochemicals and FR 180204 or TCS ERK 1ie from Tocris Bioscience.

Suitable Jun N-Terminal Kinase (JNK) inhibitors include JNK Inhibitor VIII (catalogue number sc-202673), RWJ 67657 (catalogue number sc-204251), Antibiotic LL Z1640-2 (catalogue number sc-202055), SX 011 (sc-358841), Bentamapimod (sc-394312), AEG 3482 (sc-202911).

Suitable p38 inhibitors include sB203580 which inhibits both the α and β isoforms of p38 MAPK, p38 MAP Kinase Inhibitor IV (catalogue number sc-204159), LY2228820 (catalogue number sc-364525), PH-797804 (catalogue number sc-364579), p38 MAP Kinase Inhibitor (catalogue number sc-204157), SX 011 (sc-358841) and 2-(4-Chlorophenyl)-4-(fluorophenyl)-5-pyridin-4-yl-1,2-dihydropyrazol-3-one (sc-220665).

The Src family kinases (SFK) are a family of non-receptor tyrosine kinases that included nine highly related members. Broad spectrum Src Kinase family inhibitors which inhibit multiple src family members are available and known in the art. Suitable Src Kinase family inhibitors include A-419259 which is a broad spectrum Src family kinase inhibitor. Other suitable SRK inhibitors include PP1, PP2 and CGP77675 also available from Sigma-Aldrich, and A419259 trihydrochloride or KB SRC 4 available from Tochris Bioscience.

Suitable GSK3 inhibitors include CHIR99021, a selective and potent GSK3 inhibitor available from Tocris Bioscience (cat 4423), or BIO (cat 3194), A 1070722 (cat 4431), 3F8 (cat 4083), AR-A 014418 (cat 3966), L803-mts (cat 2256) and SB 216763 (cat 1616) also available from Tocris Bioscience. Other suitable GSK inhibitors include GSK-3 Inhibitor IX (available from Santa Cruz Biotechnology sc-202634)

The Wnt inhibitor is an antagonist of the Wnt/β-catenin signalling pathway.

The Wnt/β-catenin signalling pathway is the Wnt pathway that causes an accumulation of β-catenin in the cytoplasm and its eventual translocation into the nucleus. In the absence of wnt signaling β-catenin is degraded by a destruction complex which includes the proteins Axin, adenomatosis polyposis coli (APC), protein phosphatase 2A (PP2A), glycogen synthase kinase 3 (GSK3) and casein kinase 1α (CK1α). The destruction complex degrades β-catenin by targeting it for ubiquitinization which subsequently sends it to the proteosome to be digested.

Preferably the Wnt inhibitor inhibits ubiquitinization of the β-catenin destruction complex, which stabilises the destruction complex and prevents β-catenin accumulation, thereby inhibiting wnt signalling.

Axin forms the 'scaffold' of the β-catenin destruction complex and is the negative wnt regulator. Preferably the Wnt inhibitor stabilises axin protein e.g by inhibiting axin ubiquitinization or binding directly to axin2.

Inhibiting axin ubiquitinization stabilises axin protein (because ubiquitinization leads to axin destruction) and inhibits wnt signalling by maintaining the β-catenin destruction complex.

The wnt inhibitor may be a tankyrase inhibitor. Tankyrase inhibition inhibits axin ubiquitinisation and stabilises axin protein (Huang et al 2009), therefore inhibiting wnt signalling.

A suitable tankyrase inhibitor is XAV939 (www.sigmaaldrich.com). Additional published tankyrase inhibitors include WIKI4, TC-E 5001 and JW 55, all commercially available from Tocris.

The wnt inhibitor may also stabilise Axin by directly binding to Axin. For example, the wnt inhibitor IWR-1 stabilises axin by directly binding to Axin2 (see Chen B, et al 2009). Chen et al show that that IWR compounds (IWR-1 to 5) do not 'induce de novo synthesis of Axin2, inhibit the proteasome, alter the affinity of Axin2 for β-catenin or its ability to interact other pathway components or disrupt subcellular localization of Axin. Thus, the IWR 1-5 inhibitors are also suitable wnt inhibitors.

The wnt inhibitor may inhibit Wnt processing and secretion. For example, IWP-2 (Sigma-Aldrich) is an inhibitor of Wnt production. IWP-2 inactivated Porcn function. Porcn is a member of the membrane-bound O-acyltransferase (MBOAT) family, which adds a palmitoyl group to Wnt proteins that is essential to their signaling ability and is required for Wnt secretion.

Other suitable wnt inhibitors include TAK 715 (catalogue number sc-362799) an inhibitor of Wnt/β-catenin available from www.scbt.com and iCRT 14 which is a potent inhibitor of β-catenin-responsive transcription (CRT) directly influencing the interaction between β-catenin and TCF4 (available from Tocris).

IWP-2 and iCRT 14 have been successfully used as the wnt inhibitor in EPSCM in place of XAV939.

Other suitable wnt inhibitors are known in the art and are commercially available.

Suitable modulators of the notch, integrin, and Hippo pathways are known and are also commercially available.

Modulators include both activators and inhibitors. For example, in order to inhibit a pathway, it is possible inhibit a component or the pathway directly or to activate a negative regulator of the pathway.

Thus, the EPSCM may comprise one or more notch and/or integrin and/or hippo pathway inhibitors.

The EPSCM may comprise one or more notch and/or integrin and/or hippo pathway activators. The EPSCM may comprise a combination or inhibitors and activators.

Notch inhibitors include those which target (or inhibit) gamma-secretase which cleaves Notch intracellular domain, which in turn acts as a transcription co-activator. Thus, in some embodiments the notch inhibitor is a gamma-secretase inhibitor. Various notch inhibitors are commercially available and include DBZ (cat no. 4489) www.tocris.com DAPT (Sigma-Aldrich) LY-685458 (Lilly) and RO4929097 (Selleckchem.com).

Integrin inhibitors may target (inhibit) integrin receptors. Integrin inhibitors are commercially available and include RGD peptide (GRGDNP) (ChemCruz Biochemicals).

The Hippo pathway is well known in the segregation of the TE and ICM. This pathway ultimately represses a transcription factor (yes-associated protein) YAP, which promotes the TE.

Briefly, the Hippo pathway consists of a core kinase cascade in which Hpo (MST1/2 in mammals) phosphorylates the protein kinase Warts (Wts). Once phosphorylated, Wts (LATS1/2) becomes active. Activated Wts can then go on to phosphorylate and inactivate the transcriptional coactivator Yes-associated protein (YAP)/Yorkie (Yki).

Hippo pathway inhibitors are commercially available and well known to the skilled person. For example, the inhibitor may be a Lats inhibitor such as LPA or S1P. LPA and S1P activate YAP/TAZ activity by inhibiting Lats kinase (Yu et al 2012).

In a preferred embodiment, the EPSCM may contain a wnt inhibitor which stabilises axin, together with one or more of the inhibitors or modulators disclosed herein. Thus, the EPSCM may contain a wnt inhibitor which stabilises axin together with one or more of a Mek inhibitor, a GSK3 inhibitor, a JNK inhibitor, a p38 inhibitor, a Src inhibitor, a notch inhibitor and an integrin inhibitor.

Wnt inhibitors which stabilise axin are known in the art as discussed herein and include IWR-1 and XAV939.

The EPSC medium may comprise or consist of DMEM/F12, supplemented with a MEK inhibitor, a JNK Inhibitor, a p38 inhibitor, an Src inhibitor, a tankyrase inhibitor and a GSK3 inhibitor.

The EPSC medium may comprise or consist DMEM/F12 or N2B27. The EPSCM may be supplemented with the inhibitors PD0325901, JNK Inhibitor VIII, SB203580, A-419259, XAV939 and CHIR99021.

The EPSC medium may comprise or consist of DMEM/F12 or N2B27, supplemented with a Raf inhibitor (preferably a Braf inhibitor), a JNK inhibitor, an SRC inhibitor, a GSK3 inhibitor and a wnt inhibitor.

The EPSC medium may comprise or consist of DMEM/F12 or N2B27, supplemented with the inhibitors SB 590885, SP600125, Wh-4, CHIRON99021 and XAV939.

In any embodiment described herein, the EPSCM may also comprise LIF (leukemia inhibitory factor) and/or IGF-II (insulin-like growth factor II) since these have been shown to function in enhancing ESC self-renewal. The EPSCM may comprise Activin (Peprotech) and/or FBS (for optimal cell proliferation.

In some embodiments, the EPSCM may contain the inhibitor ROCK (ROCKi).

In some embodiments, the EPSCM may not contain one, two, three or four of the inhibitors PKC, ROCK, BMP and BRAF. In some embodiments, the EPSCM may not contain the growth factors FGF and/or TGFβ/activin. The EPSCM may be devoid of differentiation factors other than one or more of a Ras-ERK inhibitor, a Jun N-Terminal Kinase (JNK) inhibitor, a p38 inhibitor, a Src Kinase family (SFK) inhibitor, a GSK3 inhibitor, a Wnt inhibitor, a notch modulator, an integrin modulator, and a Hippo modulator, and, optionally, LIF and IGF-II. The EPSC medium may consist of a chemically defined nutrient medium supplemented with an effective amount of an inhibitor or modulator described herein.

An effective amount is an amount which is sufficient to inhibit signalling in the pathway or by the protein which is targeted.

The present inventors have further observed that for some PSC populations when the population of PSCs is cultured in EPSCM, the resulting genetically stable population of EPSCs are derived from a subset of the original PSC population. This has particularly been observed when culturing human ES cells in EPSCM, such as H1 cells although it does not occur when culturing all human cells in EPSCM. For example, this has not been observed when culturing H9 cells. Furthermore, this has not been observed for mouse ESCs. Without being bound by theory, it is believed that some PSC populations, and particularly human ESCs, may be heterogeneous in terms of their 'stemness', with some more PSCs being more 'naïve' and some cells more 'primed'. Cells which survive in the EPSCM are believed to be those which are more 'naïve'. Thus, EPSCM can be used to sort a heterogeneous PSC population of mixed stemness into a more homogeneous population. In other words, culturing PSCs in the EPSCM produces and selects for a more homogenous, genetically stable EPSC population.

Thus, in one aspect the invention provides a method of sorting a heterogeneous population of naïve and primed pluripotent stem cells (PSCs) into a homogeneous population of expanded potential stem cells (EPSCs), the method comprising culturing the PSCs in an expanded potential stem cell medium (EPSCM) as described herein, thereby producing a homogeneous population of EPSCs.

The PSCs may be any cell type described herein. The PSC population is from a single cell line. The PSCs are preferably ES cells, more preferably human ESCs as described herein. The PSCs may be a population having mixed (heterogeneous) stemness potential e.g. a mixture of naïve and primed-type PSCs.

The population of EPSCs obtained after culturing in the EPSCM is more homogenous in terms of its stemness compared to the starting population of PSCs. The resulting EPSCs are a genetically stable population.

The pluripotent stem cells (e.g. ESCs or iPSCs) may be mammalian. For example, the pluripotent stem cells may be rodent (e.g. mouse, rat), pig, sheep, goat, cow, rabbit, primate (including humans and non-human primates). Preferably the pluripotent stem cells are human. The resulting EPSCs will therefore be human EPSCs (hEPSCs).

The expanded potential stem cell medium (EPSCM) may be a chemically defined medium (CDM).

A chemically defined medium (CDM) is a nutritive solution for culturing cells which contains only specified components, preferably components of known chemical structure. A CDM is devoid of undefined components or constituents which include undefined components, such as feeder cells, stromal cells, serum, matrigel, serum albumin and complex extracellular matrices. In some embodiments, the chemically defined medium is humanised. A humanised chemically defined medium is devoid of components or supplements derived or isolated from non-human animals, such as Foetal Bovine Serum (FBS) and Bovine Serum Albumin (BSA), and mouse feeder cells. Conditioned medium includes undefined components from cultured cells and is not chemically defined.

Suitable chemically defined basal medium, such as Advanced Dulbecco's modified eagle medium (DMEM) or DMEM/F12 (Price et al Focus (2003) 25 3-6), Iscove's Modified Dulbecco's medium (IMDM) and RPMI-1640 (Moore, G. E. and Woods L. K., (1976) Tissue Culture Association Manual. 3, 503-508; see Table 1), knockout serum replacement (KSR) are known in the art and available from commercial sources (e.g. Sigma-Aldrich MI USA; Life Technologies USA).

Preferably the basal medium is DMEM/F12. The basal medium may comprise or may be supplemented with, AlbuMAX II, which is a commercially available BSA or knockout serum replacement (KSR). The basal medium may also be supplemented with any or all of insulin (preferably human), N2, B27, L-Glutamine, antibiotics (preferably Penicillin and Streptomycin); Non-Essential Amino Acids; vitamins (preferably vitamin C) and basal medium eagle (bME), all of which are commercially available (for example from Sigma-Aldrich). Other suitable supplements are known in the art and described herein.

Glutamine, Penicillin and Streptomycin are commercially available as a Glutamine-Penicillin-Streptomycin mix, (containing 200 nM L-glutamine, 10,000 units penicillin and 10 mg/ml streptomycin) for example from Signa-Aldrich.

An example of an EPSCM comprises or consists of DMEM/F12 basal medium; supplemented with AlbuMAX II or Knockout Serum Replacement and the inhibitors and modulators described herein. The EPSCM may also comprise any of human insulin; N2, B27; Glutamine-Penicillin-Streptomycin; Non-Essential Amino Acids; vitamin C and basal medium eagle (bME), LIF and IGF-II.

EPSCs have been successfully obtained by culturing PSCs in an EPSCM which uses a DMEM/F12 basal medium and which is supplemented with either AlbuMAX II or Knockout Serum Replacement, and the inhibitors or modulators described herein.

A preferred example of an EPSCM comprises or consists of DMEM/F12 basal medium; supplemented with AlbuMAX II; human insulin; N2, B27; Glutamine-Penicillin-Streptomycin; Non-Essential Amino Acids; vitamin C and basal medium eagle (bME), LIF, IGF-II and the inhibitors and modulators described herein.

A preferred EPSCM supplement comprises or consists of 20% AlbuMax II 8 mL; Human Insulin (25 mg/mL) 80 uL; B27 Supplement (50×) 2 mL; L-Glutamine-Penicillin-Streptomycin (100×) 1 mL; Non-essential Amino Acids (100×) 1 mL; Vitamin C (1000×) 100 uL; bME 1 uL; LIF (10 ug/mL) 10 uL; IGFII (100 ug/mL) 30 uL (total volume 100 ml). The inhibitors may be added as described herein.

The supplement is added to basal medium, preferably DMEM/F12 to a total volume of 100 ml to obtain the EPSCM.

The expanded potential stem cell medium (EPSCM) is suitable for culturing ESCs or iPSCs into EPSCs.

In some embodiments, the population of EPSCs is produced by culturing a population of pluripotent stem cells in the EPSCM for one or more (for example two or more, three or more, four or more, five or more) passages to produce a population of EPSCs. Passaging is also referred to as sub-culturing and is the transfer of cells from a previous culture into fresh growth medium. Cells in culture follow a characteristic growth pattern of lag phase, log phase and stationary phase. The timings of these phases may vary depending on the cell used (e.g. mammalian cells vs non-mammalian cells). Methods to determine the stage of cell growth are well known in the art. Generally, cells are passaged in log phase. In some embodiments the pluripotent stem cells may be passaged (subcultured) one to ten times, three to ten times, three to five times in the EPSCM, to produce the population of EPSCs. Preferably the population is passaged at least three times to produce the population of EPSCs.

In some embodiments a ROCK inhibitor (ROCKi) is added to the EPSCM. ROCK inhibitors are known in the art and are commercially available, for example from www.tocris.com. The addition of a ROCK inhibitor is not required for the conversion of PSCs to EPSCs but can enhance the single cell survival and plating of EPSCs.

The successful production of EPSCs can be identified by their morphologically distinct appearance compared to the originator population of pluripotent stem cells.

Once a population of EPSCs has been produced, the EPSCs may be maintained by culturing them in the EPSCM. EPSCs which are maintained or cultures in EPSCM are known to be stable.

EPSCs may subsequently be differentiated into other cell types using techniques which are known in the art.

For example, the EPSCs may be differentiated into trophoblasts. Techniques for differentiating pluripotent stem cells into trophoblasts are known and described herein. Thus, the EPSCs may be differentiated into trophoblasts by culturing the EPSCs in a trophoblast induction medium to induce trophoblast differentiation. The induction medium may be a FGF4-containing TSC medium. A suitable induction medium is described in Abad M, et al 201.

For human EPSCs, the trophoblast induction can be achieved using FGF4-containing TSC medium or alternatively using the standard human trophoblast differentiation protocol which contains BMP4, an ALK4/5/7 inhibitor (e.g A83-01) FGFR inhibitor (e.g. PD173074). (Amita M, et al 2013) Differentiated cells express HLA-G and FGFR4

FGF4-containing TSC medium has been successfully used to induce both mouse and human EPSCs into trophoblasts.

The EPSCs may be differentiated into somatic cells using standard differentiation techniques known. The somatic cells may be neurons (protocol described herein), pancreatic cells (protocol described in Cho C H, et al 2012), T-cells (protocol described in Themeli M, et al 2013) and primordial germ cells (PGCs) (Duggal G, et al 2013 and described herein).

The EPSC-PGCs may be KIT+ and SSEA1+, and express increased TRAI-81 compared to undifferentiated EPSC controls. The EPSC-PCGs may show increased expression of Stella and PRDM1 as measured by qPCR, compared to undifferentiated EPSC controls.

The EPSCs may be differentiated into trophoblasts using standard protocols. The EPSC-TSCs may have increased expression of Cdx2 and Eomes compared to control ESCs, indicating an increased propensity of EPSCs towards trophoblast differentiation.

EPSCs can be distinguished from ES cells. Molecular characterization reveals that EPSCs have distinct morphology, transcriptome and histone methylation patterns compared to ESCs, and exhibit partial DNA demethylation at the Cdx2 and Elf5 loci. Our data show that the transcriptome of EPSCs is also enriched with molecular signature of early blastomeres, although remains distinct from blastomeres.

EPSCs are extremely amenable to genome editing with a high gene targeting efficiency, for example using the CRISPR/Cas9 system described in Doudna, et al. *Science* 346, (2014) We have also achieved extremely efficient gene targeting of approximately 60% efficiency using standard (non-CRISPR/Cas9) gene targeting methods. The EPSCs or cells differentiated therefrom may be used in a method of treatment of the human or animal body.

The EPSCs or cells differentiated therefrom in vitro may be useful in a method of in vitro fertilization (IVF) or somatic-cell nuclear transfer. In some embodiments the EPSCs or cells differentiated therefrom are from a non-human mammal.

EPSCM as described herein may be formulated into a kit for sale.

The one or more culture media in the kit may be formulated in deionized, distilled water. The one or more media will typically be sterilized prior to use to prevent contamination, e.g. by ultraviolet light, heating, irradiation or filtration. The one or more media may be frozen (e.g. at −20° C. or −80° C.) for storage or transport. The one or more media may contain one or more antibiotics to prevent contamination.

The one or more media may be a 1× formulation or a more concentrated formulation, e.g. a 2× to 250× concentrated medium formulation. In a 1× formulation each ingredient in the medium is at the concentration intended for cell culture, for example a concentration set out above. In a concentrated formulation one or more of the ingredients is present at a higher concentration than intended for cell culture. Concentrated culture media are well known in the art. Culture media can be concentrated using known methods e.g. salt precipitation or selective filtration. A concentrated medium may be diluted for use with water (preferably deionized and distilled) or any appropriate solution, e.g. an aqueous saline solution, an aqueous buffer or a culture medium.

The one or more media in the kit may be contained in hermetically-sealed vessels. Hermetically-sealed vessels may be preferred for transport or storage of the culture media, to prevent contamination. The vessel may be any suitable vessel, such as a flask, a plate, a bottle, a jar, a vial or a bag.

The kit may also include instructions for use, e.g. for using the EPSCM to obtain EPSCs.

The invention also provides the use of an EPSCM as described herein to obtain EPSCs.

The invention also provides a cell culture comprising an EPSCM as described herein a population of pluripotent cells.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Certain aspects and embodiments of the invention will now be illustrated by way of example and with reference to the figures described above.

EXAMPLES

For convenience, a population of EPSCs obtained from pluripotent cells which are iPSCs may be called iPSC-EPSCs, while a population of EPSCs obtained from pluripotent cells which are ESCs may be called ESC-EPSCs.

EPSC Medium

We initially tested a six inhibitor medium containing inhibitors for the three major classes of MAPKs: Ras-ERK (PD0325901), Jun N-Terminal Kinase (JNK Inhibitor VIII) and p38 (SB203580). The medium also contains A-419259, a potent pyrrolopyrimidine inhibitor of the SFKs, and XAV939, which stabilizes Axin, the concentration-limiting component of the β-catenin and Yap destruction complex Huang et al. (2009), L. Azzolin et al (2014). We included GSK3 inhibitor (CHIR99021) to promote metabolic and biosynthetic processes in the cells (Doble et al. 2003). LIF was added since it functions in enhancing ES cell self-renewal and promotes rare totipotent cells in mouse ES cell culture (Morgani et al. 2013).

We hereafter named this medium the EPSC Medium or EPSCM for reasons described below.

We also tested a reduced EPSCM by removing inhibitors from the medium. In mice, several combinations of two or three inhibitors were able to confer mouse ESCs with substantially expanded potential. The successfully tested combinations include any two or three out of a Mek1 inhibitor, GSK3 inhibitor, SFK inhibitor and a wnt inhibitor. Therefore it appears that mouse EPSCM required a core of three inhibitors which do not include JNK and p38 inhibitors. These experiments are described below (see, 'Minimal sets of inhibitors for the expanded potential').

It was also possible to generate human EPSCs in a medium which contained only three inhibitors, a Src Kinase family (SFK) inhibitor a GSK3 inhibitor and a Wnt inhibitor when added to a chemically defined basal medium.

Mouse ESCs can Survive in EPSCM and Proliferate to EPSCs.

Figure 1A:
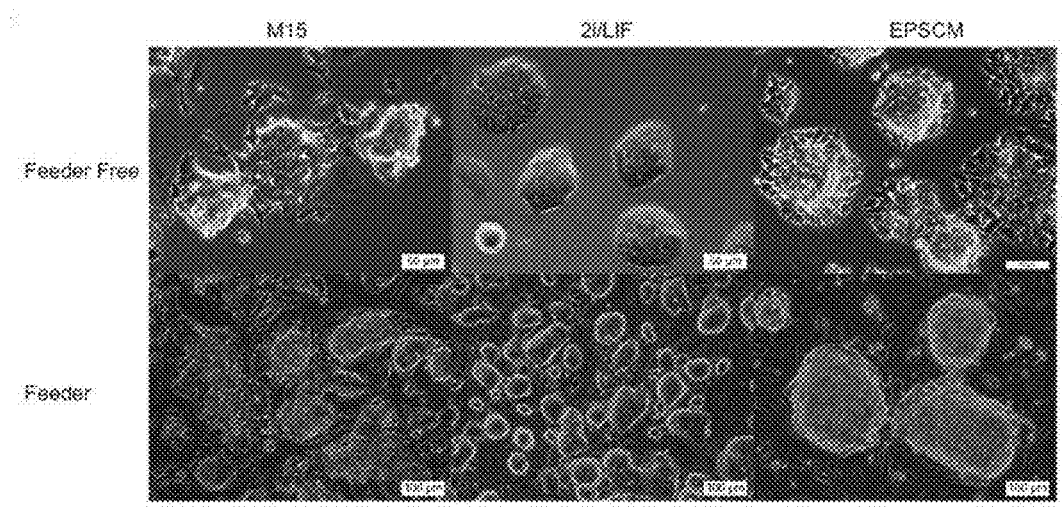
FIGS. 1A-1F shows that EPSCs from mouse ES cells are pluripotent and have the capacity to differentiate to trophoblasts in vitro.

We initially asked whether mouse ESCs were able to survive or propagate in EPSCM by testing two widely used ES cell lines, AB2.2 and E14 (Hooper et al 1987 *Nature* 326, 292 and Ramirez-Solis et al 1995 *Nature* 378, 720). Despite the presence of multiple inhibitors in EPSCM, ESCs previously cultured in either serum-containing medium (15% serum plus LIF or M15) or N2B27/2i/LIF (2i/LIF), all survived well in EPSCM and proliferated similarly to ESCs in M15 or 2i/LIF on feeders or feeder-free (FIG. 1A).

Figure 1B:
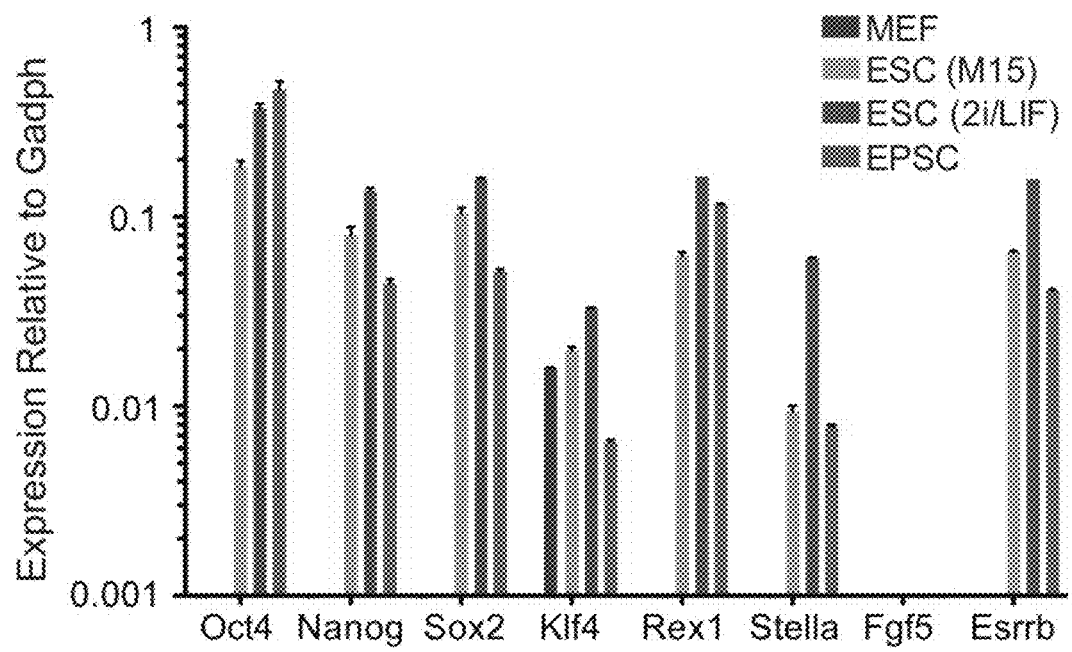
Figure 1C:
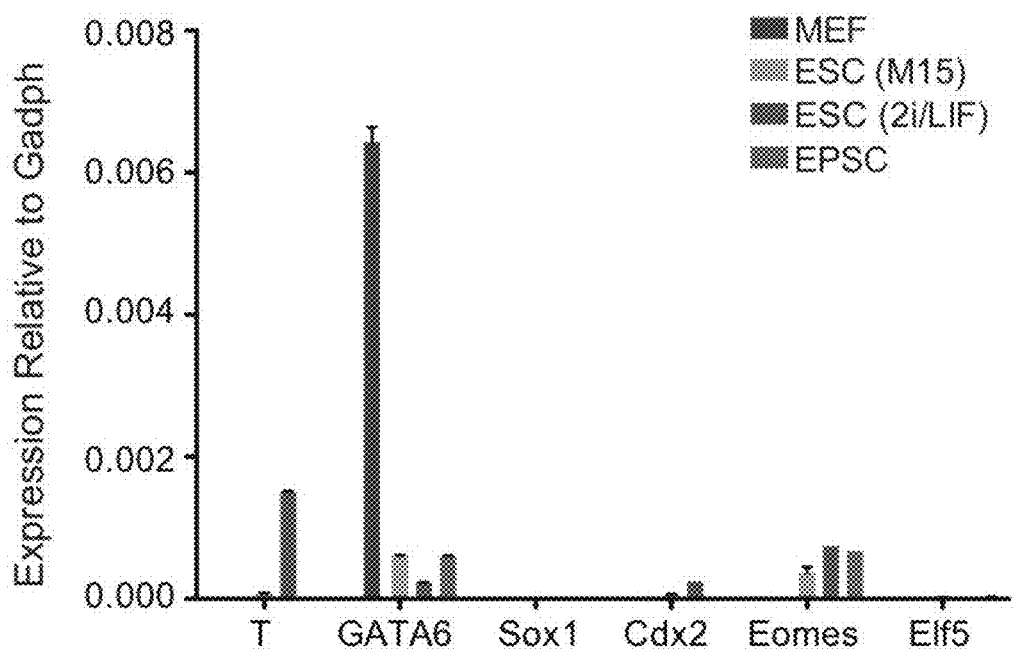

Zfp42 (Rex1) and Oct4 (Pou5f1) are pluripotency genes. Rex1-GFP or Oct4-GFP reporter ESCs cultured in EPSCM retained robust GFP expression. They were found to express similar levels of pluripotency genes compared to standard ESCs (FIG. 1B). Expression of lineage specific genes, including T (Brachyury), Gata6, Sox1, Cdx2, Eomes and Elf5, was similar to that in standard ESCs at the qRT-PCR resolution (FIG. 1C). ESCs cultured in EPSCM for three passages hereafter were called EPSCs. We next tested the plating efficiency of seeding 100 Rex1-GFP ESCs (pre-cultured in 2i/LIF or M15) in either EPSCM or in their original media on STO feeders. The numbers of GFP$^+$ colonies formed in EPSCM or in 2i/LIF were comparable, indicating that EPSCM was permissive and didn't substantially select naïve or ground state ESCs.

The distal enhancer of the Oct4 locus is specifically active in naive ESCs whereas the proximal enhancer is dominant in primed stem cells such as EpiSCs (Y. I. Yeom et al *Development* 122, 881 March, 1996; S. Bao et al., *Nature* 461, 1292 Oct. 29, 2009). Similar to standard ESCs, the distal enhancer is primarily active in EPSCs. EPSCs were able to differentiate in vitro to cell types of all three somatic germ layers. Importantly, once injected to blastocysts, they contributed efficiently in the live chimeras that did not show any obvious abnormalities in 10 months and had contribution of donor cells to the germline. EPSCs therefore retained canonical pluripotency features. This data shows that EPSCs contribute to the germline lineage and hence can give rise to a genetically modified (transgenic) stable mouse line. Thus, it appears that our EPSCs will be useful in making genetically modified non-human animal models.

We next confirmed inhibition of the respective kinase activities in EPSCM. EPSCM contains XAV, which inhibits Axin ubiquitination and stabilizes Axin protein (Huang et al 2009). EPSCs had considerably elevated Axin compared to the controls, which caused increased phosphorylated β-catenin in both the cytoplasm and the nucleus, and decreased active β-catenin in the nucleus. TopFash luciferase assay also showed reduced β-catenin-LEF/TCF activity (canonical Wnt pathway). EPSCs were dependent on the Jak/Stat pathway since a Jak inhibitor substantially reduced alkaline phosphatase (AP$^+$) colonies formed from AB2.2-EPSCs, whereas adding LIF increased phosphorylation of Stat3 and upregulated expression of Jak/Stat downstream genes.

On the other hand, EPSCs did not appear to be sensitive to inhibitors of FGFR or TGFBR, similar to 2i/LIF ESCs (Ying et al 2008)

ESCs Cultured in EPSCM can Differentiate into Trophoblast Cells.

We investigated the developmental potency of ESCs cultured in EPSCM. We initially determined the DNA methylation status in mouse EPSCs at the Elf5 and Cdx2 loci. Cdx2 is a key TE regulator and Elf5 is the hall marker gene for the trophoblast lineage (Hemberger et al 2010; Ng et al. 2008). Demethylation of the Elf5 locus is considered to be a key event for trophoblast fate specification and maintenance (Ng et al 2008). In Dnmt1-deficient ESCs which showed unusual differentiation to trophoblasts, the Elf5 promoter proximal to the transcriptional start site is hypomethylated (Ng et al 2008). We found that EPSCs showed substantial reduction of methylation levels at the Elf5 promoter, in particular near the transcription start site, compared to the parental ESCs, but the region still remained partially methylated compared to TSCs. Similarly, EPSCs also had decreased DNA demethylation in particular at the proximal promoter region of the Cdx2 locus. The lower DNA methylation levels at these two critical loci in EPSCs might be reflective of a cell state with expanded capacity to trophoblast differentiation.

Figure 1D:
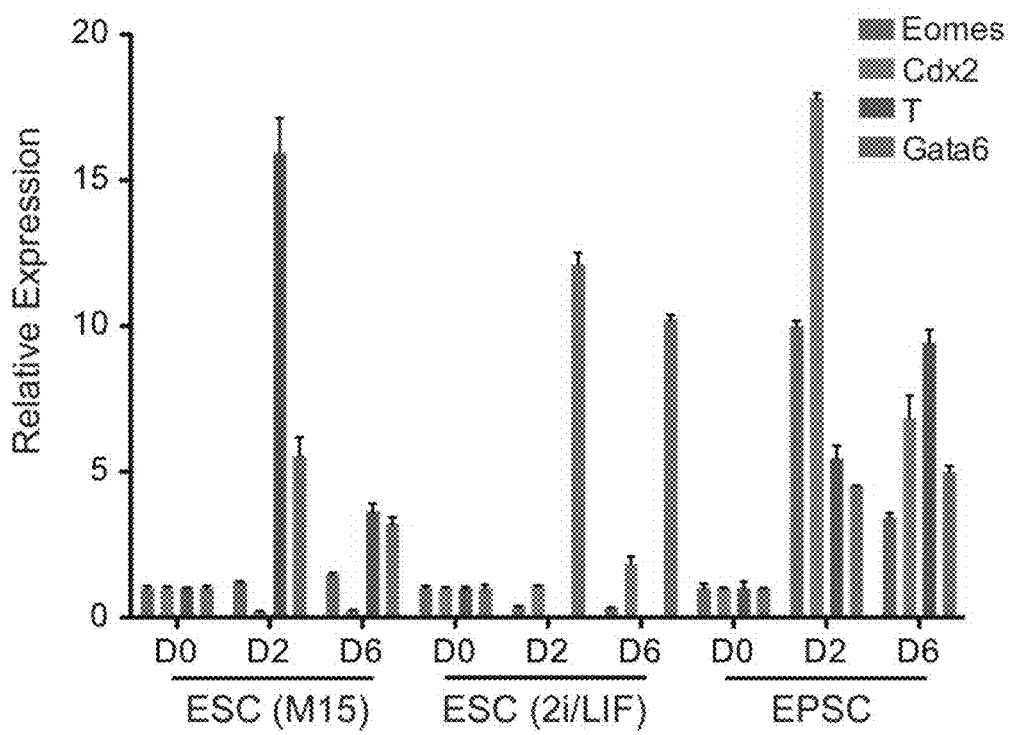
Figure 1E:
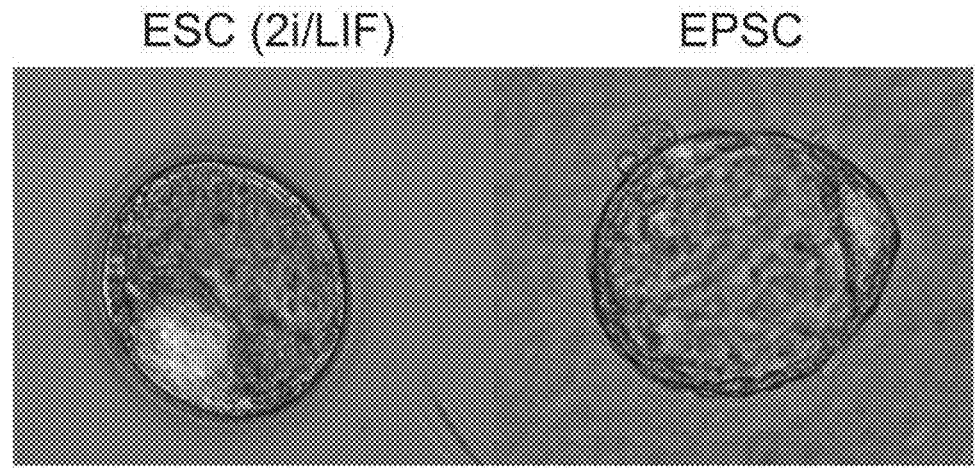

To investigate this possibility, we switched the culture condition of EPSCs to FGF4-containing TSC medium to induce trophoblast differentiation ((Tanaka et al 1998; Abad et al 2013). Cdx2, Eomes, Gata3 and Elf5 have been shown to promote or regulate the transcription network of trophectoderm development (Chen et al 2010). Rapid up-regulation of these genes indicates commitment of embryonic cells to trophoblast differentiation. After two days in TSC medium, expression of Cdx2 and Eomes in EPSCs was induced by 10-20 folds, indicating an increased propensity of EPSCs towards trophoblast differentiation (FIG. 1D). By contrast, no obvious expression changes of Cdx2 or Eomes were detected in control ESCs under the same condition (FIG. 1D). Following the differentiation protocol described in Nichols and Smith, Cell Stem Cell, 4, 487 (2009), these cells were differentiated to Placental Lactogen 1 (PL-1)$^+$ trophoblast-like cells following the removal of FGF4 (FIG. 1E). TSCs were differentiated as a control.

EPSCs can Contribute to Cells of the Trophectoderm and Inner Cell Mass (ICM)

Figure 1F:
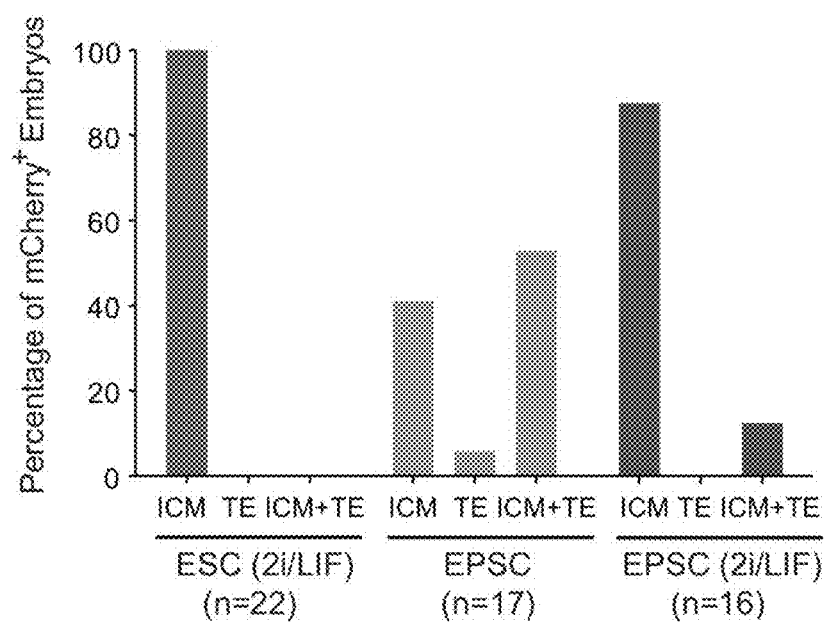

We next determined whether EPSCs were capable of participating in the development of pre-implantation embryos. We injected mCherry-labeled mouse EPSCs to morulas, which later developed to blastocysts in vitro. In 8 of 17 blastocysts injected with EPSCs, mCherry$^+$ cells were found in both the ICM and the TE (FIG. 1F), whereas none of the embryos (n=22) injected with 2i/LIF ESCs had donor cells in the TE. Interestingly, once EPSCs were returned to 2i/LIF for four passages, much lower contribution in the TE was observed (FIG. 1F), indicating that EPSCM is necessary to maintain the expanded potential.

We next investigated whether EPSCM was able to convert mouse epiblast stem cells (EpiSCs). EpiSCs are derived from early post-implantation embryos and are distinct from ESCs in culture properties, gene expression, pluripotency and epigenetic profiles. They are believed to exist at a primed pluripotent state (Nichols et al 2009; Tesar et al. 2007; Brons et al 2007). Unlike ESCs, EpiSCs rapidly succumbed or differentiated in EPSCM, indicating that conversion or reprogramming by EPSCM is only permissible to ground state ESCs.

Figure 2A:
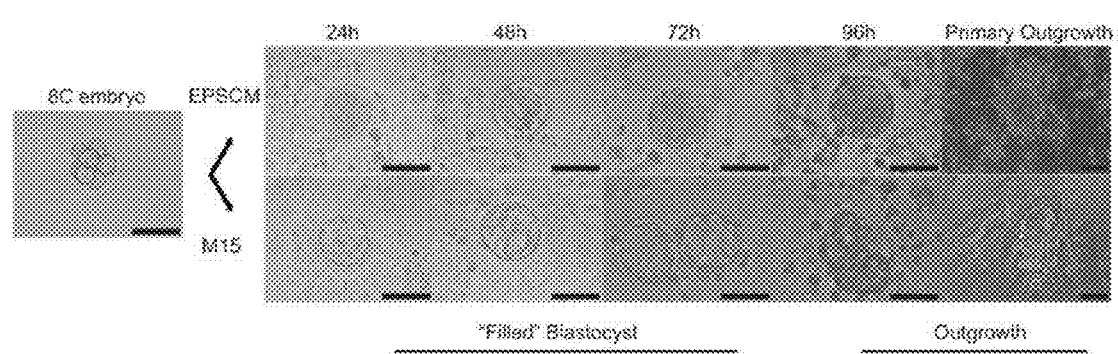
FIGS. 2A-2D shows the derivation of EPSC lines from preimplantation embryos or single blastomeres.

EPSC Lines can be Established from Preimplantation Embryos and from Reprogramming Somatic Cells We next explored deriving stable cell lines from pre-implantation blastomeres by EPSCM. We cultured 8C embryos in M15, 2i/LIF or EPSCM. On day four, 19 out of 42 embryos in M15 and 17 of 45 in EPSCM progressed to blastocysts, respectively (FIG. 2A), whereas only 5 of 54 in 2i/LIF did but these embryos eventually died. All blastocysts in M15 hatched by day 5. In striking contrast, the blastocoel in many blastocysts in EPSCM were obliterated and filled with cells, generating a structure reminiscent of a larger morula. We termed this structure a "filled" blastocyst (FIG. 2A and Fig. S2A). All the blastocysts in EPSCM developed to "filled" blastocysts by day 6, which eventually attached and hatched. Primary outgrowths appeared after day 10. Stable cell lines were established from 8C embryos in EPSCM on STO feeder cells with an efficiency of 20% (FIG. 2A).

To monitor the dynamic changes in pre-implantation embryos in EPSCM, we stained them with antibodies against Oct4 and Cdx2. From 4C to the blastocyst, the expression of Oct4 and Cdx2 in embryos in EPSCM was similar to those in M15, where Oct4 protein expression was first detected in 4C and Cdx2 protein in 8C embryos A. Ralston et al 2008 *Dev Biol* 313, 614; Dietrich, et al 2007). Oct4 expression was later restricted to the ICM, whereas Cdx2 in the trophectoderm. Nevertheless, we observed a gradual loss of both Oct4$^+$ and Cdx2$^+$ cells in the "filled" blastocysts. Eventually, the cells left in the embryos had large nuclei but most expressed neither Oct4 nor Cdx2, reminiscent of very early blastomeres (Macfarlan et al., *Nature* 487, 57 (2012). A couple of days later, a population of small Oct4$^+$ cells re-emerged at the periphery of the "filled" blastocysts. Once the embryos hatched, the cells in the early outgrowths expressed Oct4 and/or Cdx2 but subsequently became Oct4$^+$ only. To understand the cause of the loss of Oct4$^+$ and Cdx2$^+$ cells in the "filled" blastocysts, we examined proliferation and apoptosis by Ki67 or Caspase 3 staining. Many cells in embryos cultured in EPSCM were positive with Ki67 indicating they were still proliferating but apoptotic cell detected by Caspase 3 were clearly observed, particularly when the numbers of Oct4$^+$ and Cdx2$^+$ cells were decreased and before the small Oct4$^+$ cells re-emerged. These Oct4$^+$ cells did not directly arise from the blockade of the initial TE and ICM segregation. Instead, the emergence of Oct4$^+$ cells appears to be from a complex reprogramming process involving cell death and proliferation.

Figure 2B:
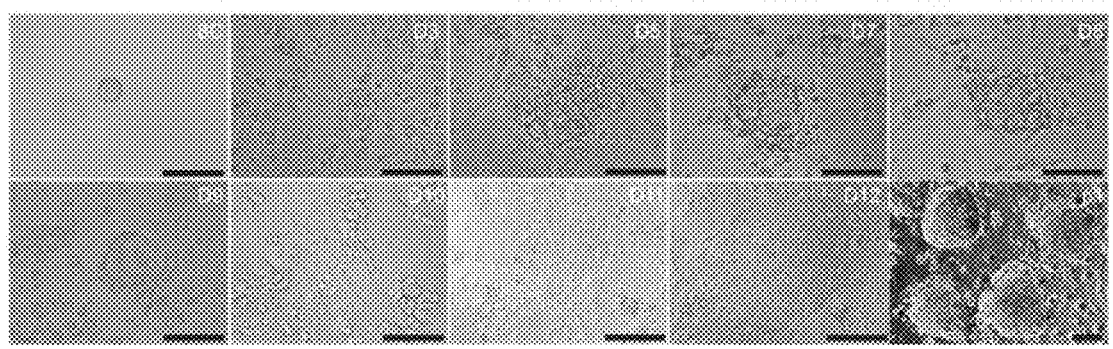
Figure 2C:
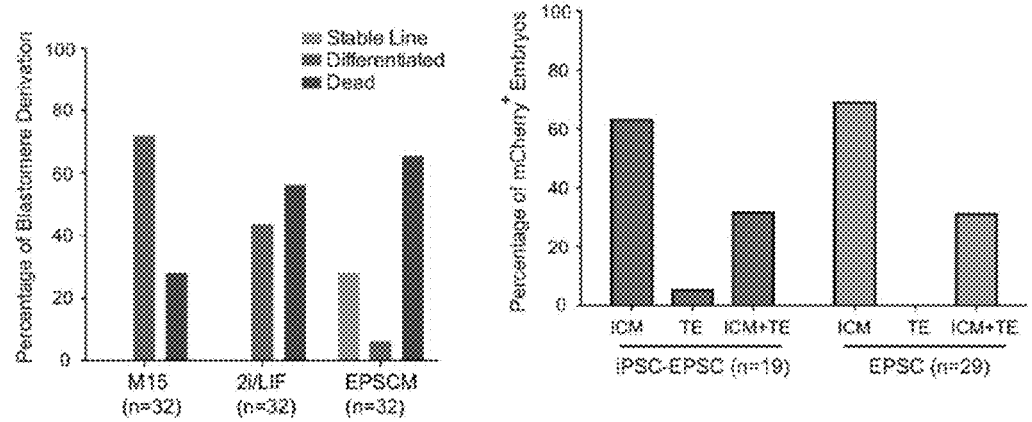

We next attempted to derive EPSC lines directly from single blastomeres of 8C embryos. Each blastomere was plated into a well of a 96-well plate with feeders (FIG. 2B). In the following days, in 9 out of 32 wells with EPSCM, blastomeres proliferated and formed a small patch of cells. These cells continued to proliferate to form large outgrowths on day 12 predominantly consisting of Oct4$^+$ cells with a few Cdx2$^+$ cells (FIG. 2B), while the other blastomeres became differentiated to trophoblast vesicles. By contrast, no outgrowths were obtained in either M15 (n=32) or 2i/LIF (n=32) on STO feeders, or from blastomeres cultured in feeder-free condition in any media (n=96) (FIG. 2C).

We subsequently characterized two lines derived de novo from preimplantation embryos in EPSCM: DR10-EPSCs and DR25-EPSCs. These EPSCs expressed pluripotency genes at levels comparable to standard ESCs, had the normal karyotype, were able to form mature teratomas and contributed to both somatic and the germline lineages in chimeras.

Figure 2D:
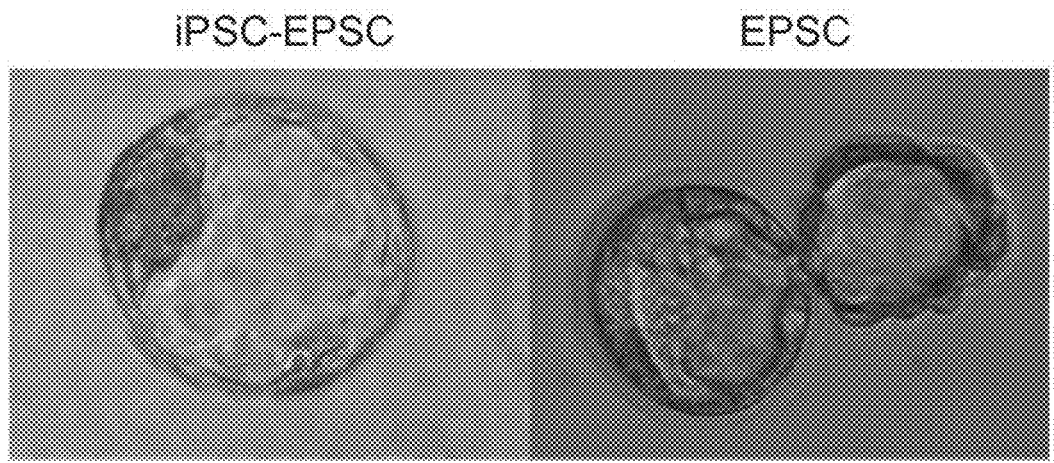

We next examined DNA demethylation status at the Cdx2 and Elf5 loci in DR10-EPSCs cultured either in EPSCM or M15 medium for three passages. DR10-EPSCs had the similar DNA demethylation pattern as in EPSCs from ESCs at the two loci but culturing these cells in M15 caused substantially increased methylation at both loci similar to in ESCs. Importantly, once injected to morulas, DR10-EPSCs contributed to the trophectoderm in the blastocysts (FIG. 2D).

We also asked whether we could obtain EPSCs directly from somatic cells (MEFs) by reprogramming them to iPS cells. We took advantage of the efficient six-factor reprogramming technology (Wang et al. 2011), and cultured primary iPS cell colonies directly in EPSCM. iPS cells cultured in EPSCM expressed comparable levels of core pluripotency factors and also contributed to both the ICM and the trophectoderm in the blastocyst developed from injected morulas (FIG. 2D).

EPSCs Contribute to Both the Embryo Proper and Placental Trophoblasts in Chimeras We proceeded to demonstrate the in vivo differentiation potency of EPSCs by injecting mCherry$^+$ EPSCs (DR10, DR25, AB2.2) and the control cells (AB2.2 in 2i/LIF or in M15) to pre-implantation embryos. We first injected EPSCs (DR10 and DR25) to morulas to generate chimeras, and examined their contribution to extraembryonic lineages in particular the placenta cells. In the 14.5 dpc chimera embryos, whole-mount fluorescence examination revealed extensive mCherry$^+$ donor cell contribution in the embryo proper and also some in the extra-embryonic tissues including the yolk sac and the placenta. FACS analysis of dissociated cells from the embryos and the placentas confirmed mCherry$^+$ cells in both lineages.

Figure 3A:
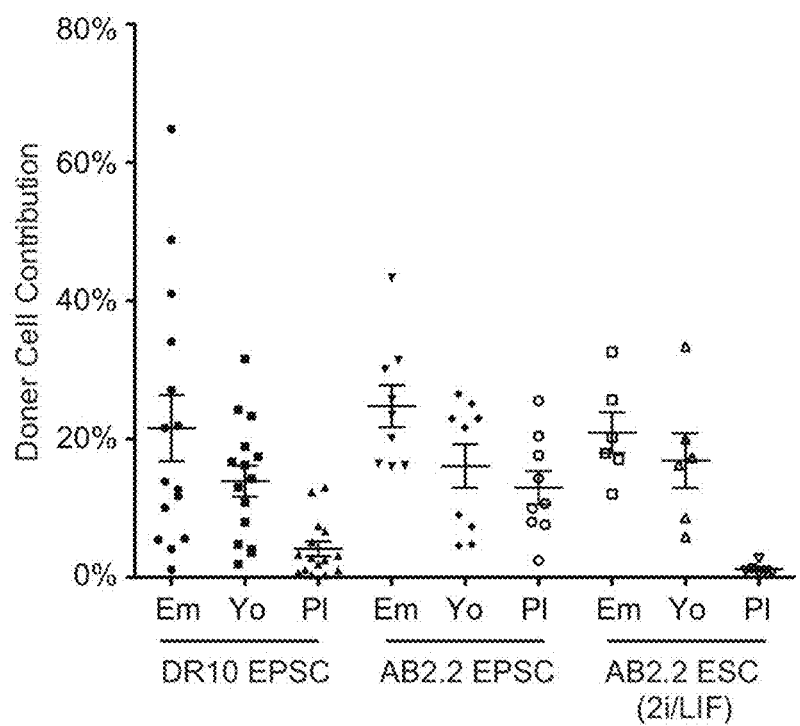
FIGS. 3A-3E shows the contribution of EPSCs and ESCs in chimera embryos. (A) Genotyping of donor cells in the embryo proper, the yolk sac and the placenta. The DR10-EPSCs have a Cre cassette at the Rosa26 locus so a Cre-specific taqman probe was used to determine the contribution of these cells. AB2.2-EPSCs or ESCs have a non-functional Neo cassette at the Hprt locus. A Neo-specific taqman probe was used to determine the contribution of these cells. Genomic DNA from parental DR10-EPSCs or AB2.2 ESCs was used as the positive controls in qPCR, and DNA from a wild type embryo was used as the negative control. The internal control is Tert TaqMan probe. Em: embryo proper; Yo: yolk sac; Pl: placenta. (B) Quantification of mCherry$^+$ donor cell contribution in chimeras detected by flow cytometry. Br: fetal brain; Li: fetal liver; Pl: placenta. (C) Sorting of mCherry$^+$ placenta cells from E14.5 chimeras. The contribution in the placenta from 2i/LIF ES cells was too low for sorting. (D) Expression of trophoblast genes in sorted mCherry$^+$ placenta cells from an EPSC chimera. Expression was normalized to fetal brain. mCherry$^-$ placenta cells were used as the control. Data are mean±s.d. (E) Detection of polyploidy placenta cells. A distinct population of 8N cells is present in both mCherry$^+$ and mCherry$^-$ placental cells from an AB2.2-EPSC chimera. Fetal brain cells were used as the control.
Figure 3B:
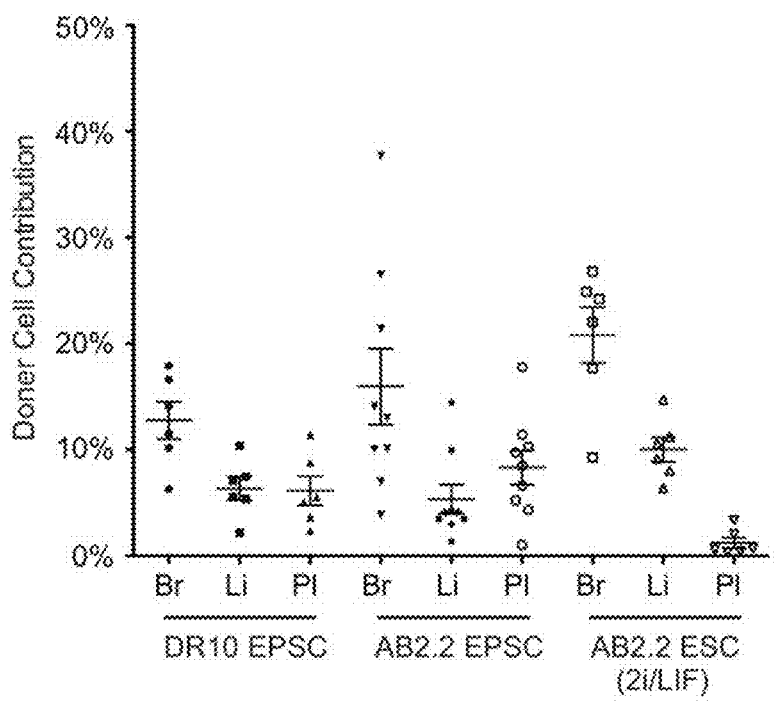

To independently confirm the result, we repeated the experiment at another transgenic facility (Cancer Research UK-Cambridge Institute) where 6-8 cells were injected to 8C host embryos for chimera production. mCherry$^+$ chimeras (14.5 dpc) were found in 13 out of 39 embryos for DR10-EPSCs, 9 out of 23 for DR25-EPSCs, 21 out of 38 for AB2.2-EPSCs and 16 out of 28 for AB2.2-2i/LIF ESCs. DNA genotyping again clearly confirmed contribution of EPSCs in the embryo proper and in the placenta (FIG. 3A). Flow cytometry analysis of dissociated single placental cells further confirmed the presence of descendants of mCherry$^+$ EPSCs besides their detection in the brain and the liver (FIG. 3B). By contrast, both DNA genotyping and FACS failed to detect obvious descendants of AB2.2-2i/LIF ESCs in the placenta (FIG. 3A, 3B).

Figure 3C:
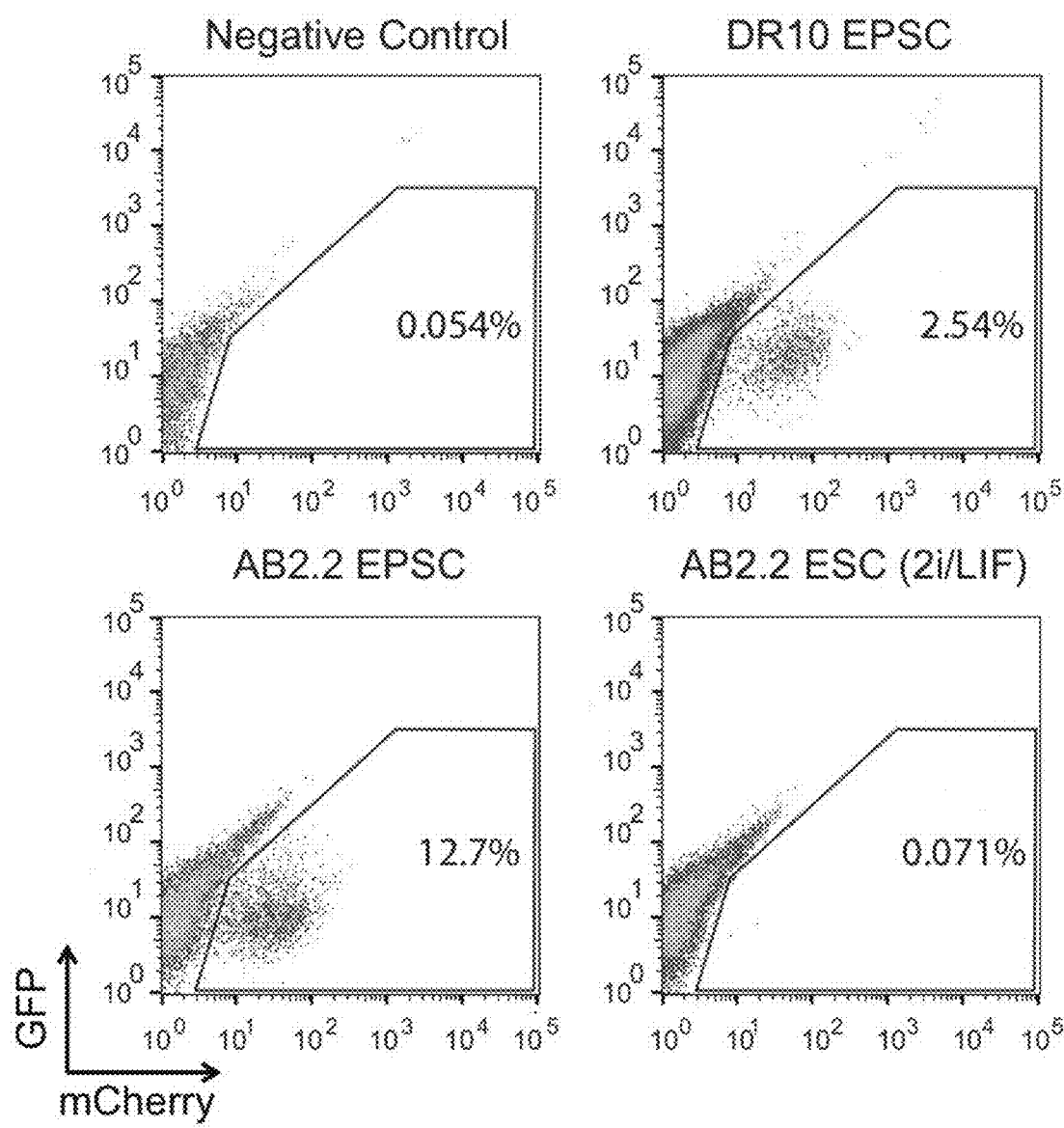
Figure 3D:
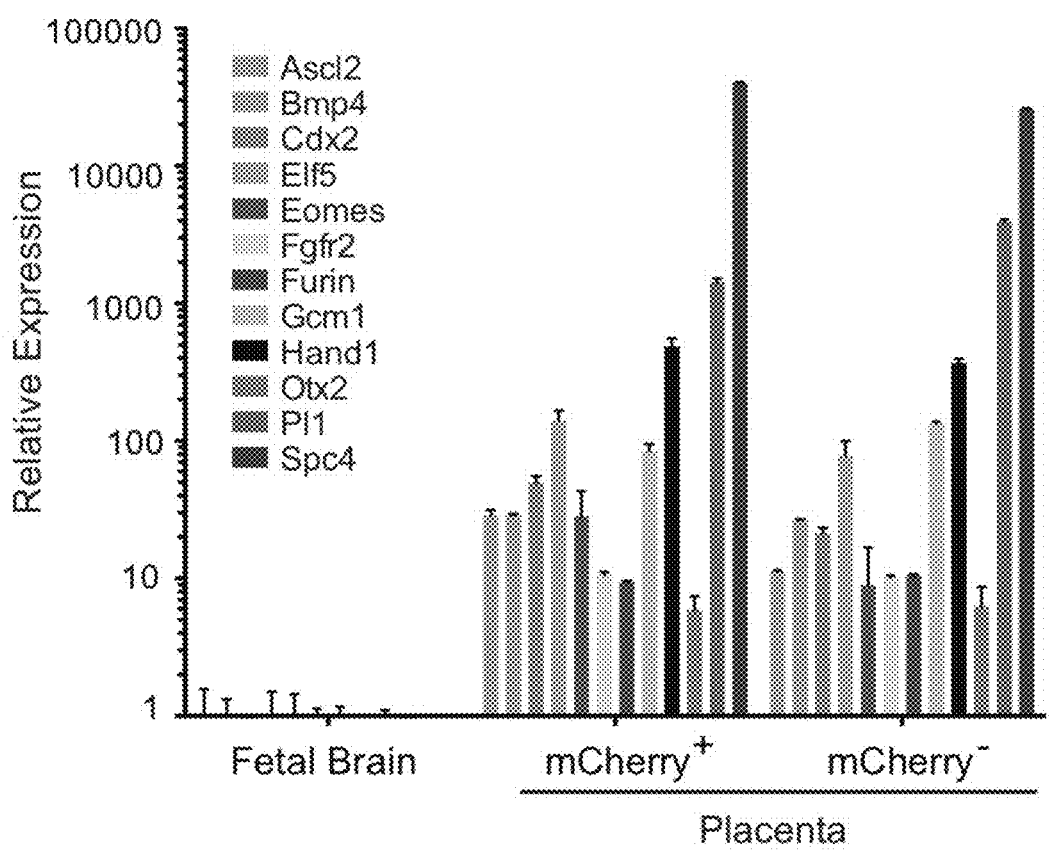
Figure 3E:
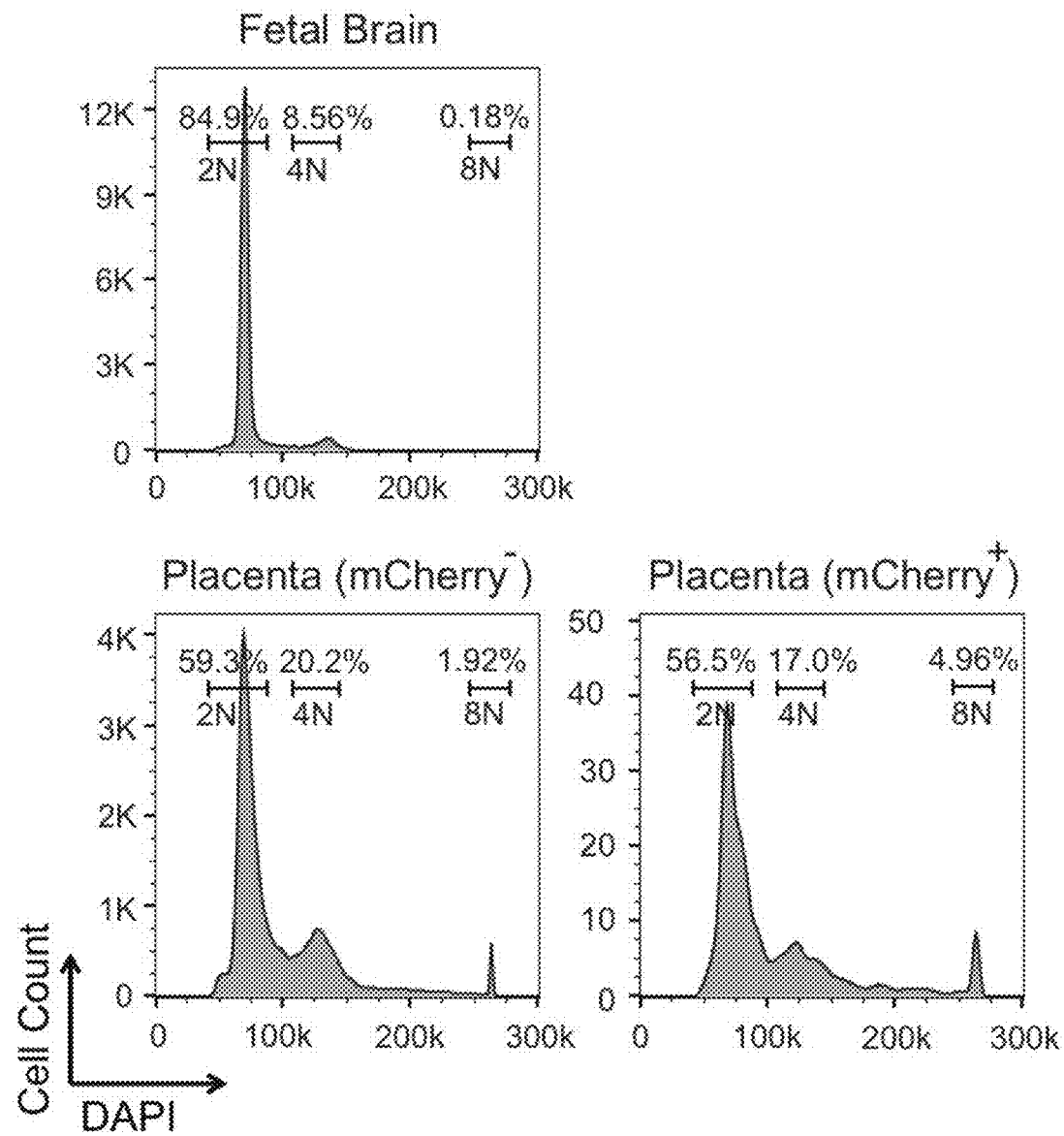

These mCherry placental cells were subsequently FACS-sorted for gene expression analysis (FIG. 3C). They expressed comparable levels of trophoblast genes, such as Asc12 (Mash2), Gcm1, PI-1, and Hand1, as in the mCherry$^-$ placental cells (FIG. 3E). By contrast, very few mCherry$^+$ placental cells were in the chimeras of AB2.2-2i/LIF ESCs, and we were unable to sort sufficient mCherry$^+$ placental for qRT-PCR (FIGS. 3C and 3D).

To further establish the identity of these mCherry$^+$ placental cells from EPSCs chimera, we stained the cells with DAPI for DNA content analysis. In flow cytometry trophoblasts could be detected as 4N, 8N and so on due to endoduplication during development and cell fusion (53).

We were able to unambiguously detect mCherry$^+$ 8N cells in the chimera placenta cells of EPSCs, similar to the flow pattern in mCherry$^-$ placental cells (FIG. 3E). At the cellular level, immune-staining of the placenta sections of EPSC chimeras clearly detected mCherry$^+$ multinucleated trophoblasts. Immunofluorescence staining of EPSC-derived cells in the placenta using a FITC conjugated antibody against mCherry revealed large mCherry$^+$ multinucleated trophoblasts in sections of the mouse placenta from a 14.5 dpc EPSC chimera. The large mCherry$^+$ trophoblast cells with low levels of background are only found in EPSC chimeras.

Figure 4A:
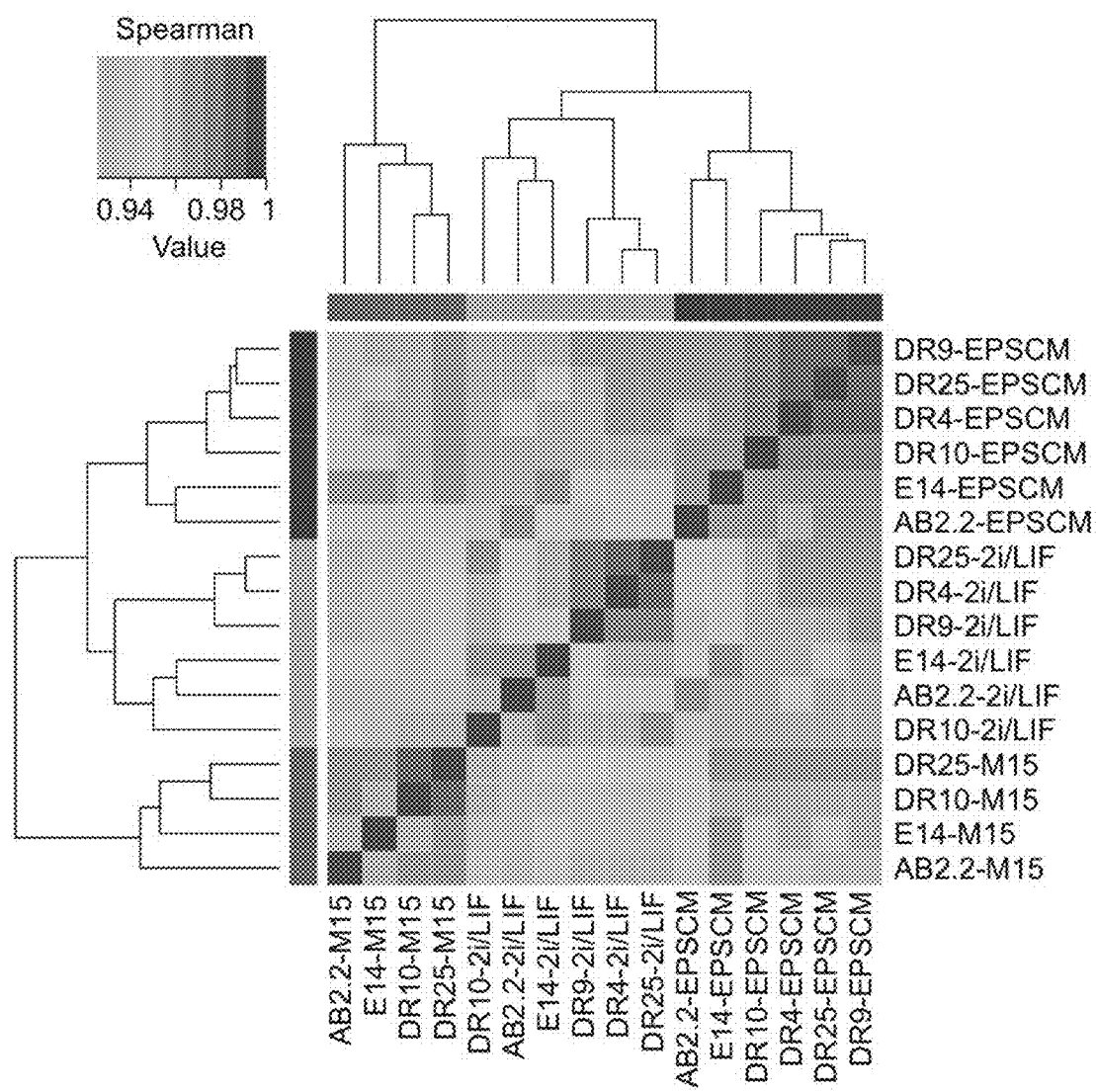
FIGS. 4A-4I shows that EPSCs have distinct transcriptome from that of standard ES cells.

The Transcriptome of EPSCs are Distinct from Standard ESCs but Share the Pluripotency Foundation with Ground-State ESCs To understand the molecular characteristics of EPSCs, we profiled the transcriptome of EPSCs and ESCs in different culture conditions by population RNA-seq. In hierarchical clustering, it is evident that the transcriptome of the cell lines segregated by their maintaining conditions irrespective of their original derivation methods and culture history (FIG. 4A). This suggests that the transcriptome of EPSCs and ESCs are convertible and consistent with the experimental results (FIG. 1). In addition, we profiled 84 individual EPSCs (DR10) to study the molecular heterogeneities of the EPSC culture.

Figure 4B:
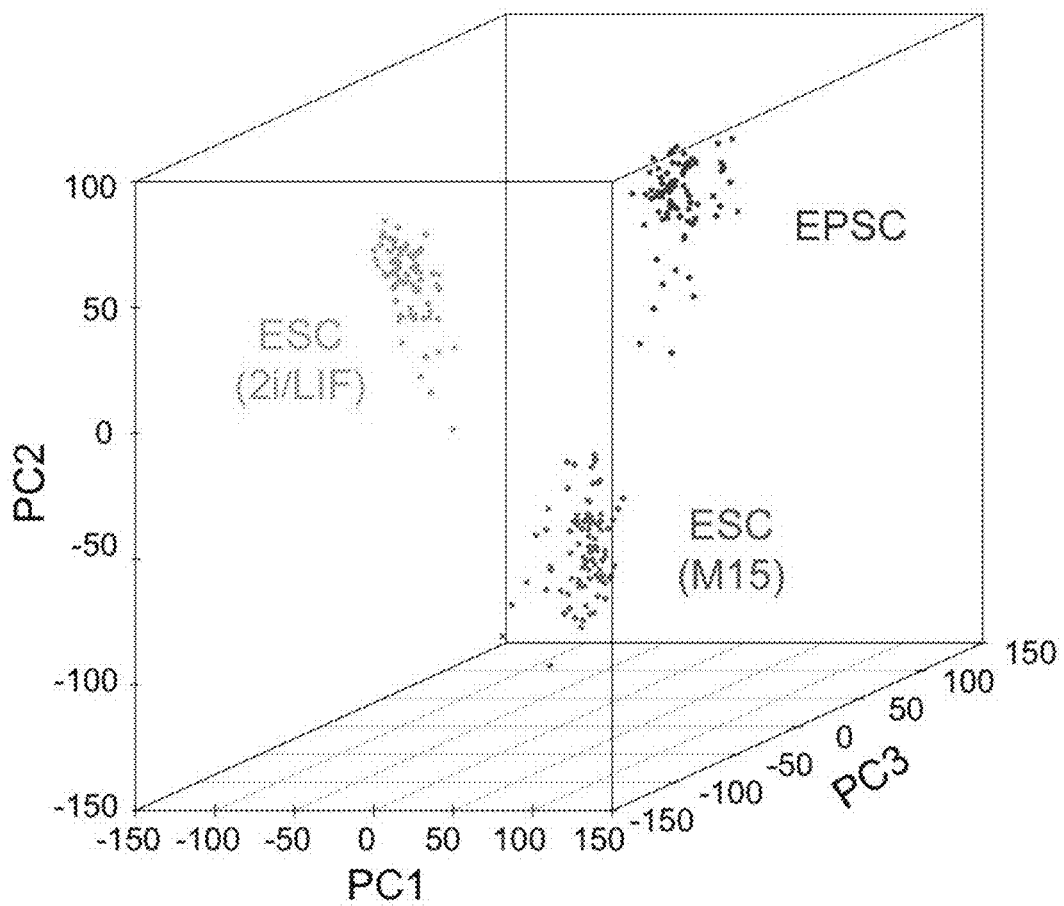

We compared our data with the single-cell RNA-seq dataset of 2i/LIF and M15 ESCs generated on the same platform with an ES cell line of similar background (Kolodziejczyk. et al manuscript under review). In principal component analysis (PCA), individual cell segregated by their culture conditions (FIG. 4B), demonstrating the global differences between EPSCs, 2i/LIF and M15 ESCs. We next performed differential gene expression analysis on the single-cell transcriptome of EPSCs and 2i/LIF ESCs. We detected 2843 and 1465 genes were up-regulated in EPSCs and 2i/LIF ESCs, respectively.

Figure 4C:
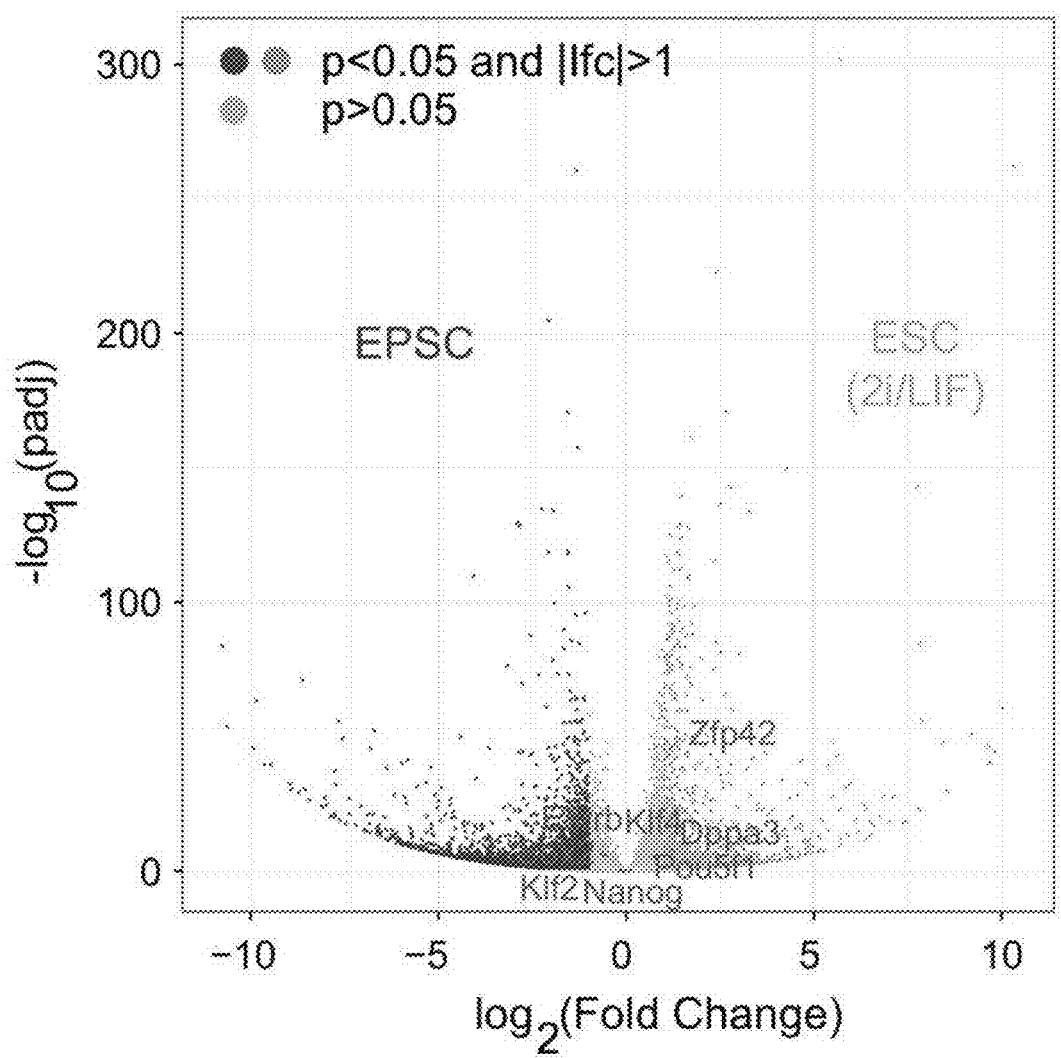

Gene ontology term enrichment analysis revealed that 2i/LIF ESCs were enriched in genes of metabolic process such as oxidative reduction and electron transport chain (Fig. S4A), concordant with previous reports (Marks et al. Cell 149, 590 (2012). By contrast, biological terms related to transcription regulation, embryonic developments in particular placental development were preferentially featured in EPSCs: Genes instrumental to placental development such as Eomes, Peg10, Asc12 (Mash2), Esx1 and Gata3 were differentially up-regulated in EPSCs. Lineage specific genes such as Gata4, Gata6, Pax6, Sox1 and Sox7 were also detected in EPSCs at low levels. In spite of the differences, the majority of pluripotency factors such as Oct4, Sox2, Nanog, Esrrb, Klf2 and Klf4 were not differentially expressed between EPSCs and 2i/LIF ESCs (FIG. 4C), consistent with the Rex1-GFP, Oct4-GFP reporter experiment and qRT-PCR data (FIG. 1B). This result suggests that the core pluripotency module is shared between EPSCs and ESCs.

Figure 4D:
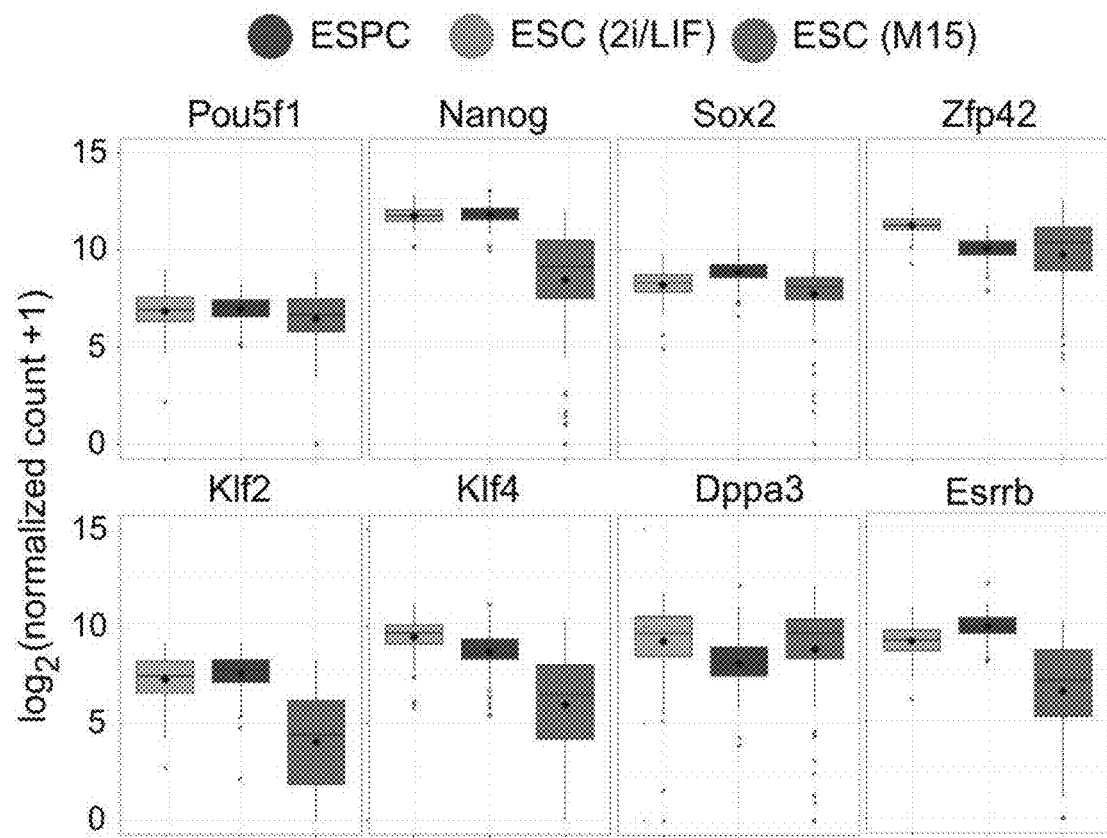
Figure 4E:
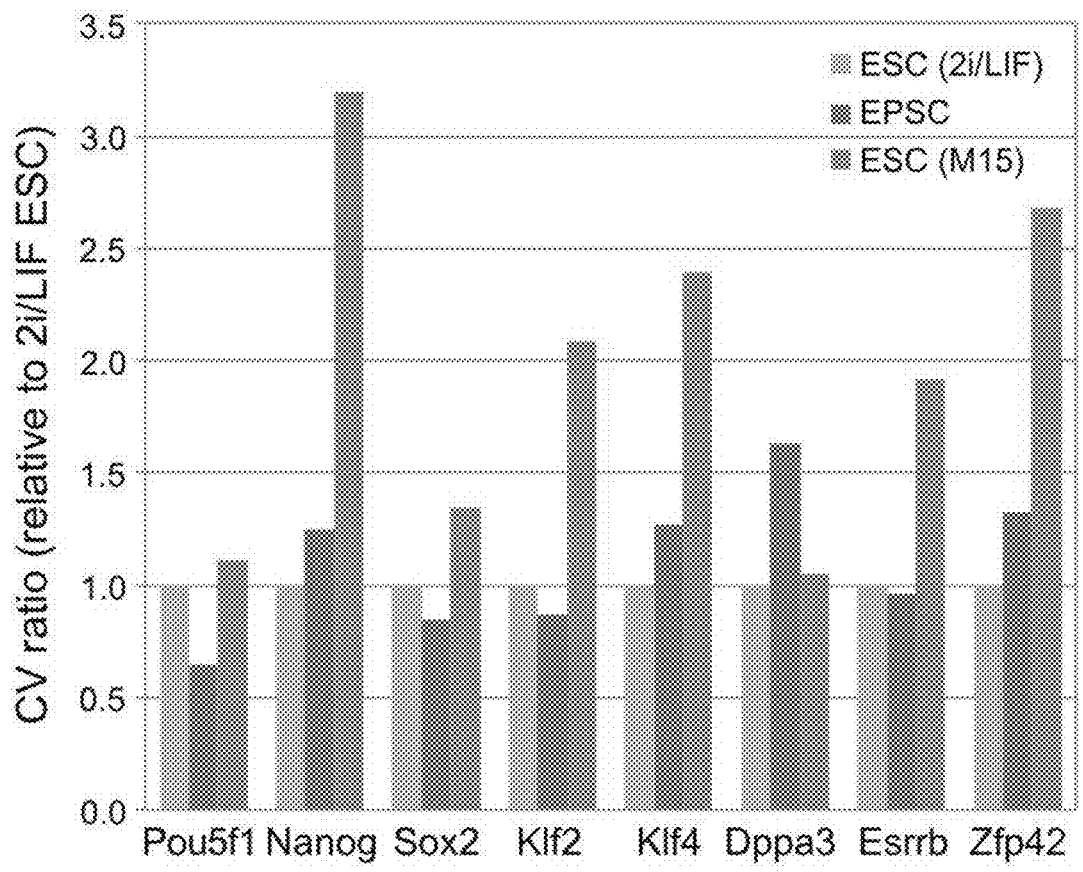
Figure 4F:
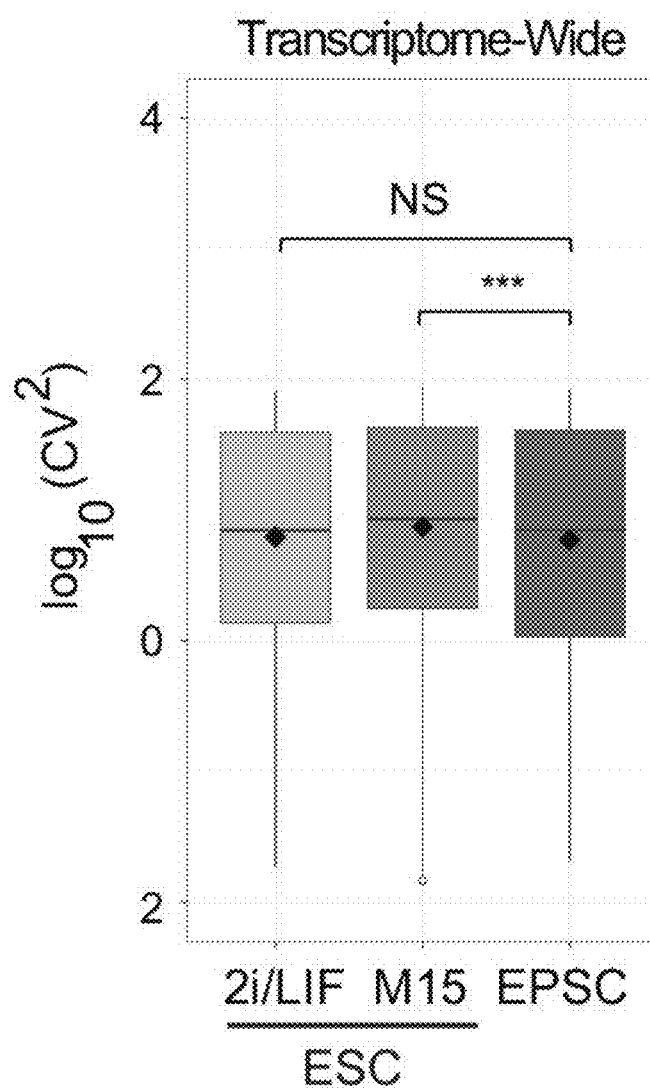

It has been previously shown that mouse ESCs cultured in serum containing media exist in a "metastable" state and showed fluctuation of the pluripotency state (Marks et al. Cell 149, 590. 2012). For instance, Nanog and Rex1 (Zfp42) are heterogeneously expressed in ESCs cultured in serum-containing medium, whereas their expression in 2i/LIF ESCs is more homogeneous. We compared single-cell expression variability of key pluripotency factors of EPSCs to 2i/LIF and M15 ESCs, and found that the expression variability (quantified by the coefficient of variation) of several pluripotency genes remained comparable in EPSCs and 2i/LIF ESCs, unlike the high variability observed in M15 ESCs (FIG. 4D, 4E). The global transcription variability of EPSCs is also similar to 2i/LIF ESCs, and significantly reduced from M15 ESCs (FIG. 4F). Therefore, we concluded that the cell state of EPSCs have similar transcriptome homogeneity to 2i/LIF ESCs and the low levels of lineage-specific genes expression observed in EPSCs is not due to in vitro differentiation or pluripotent state fluctuation.

Figure 4G:
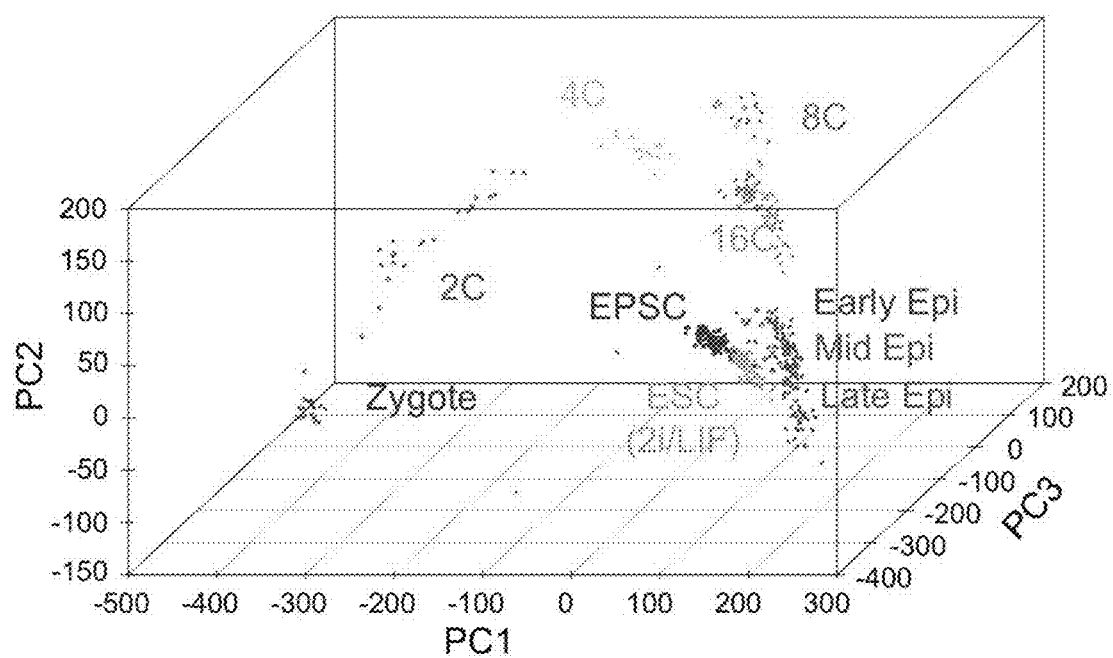
Figure 4H:
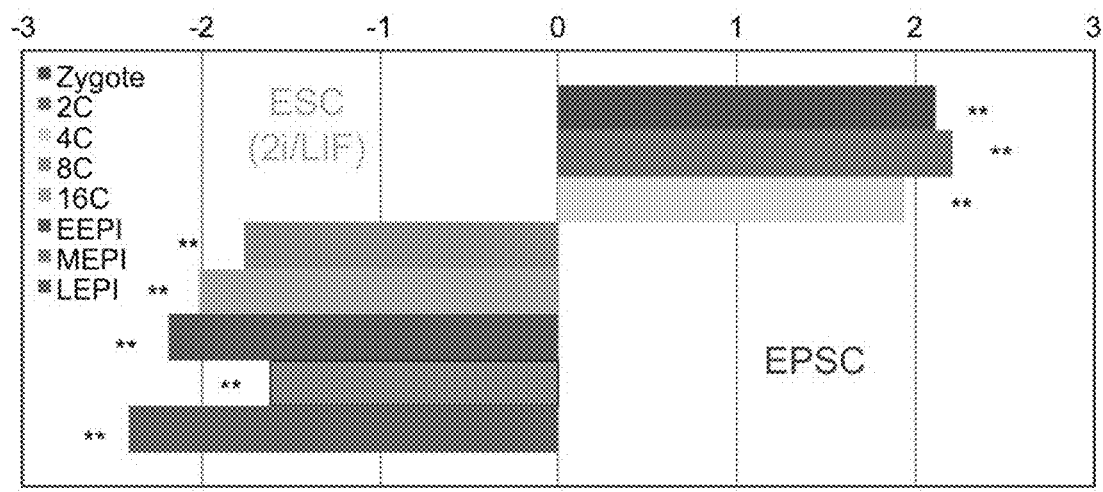

We next assessed the biological similarities of EPSCs to in vivo pre-implantation embryos. We retrieved the single-cell data from Deng et al (*Science* 343, 193. Jan. 10, 2014) for comparison. Although both EPSCs and 2i/LIF ESCs were mapped to the proximity of early epiblasts by the first three principal components (FIG. 4G), EPSCs showed separation from 2i/LIF ESCs in the first principal component (PC1) with scores in the range of 4C to 8C blastomere. To test if EPSCs have transcriptomic features of pre-implantation embryos compared to standard ESCs, we compiled the top 500 stage-specific genes of each embryonic stage from Deng et al and compared the expression of these signature gene sets in EPSCs and 2i/LIF ESCs by gene set enrichment analysis (GSEA). The result showed significantly higher enrichment of early pre-implantation (zygote, 2C and 4C) signature in EPSCs. Indeed, genes that have been previously suggested to be 4C-stage enriched, e.g. Npl, C130026I21Rik and E112 were significantly up-regulated in EPSCs.

Collectively, these data show that the transcriptome of EPSCs contain molecular features of early blastomeres.

Figure 4I:
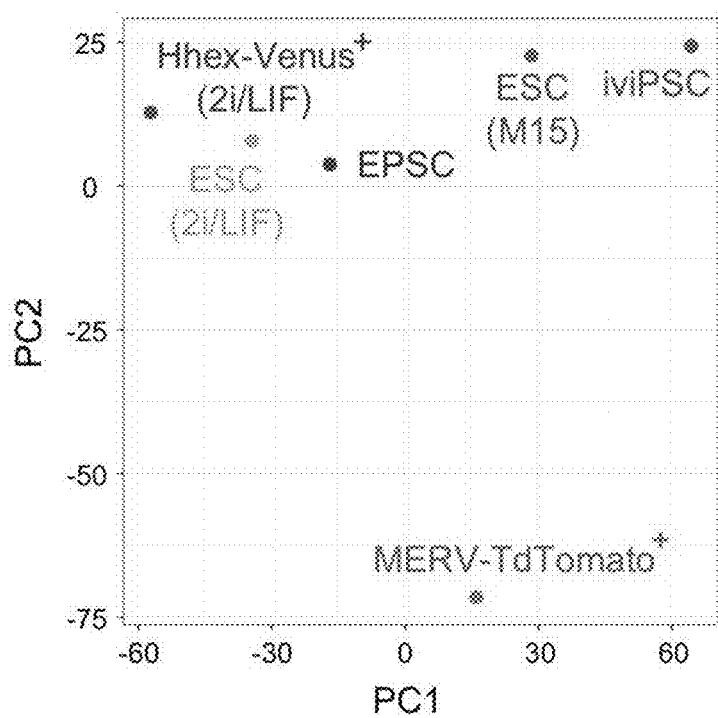

In additions, EPSCs were distinct from some of the recently reported rare totipotent-like ESCs subpopulations (MERV-TdTomato[+] and Hhex-Venus[+]) (Macfarlan et al. *Nature* 487, 57 (2012) and Morgani et al. *Cell Rep* 3, 1945 (2013)), or in vivo reprogrammed iPSCs (iviPSCs) in PCA by comparing the published population RNA-seq data (Abad et al. 2013) (FIG. 4I). Unlike MERV-TdTomato[+] 2C-like cells, we only observed mild up-regulation of endogenous retroviral transcripts in EPSCs.

Pervasive Bivalent Domains in EPSCs are Associated with Lineage and Placental Development Loci To further understand the epigenetic status of EPSCs, we profiled the genome-wide distribution of H3K4me3 and H3K27me3 modifications of two EPSC lines (DR25 & DR10) and compared the profiles with the published data of E14 ESCs in 2i/LIF (Marks et al 2012). As expected, H3K4me3 signal in EPSCs predominantly marked promoter regions and correlated with the level of active gene expression, while H3K27me3 peaks were distributed throughout the promoter and gene body and inversely correlated with gene expression. EPSCs contained more H3K4me3 (12698 vs 9487) and H3K27me3-associated genes (6969 vs 978) compared to 2i/LIF ESCs. There is significant overlap of H3K4me3-associated genes between the two cell types: 97.3% (9233/12698) of H3K4me3-associated genes in 2i/LIF ESCs were present in EPSCs. The higher number of H3K4me3 and H3K27me3 domains in EPSCs resulted in substantial increase of bivalent genes (4704 vs 189). The bivalent genes that were only found in EPSCs include notable gene families involved in embryonic development such as the Hox, Sox and Gata family and were enriched in biological process of somatic lineage and placental development. The prevalence of bivalent domains of EPSCs in these loci provides a molecular basis for the low expression of lineage specific genes detected in single-cell RNA-seq. Finally, we found that genes annotated in "Placenta development" have higher H3K4me3 signals in EPSCs compared to 2i/LIF ESCs, consistent with the gene ontology term enrichment analysis. On the other hand, the H3K4me3 and H3K27me3 signal of EPSCs in key pluripotency loci such as Pou5f1, Sox2 and Nanog were highly similar to 2i/LIF ESCs.

A Single EPSC Contributes to Both the Embryo Proper and Trophoblasts

The in vitro, in vivo experiments and epigenetic profiling aforementioned revealed the functions and molecular features of EPSCs. Importantly, single-cell RNA-seq revealed that EPSC cultures are stable and have similar molecular homogeneity as to 2i/LIF ESCs. However, it is still possible that current genomic analysis resolution may not be able to identify distinct subpopulations of EPSCs that independently contribute to either embryonic or extraembryonic lineages.

Figure 5A:
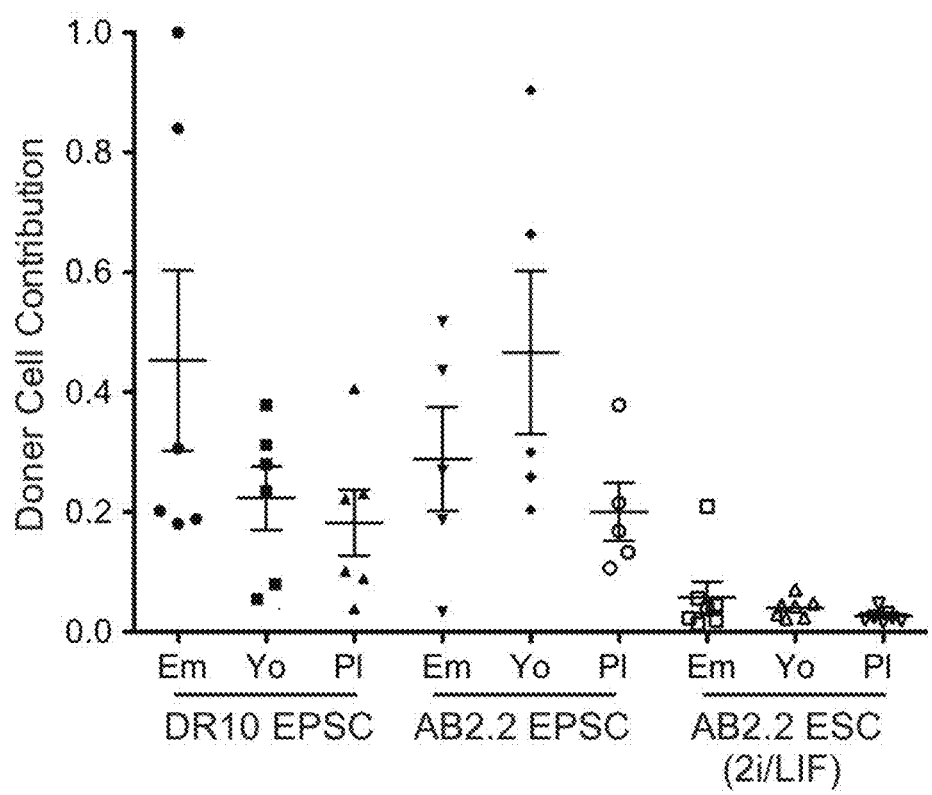
FIGS. 5A-5D show the contribution of a single EPSC in 14.5 dpc chimeras.
Figure 5B:
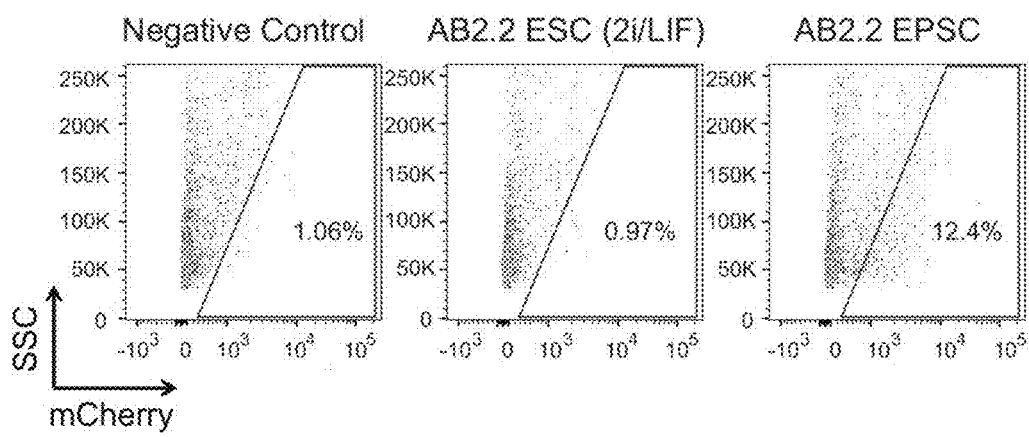
Figure 5C:
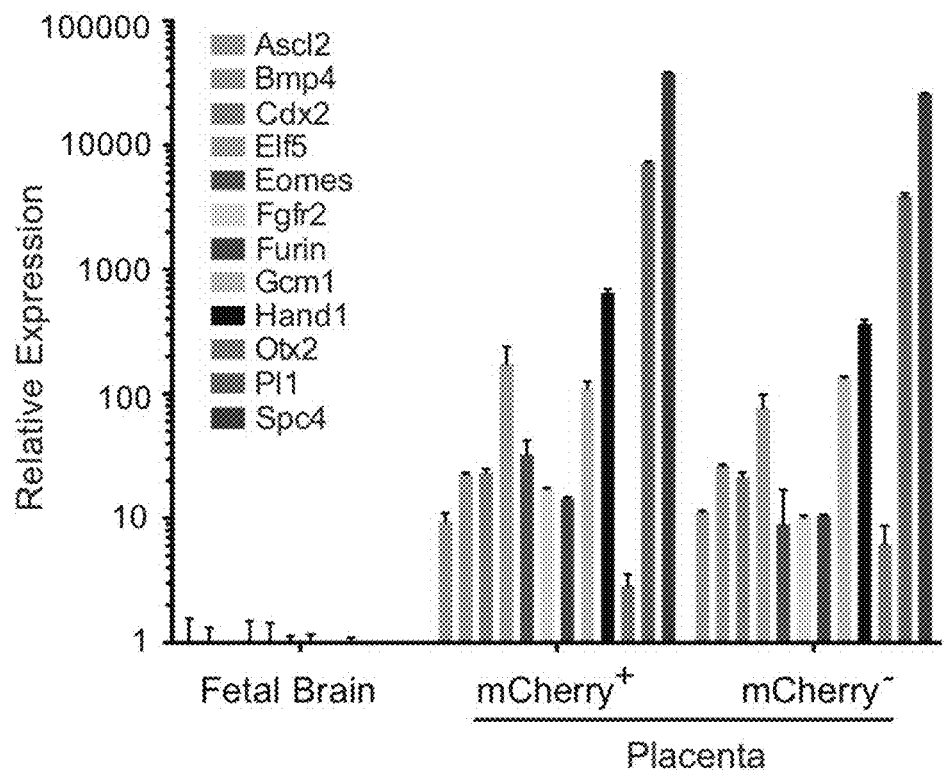
Figure 5D:
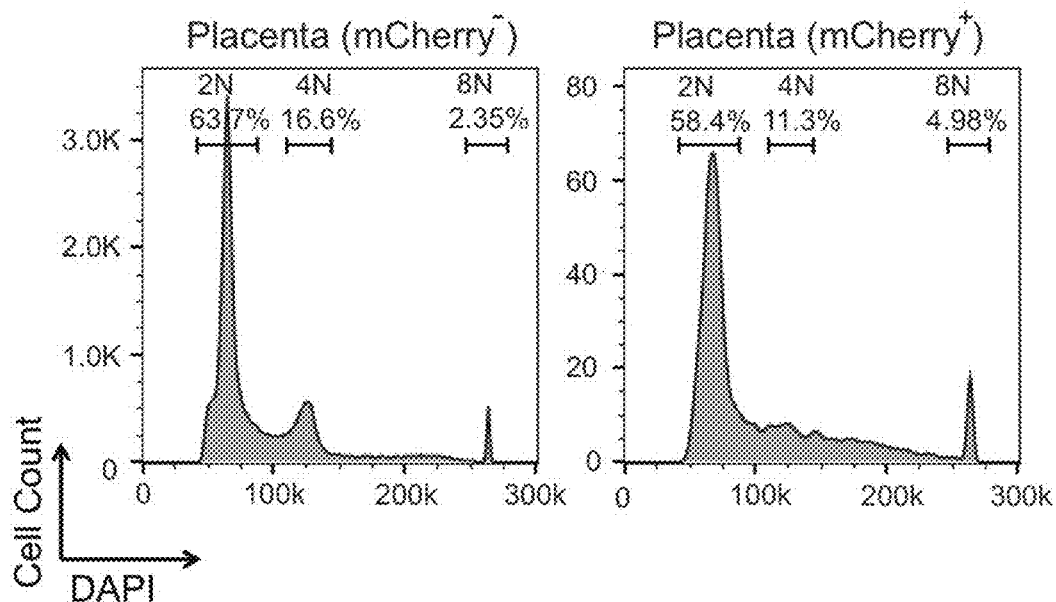

To formally exclude this possibility and to conclusively demonstrate the potency of EPSCs, we determined whether a single EPSC, once injected to an 8C embryo, was able to contribute to both lineages. To this end, each 8C host embryo was injected with a single EPSC (DR10, DR25 and AB2.2) or with a control ES cell (AB2.2-2i/LIF) for chimera production. Embryos were harvested at 14.5 dpc. Under fluorescence microscope, mCherry[+] cell contribution was found in 7 out of 85 embryos for DR10 cells, 8 out of 77 for DR25 cells, 7 of 51 for AB2.2-EPSCs, and 9 for 76 for AB2.2-2i/LIF cells. DNA genotyping showed descendants of EPSCs in the embryo and in the placenta in mCherry[+] chimeras (FIG. 5A). Flow sorted Cherry[+] placental cells from EPSC chimeras (FIG. 5B) were analysed for gene expression. Again, genes expected to be expressed in trophoblasts were clearly detected in these cells in qRT-PCR, comparable to in the host cell-derived mCherry[+] placental cells (FIG. 5C). Furthermore, FACS analysis of the mCherry[+] placental cells detected 8N trophoblasts, similar to the mCherry placental cells (FIG. 5D). In some embryos, mCherry[+] EPSCs contributed up to 40% of placental cells in DNA genotyping but the embryos were morphologically normal, indicating that placental cells from EPSCs were likely functional in supporting normal embryo development, which warrants future investigation. By contrast, AB2.2-2i/LIF ESCs in chimeras contributed poorly in the embryo and little to the placenta as revealed by genotyping, and FACS analysis failed to detect enough numbers of mCherry[+] placental cells for sorting or for 8N trophoblast analysis in these chimeras.

We also injected a single AB2.2 cells cultured in M15 medium to an 8C host embryo but did not recover any chimeras (0/18). This result reflects the fact that in practice it usually requires injecting 6-8 standard ESCs to an 8C host embryo for efficient chimera production.

We have demonstrated that stable stem cell lines with expanded potential could be derived from individual blastomeres of preimplantation embryos and from reprogramming mouse ESCs or somatic cells in EPSCM. Functionally, a single EPSC contributes to both trophoblast and embryonic lineages in chimeras. The development of preimplantation embryos cultured in EPSCM is significantly altered and the derivation of EPSCs is accompanied by cell proliferation and apoptosis. Expression of Cdx2 and Oct4 in the blastomeres is transiently lost with Oct4[+] cells eventually emerging to derive the stable EPSC lines. This double negative state is reminiscent of 2-cell stage blastomeres.

Established EPSC lines are functionally and molecularly similar, independent of their derivation origins. Molecular characterization reveals that EPSCs have distinct transcriptome and histone methylation patterns compared to ESCs, and exhibit partial DNA demethylation at the Cdx2 and Elf5 loci. The transcriptome of EPSCs is also enriched with molecular signature of early blastomeres, although remains distinct from blastomeres. EPSCM is necessary to maintain the expanded potential since EPSCs cultured in standard ES medium rapidly lose their capacity to contribute to the TE and restore DNA methylation at the Cdx2 and Elf5 loci. Intriguingly, EPSCs express levels of core pluripotency factors (Oct4, Sox2 and Nanog) similar to pluripotent ESCs. This suggests that these genes constitute the molecular foundation of pluripotency, and that additional unidentified factor(s) induced by EPSCM confers the expanded potential of EPSCs. Compared to ESCs, EPSCs contain increased bivalent domains at genetic loci of lineage specifiers. It has been suggested that "promiscuous" transcription at bivalent loci is a hallmark of "metastable" ESCs cultured in serum-containing media and these genes are poised for activation upon differentiation induction (Marks et al 2012, Bernstein et al 2006. Cell 125,315) On the contrary, bivalent domains are significantly reduced accompanied by stable expression of Nanog and Rex1 in ESCs cultured in 2i/LIF (Marks et al 2012). In spite of the increased bivalent domains in EPSCs, single-cell RNA-seq shows that the transcriptome of EPSCs has reduced expression variation compared to ESCs maintained in serum-containing media (M15) and the expression of Nanog and Rex1 are inherently stable. This unique stability could be contributed by the simultaneous modulation of multiple signaling pathways in EPSCM.

Our transcriptome data suggests that EPSCs are categorically different from the rare 2C-like and Hhex$^+$ ESCs which were reported to transiently exist in standard ESC culture. EPSCs are also transcriptionally different to in vivo reprogrammed iPSCs which have been shown to be highly similar to ESCs transcriptionally but express several morula stage genes. It remains unclear if the expanded potential observed in the in vivo iPSCs is contributed by similar rare ESC subpopulations in culture. Importantly, EPSCs are maintained in stable cultures and they demonstrate functional homogeneity of expanded potential in the single-cell injection experiment, refuting the existence of rare privileged subpopulations.

Human ESCs can Survive in EPSCM and Proliferate to EPSCs.

We also investigated whether human ESCs could survive and proliferate in EPSCM. H1 hESCs were maintained in standard FGF2 containing media on feeders. H1 cells survived culture in EPSCM and morphologically distinct 3-dimensional colonies emerged within one passage. Continued culture allowed establishment of a stable line which we called H1-EPSCs.

Figure 6A:
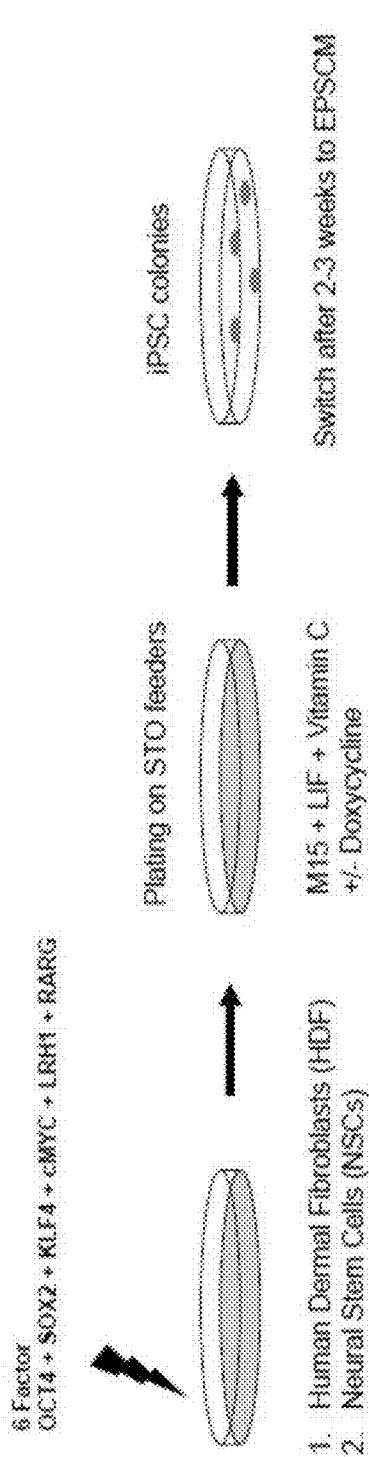
FIGS. 6A-6C show a scheme for reprogramming somatic cells into iPSCs.
Figure 6C:
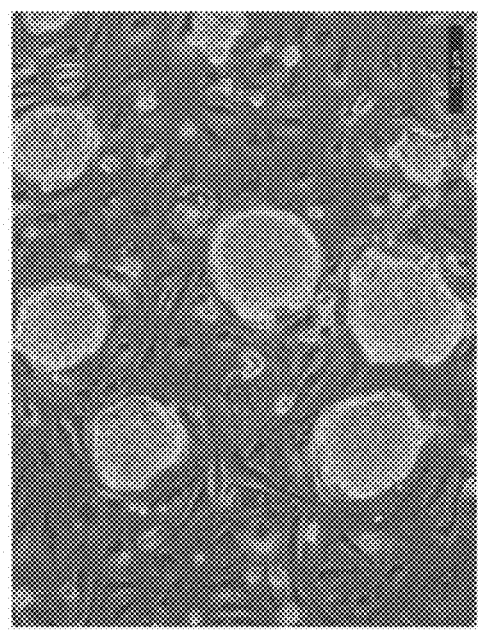
Figure 6B:
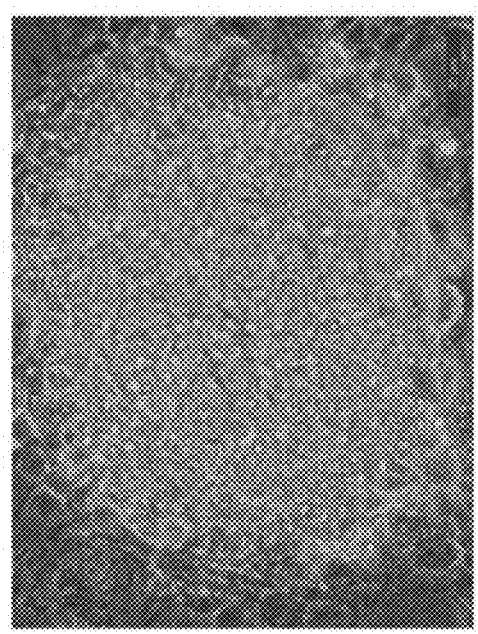

Human iPSC lines were also produced from human neural stem cells, and from human fetal or adult skin fibroblast cells using the six-factor reprogramming technology described in Wang et al (2011) and cultured for 2-3 weeks on feeders. The resulting iPSCs were switched to EPSCM and transgene free stable lines were established (EPSC-iPSCs). (FIG. 6). Stable human EPSC-iPSC lines have been passaged for over 30 passages in EPSCM.

In addition to the six-factor reprogramming described above, human iPSC lines were also produced from human fibroblast cells by expressing the four Yamanaka factors: Oct3/4, Sox2, Klf4, c-Myc (Takahashi et al (2006)). The primary iPSC colonies were cultured in EPSCM and the survival colonies were picked for expansion and line establishment.

Monitoring the Naive State of Human EPSCs

Figure 7A:
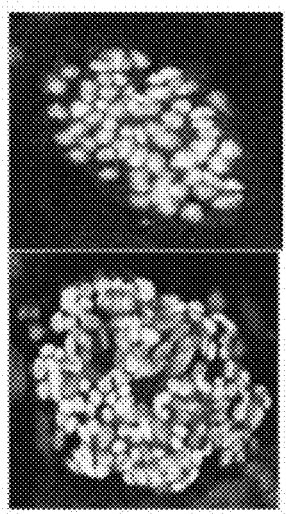
FIGS. 7A-7B show that EPSCs express key pluripotency markers at both the RNA (FIG. 7A) and the protein level (FIG. 7B). Left to right the markers measured are hOCT4, hSOX2, hNANOG and hREX1. H1 hESC (human embryonic stem cell) is standard FGF-cultured ESC. Human dermal fibroblast is the negative control and HiPS70 are EPSCs which were generated from iPSCs.
Figure 7B:
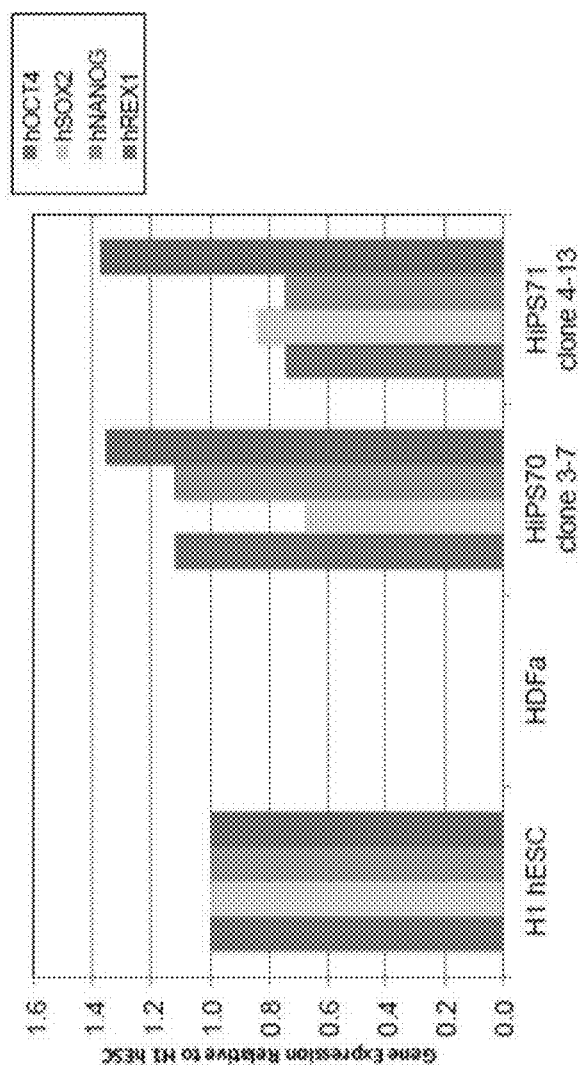
Figure 8:
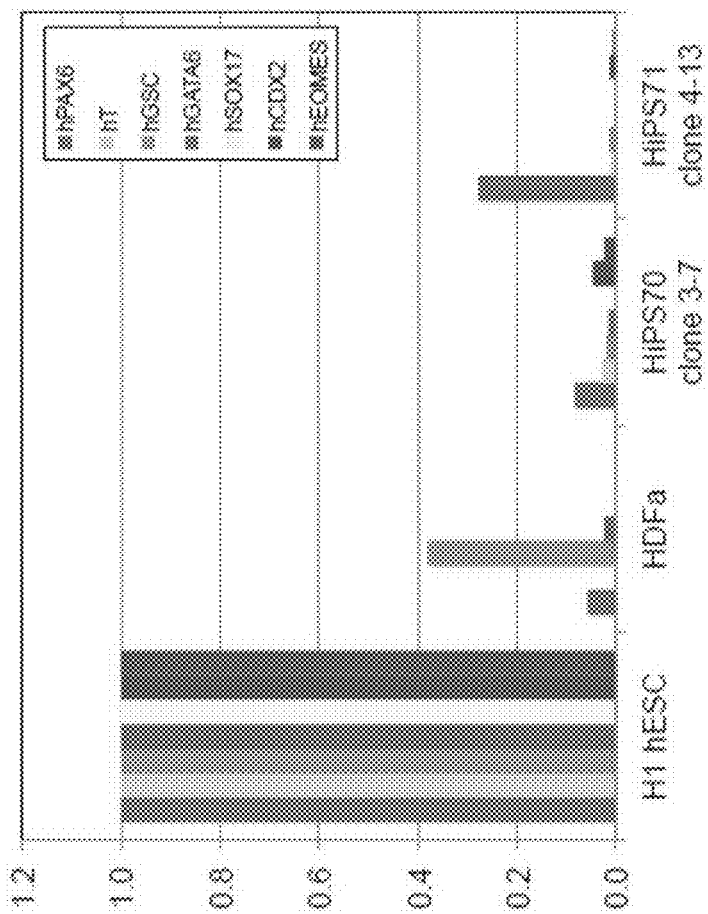
FIG. 8 shows that, in contrast to H1 hESCs, the h-EPSCs (HiPS70 and HiPS71) have minimal expression of lineage differentiation markers. This result is similar to that observed in mouse EPSCs. Left to right the markers measured are hPAX6, hT, hGSC, hGATA6, hSOX17, hCDX2, hEOMES.

We made several reporter EPSC lines that have a GFP or mCherry expression cassette at loci including Oct4, Sox2 and ROSA26. Analysis of Oct4-GFP EPSCs demonstrated that the majority of the cells were GFP+. Importantly, these reporter cells provide a convenient way to assess the culture condition. For example, for EPSCM which comprises a DMEM/F12 basal medium supplemented with knockout serum replacement (KSR) we found that each and every of the six small molecule chemical inhibitors in EPSCM is necessary to maintain the Oct4-GFP$^+$ cell population. However, we have also observed cases where EPSCM supplemented with fewer than six inhibitors has been able to obtain EPSCs. For example, where the EPSCM is supplemented with a chemically defined basal medium, such as Albumax II, it has been observed that fewer than six inhibitors are required obtain EPSCs. For example, human EPSCs have been obtained using an Albumax-based medium which is supplemented with an Src Kinase family (SFK) inhibitor a GSK3 inhibitor and a Wnt inhibitor. Without being bound by theory it is believed that because KSR contains many cytokines and proteins at unknown concentration, some of the inhibitors we used might be interacting with the components of KSR, instead of working directly on EPSCs. Therefore, it appears that a chemically defined EPSCM may require fewer inhibitors. Human EPSCs were also found to express key pluripotency marker genes at levels comparable to the standard human ES cells (FIG. 7). They also expressed lower levels of lineage differentiation genes such as PAX6, T or SOX17 (FIG. 8). They also expressed much lower levels of HLA complex genes compared to standard H1 cells.

Human EPSCs are Genetically Stable.

Human EPSCs generated from both iPSCs and ESCs by culturing in EPSCM were genetically stable as measured by karyotype analysis and whole genome array CGH. We have karyotyped several EPSC lines, H1 converted and iPSC lines after at least 15 to 30 passages. No abnormality was detected on DAPI banding or M-FISH. Higher resolution genotyping using CGH-array further confirmed the genome integrity of EPSCs.

Human EPSCs can Differentiate to all Three Germ Layers.

EPSCs can efficiently differentiate to cells of all three germ layers and form mature teratomas in immune-compromised mice. Human EPSCs were injected into the dorsal flanks of NSG mice. Within 2 months teratomas became evident which contained derivatives of the three germ layers and also demonstrated maturity with melanin expression.

Differentiation of EPSCs In Vitro to Functional Neurons.

EPSCs were differentiated to terminal neuroglial cell types using a monolayer differentiation protocol described below, containing N2B27, FGF2 and dorsomorphin dihydrochlorde on extracellular matrix IHC confirmed the presence of mature neuronal markers NeuN and synaptophysin. These neurons were found to be functionally mature demonstrating electrophysiological competence.

Differentiation of EPSCs In Vitro to Pancreatic Cell Types.

Using a monolayer differentiation protocol described in Cho C H, et al 2012, human EPSCs were successfully differentiated to pancreatic progenitors and terminally differentiated pancreatic cell types including insulin-secreting cells and glucagon secreting alpha cells.

Differentiation of EPSCs In Vitro to T Cells.

Using a T-cell generation protocol described in Themeli M, et al 2013, human EPSCs were successfully differentiated in vitro to T-cells.

Production of Primordial Germ Cell-Like Cells.

Our data also show that primordial germ cell-like cells can be produced in embryoid bodies from human EPSCs.

PGC Induction was assessed by serial FACS analysis. Successful differentiation was determined based on the emergence of a KIT+SSEA1+TRA1-81+ positive population. PGC transcription factors Oct4, Stella, PRDM1 (Blimp1), VASA and DAZL expression were checked using Taqman qPCR probes. At day 8 of differentiation, 35% of the population was KIT+ SSEA1+ and highly expressed TRA1-81. qPCR demonstrated significant expression of PCG transcription factors Stella and PRDM1. (FIG. 10) The protocol used is modified from Duggal G, et al 2013 as described below).

These results are notable because it is known that differentiation of standard human ES cells or iPSCs to primordial germ cells is challenging and inefficient.

Female EPSCs Show X Chromosome Reactivation.

X chromosome reactivation is a functional characteristic of 'naïve'-type ES cells. X chromosome reactivation in female cells is found during early embryo development in the human. Using single cell RNA FISH, female EPSCs were found to have X chromosome reactivation with loss of the repressive X-inactive specific transcript (XIST) and expression of the long noncoding RNA, XACT which coats the active X chromosome in pluripotent cells. Further experimental validation was obtained by checking the expression of a specific X-linked gene (HPRT1). In EPSCs, as there are two active X chromosomes, then two HPRT1 signals were observed. Following embryoid body differentiation, reversibility was observed with re-emergence of the repressive XIST signal and loss of one HPRT1 signal.

In female iPSC-EPSCs, XIST expression is not detected in over 90% of cells, whereas XACT, which marks active X chromosome, is expressed in over 90% of cells by RNA-FISH. Other X-linked genes such as HPRT were found to be expressed biallelically in female EPSCs detected by RNA-FISH. However, once female EPSCs are differentiated, one X chromosome is inactivated. X chromosome reactivation in female EPSCs was also supported by genome-wide RNA-Seq analysis which shows X chromosome reactivation in female EPSCs. On the other hand, X linked genes were found to be down-regulated during differentiation at the pan-X chromosome level.

Standard human ES cells, such as H1 ES cells, often have abnormal expression of imprinting genes. However, EPSCs (HiPS70 and HiPS71) were found to have normal expression of imprinting genes examined (hMEG3, hMEG8, hDLK1 and hDIO3) compared to human fibroblasts.

Human EPSCs can Differentiate to Trophoblast-Like Cells.

Mouse EPSCs are distinct from mouse ES cells in that they can differentiate to trophoblasts both in vitro and in vivo. Standard human ES cells have also been shown to be able to differentiate to trophoblasts in vitro, although it is under debate whether these in vitro differentiated trophoblasts are bona fide trophoblasts.

Figure 9:
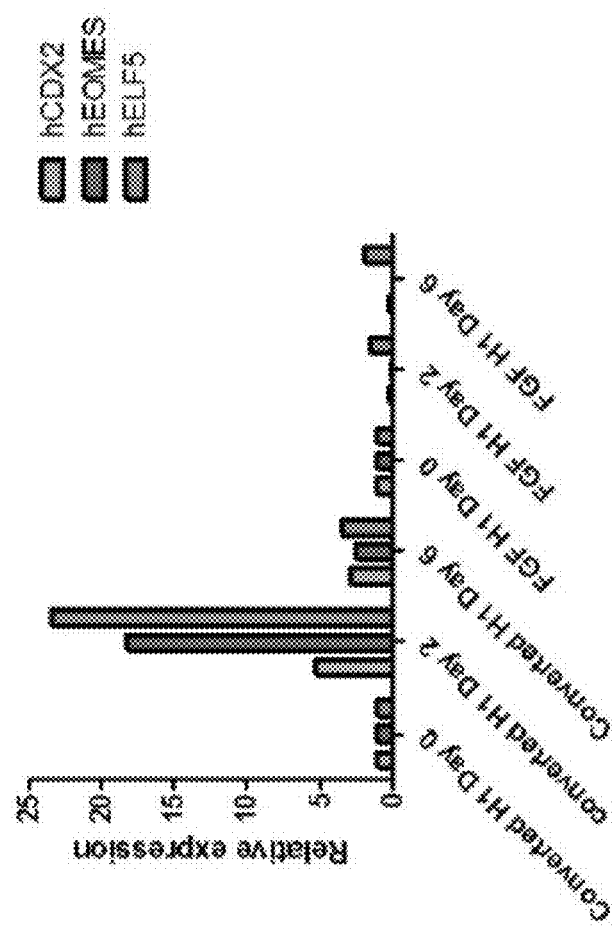
FIG. 9 shows that following a trophoblast induction protocol, EPSCs show significant upregulation of trophoblast-specific genes. From left to right the genes measured are hCDX2, hEOMES and hELF5.
Figure 10A:
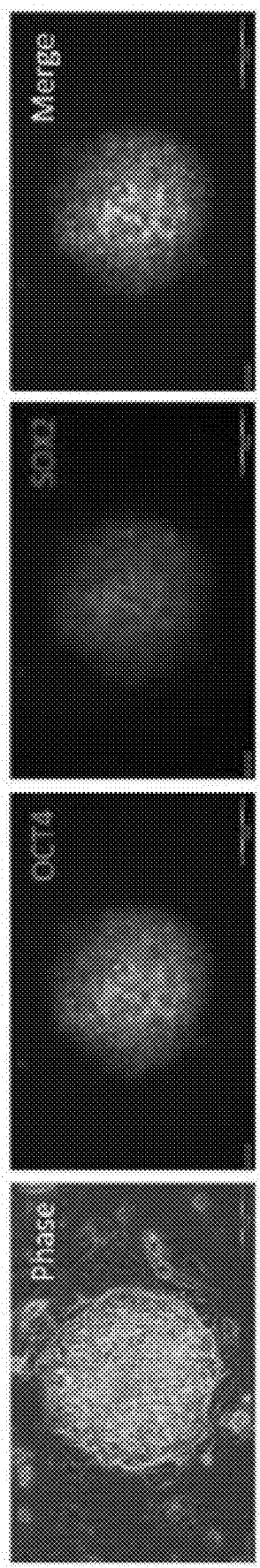
FIGS. 10A-10D show that EPSCs show spontaneous differentiation to trophoblasts during embryoid body differentiation. Oct4-H2B-Venus and SOX2-H2B-mCherrry double reporter EPSCs (FIG. 10A) were made into embryoid bodies (FIG. 10B). After 4 days of EB induction, we observed a significant double negative (Oct4/SOX2) population (FIG. 10C). FACS sorting and qPCR was performed which revealed that the double negative population had significant upregulation of trophoblast related genes including CDX2 and EOMES. No expression of brachyury (T) was detected.
Figure 10B:
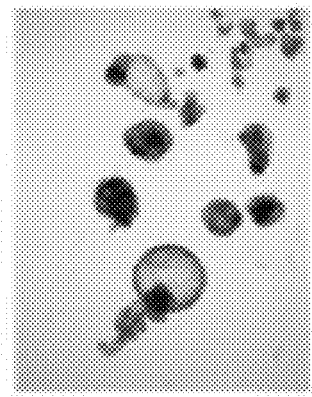
Figure 10C:
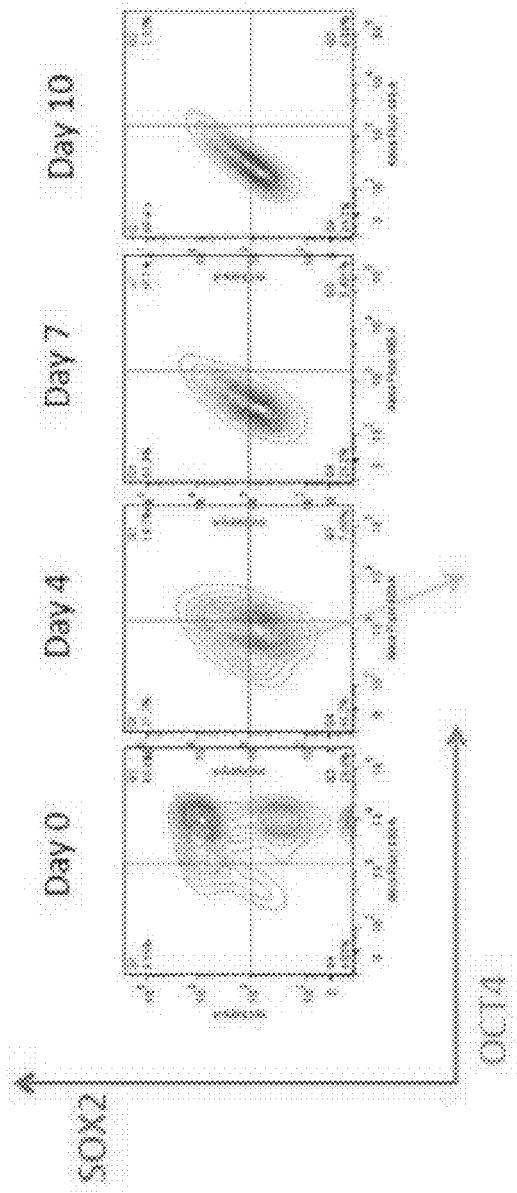
Figure 10D:
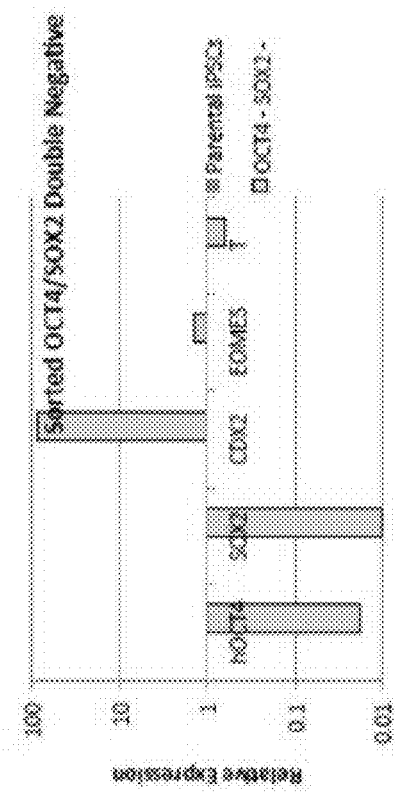
Figure 11:
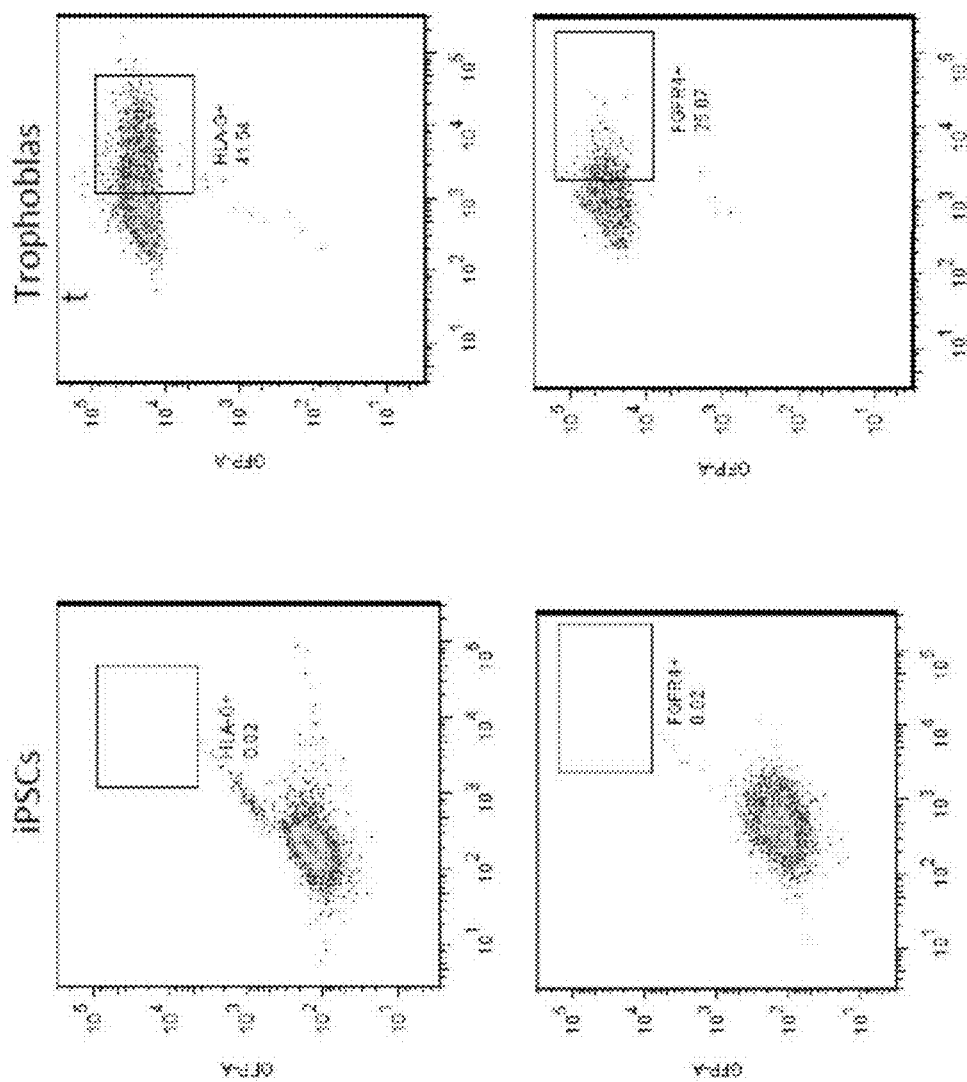
FIG. 11 shows that EPSCs can differentiate to hormone-secreting trophoblasts using a published human trophopblast induction protocol.

Compared to the standard human H1 ES cells, the converted H1 cells (H1-EPSCs) can rapidly (in two days of FGF4 culture) up regulate key trophoblast master regulators such as CDX2, EOMES and ELF5 (FIG. 9). Moreover, in embryoid bodies from EPSCs, cells expressing CDX2 and EOMES, but not genes for mesoderm or endoderm, are also detected (FIG. 10), indicating spontaneous differentiation to trophoblast during embryoid body differentiation.

The trophoblast induction protocol used for human EPSCs is the same as that described herein for mouse EPSCs.

Human EPSCs were also found to respond to current protocols for differentiating standard human ES cells to trophoblasts, described in (Amita M, et al 2013). EPSCs were differentiated to hormone secreting trophoblast following 9 days treatment with BMP4 10 ng/ml, 1ug A83-01 (ALK4/5/7 inhibitor), 0.1 uM PD173074 (FGFR1) and the differentiated cells express HLA-G and FGFR4.

Figure 12:
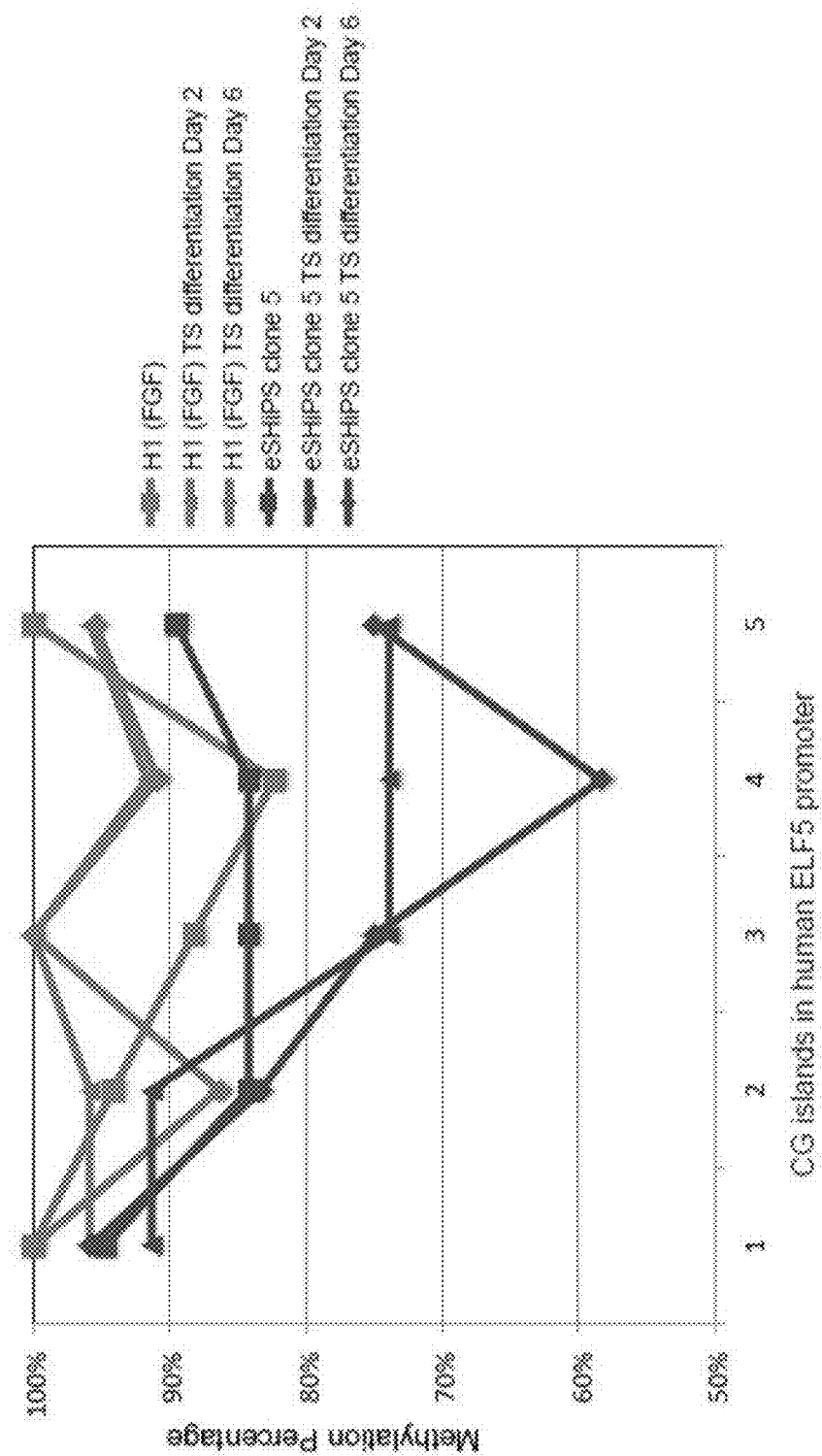
FIG. 12 shows that EPSCs undergo progressive ELF5 demethylation at the eLF5 locus during trophoblast differentiation. The bottom three lines in the graph correspond to the EPSC clones.

ELF5 is considered to the trophoblast lineage identity master regulator. It is believed that the ELF5 locus must be demethylated at the initiation of trophoblast development. We examined methylated Cytosine at the ELF5 promoter region. In standard human H1 ES cells, the ELF5 promoter region is methylated, and the methylation status is actually increased during trophoblast differentiation (FIG. 12). In contrast, EPSCs have slight lower DNA methylation at the ELF5 promoter. Importantly, during trophoblast differentiation, the ELF5 promoter is rapidly demethylated (FIG. 12), as expected for the bona fide trophoblast differentiation.

Figure 13:
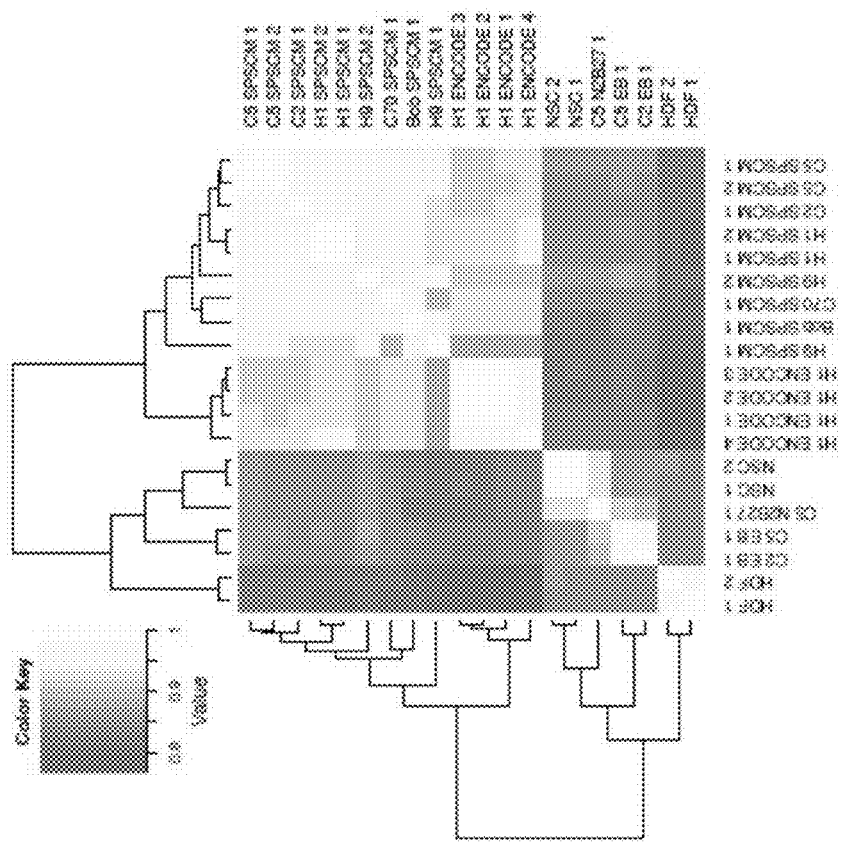
FIG. 13 shows a heatmap of correlation and hierarchical clustering of EPSC-ESs, EPSC-iPSCs, standard human ES cells, differentiated EPSCs and parental donor cells. NSC=neural stem cells, EB=embryoid body, HDF=human dermal fibroblasts. Correlations were measured by Spearman's correlation coefficient.
Figure 14:
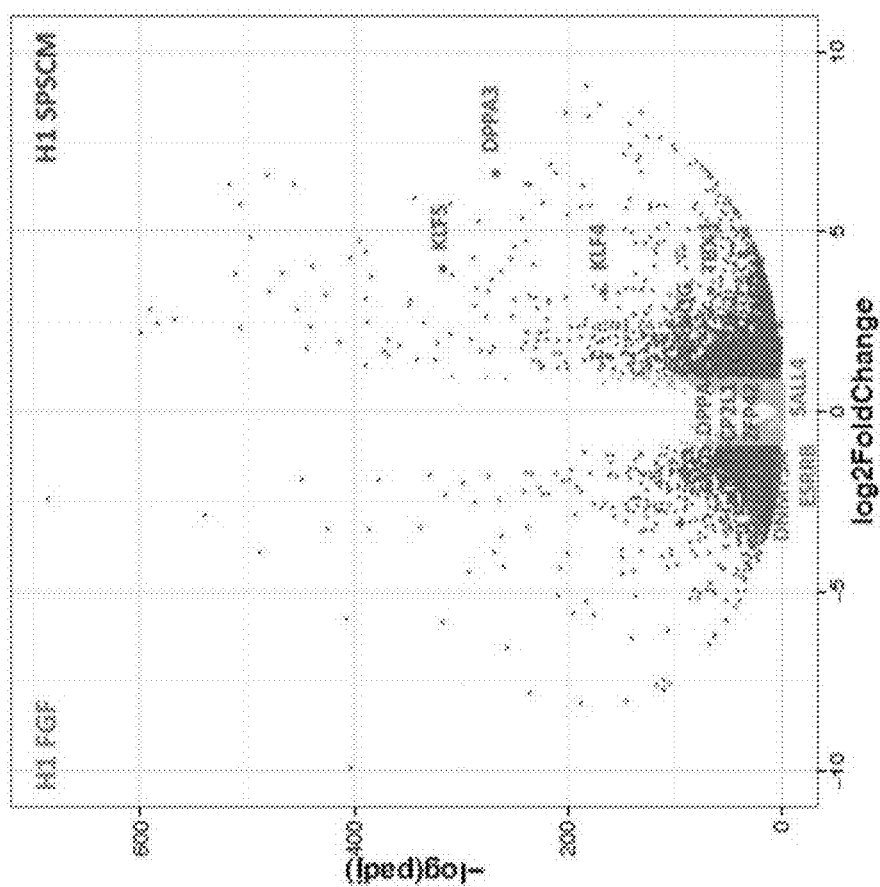
FIG. 14 shows differential expression analysis of converted H1-EPSCs compared to H1 embryonic stem cells.

To characterize EPSCs at the genome level, we performed RNA-seq on several EPSC lines and compared to standard human ES cells. Human ES cell data are from ENCODE H1 ES cells. EPSCs clearly have a distinct transcriptome from H1 human ES cells or other human cells including neural stem cells, differentiated EPSCs or dermal fibroblast cells (FIG. 13). RNAseq also revealed that EPSCs express significantly higher levels of key pluripotency genes, including NANOG, TBX3, DPPA3, and KLF4 (FIG. 14).

Gene ontology term enrichment analysis showed that EPSCs expressed higher levels of genes involved in stem cell maintenance and embryonic placenta development consistent with our in vitro trophoblast differentiation results.

Interestingly, many more genes highly expressed in EPSCs are enriched in early stages of preimplantation embryos, compared to standard human ES cells (FIG. 15).

Minimal Sets of Inhibitors for the Expanded Potential.

2i ('two inhibitors') contains Mek1 inhibitor (PD0325901) and GSK3.

Mouse EPSCs were initially derived and maintained in the standard EPSCM that contains six inhibitors (see materials and methods). To determine the effects of individual inhibitors in EPSCM and to explore the possibility that fewer inhibitors might be sufficient for the expanded potential in mouse stem cells, we cultured AB2.2 mouse ESCs in various combinations of inhibitors, initially based on the 2i/LIF medium, for at least 5 passages before injected to 8-cell host embryos. The chimera blastocysts were co-stained for mCherry and Cdx2 for TE contribution.

Adding an SFK inhibitor (A419259) or wnt inhibitor (XAV939) to the 2i/LIF (2i) medium substantially increased TE contribution whereas JNK and p38 inhibitors had moderate effects. Therefore in mouse EPSCM it appears that JNK and p38 inhibitors are not essential for the production of EPSCs. In human EPSC data, JNKi and p38i were still required as their absence caused gradual deterioration of the human EPSC culture.

The functions of the inhibitors on TE contribution were further confirmed by the removal of individual inhibitors from EPSCM. Surmising the blastocyst data revealed that some 3-inhibitor combinations: a Mek1 inhibitor, GSK3 inhibitor and SFK inhibitor (2i+A419259); Mek1 inhibitor, GSK3 inhibitor and wnt inhibitor (2i+XAV939) or GSK3 inhibitor, SFK inhibitor and wnt inhibitor (CHIR99021+ A419259+XAV939) were able to confer mouse ESCs with substantial expanded potential in this in vitro assay.

We injected ESCs cultured in KSR/2iA to generate chimera embryos and checked their contribution to embryo proper, placental trophoblast and yolk sac, respectively.

ESCs cultured in this medium still expressed high levels of pluripotency factors and low levels of lineage marker genes. Therefore, as few as two inhibitors could be sufficient for mouse ESCs to acquire the expanded developmental potential to the placenta trophoblasts and to the yolk sac endoderm.

EPSCs are Amenable to Genome Editing.

Since human EPSCs proliferated robustly and are easy to culture, we attempted to perform genome editing in these cells. We first targeted the SA-H2B-Venus cassette to the ubiquitously expressed ROSA26 locus using standard homologous recombination. The 47% targeting efficiency achieved is comparable to that in mouse ESCs. The CRISPR/Cas9 system has made genome editing much more efficient and simpler. Therefore, we made OCT4 and NANOG H2B-Venus or H2B-mCherry reporter human EPSC lines by using CRISPR/Cas9-facilitated targeting. The targeting efficiencies at these loci ranged from about 50% to 80%. The human OCT4-H2B-Venus reporter EPSCs provided a convenient way to test culture conditions. For example, adding a further inhibitor, NOTCH, to the six inhibitors already present in the EPSCM did not noticeably affect human EPSC cultures in terms of the percentage of OCT4-H2B-Venus+ cells.

In a separate experiment we also observed that human EPSCs can be produced in a medium containing fewer than six inhibitors, in this case only three inhibitors, if the EPSCM contains a chemically defined nutrient medium such as Albumax II. In this experiment three inhibitors, a Src Kinase family (SFK) inhibitor a GSK3 inhibitor and a Wnt inhibitor were added to Albumax medium. Human EPSCs were passaged successfully for at least 20 passages in this medium. We observed that the culture was stable and cells did not appear to be differentiated. These results mirror our observations for mouse EPSCs where we know that 3 inhibitors or even fewer can confer mouse cells the expanded potential. However, during converting standard human ES cells to EPSCs, we have found that the standard EPSCM is more stringent than the Albumax-based three inhibitor medium. Therefore, these two media (the six-inhibitor EPSCM and the three inhibitor Albumax-based EPSCM) may complement each other in different situations.

Materials and Methods

Culturing Mouse EPSCs, ESCs and iPSCs

Mouse ESCs were cultured in standard N2B27-2i/LIF, or in M15 media—Knockout DMEM (Invitrogen), 15% foetal bovine serum (FBS, Hyclone), 1× Glutamine-Penicillin-Streptomycin (GPS, Invitrogen), 1× non-essential amino acids (NEAA, Invitrogen), 0.1 mM β-mercaptoethanol (β-ME, Sigma) and $10^6$ U/ml hLIF (Millipore). Mouse EPSCs were cultured in EPSCM—DMEM/F12 (Invitrogen), 20% Knockout Serum Replacement (Invitrogen), 1× GPS, 1× NEAA, 0.1 mM β-ME and $10^6$ U/ml hLIF (Millipore) supplemented with the following small molecule inhibitors: CHIR99021 (Tocris, 3 μM), PD0325901 (Tocris, 1 μM), JNK Inhibitor VIII (Tocris, 4 μM), SB203580 (Tocris, 10 μM), A-419259 (Santa Cruz, 0.3 μM) and XAV939 (Stratech, 5.0 μM).

Mouse EPSCs were routinely cultured on mitomycin C-inactivated STO feeder cells and were passaged every 3-4 days at 1:3 ratio by a brief PBS wash followed by single-cell dissociation using Accutase (GIBCO).

RT-PCR

Total RNA was isolated using the RNeasy Mini Kit (Qiagen) for cultured cells or RNeasy Micro Kit (Qiagen) for sorted placenta cells. RNA were subsequently quantified and treated with gDNA WipeOut to remove genomic DNA. cDNA was prepared using the QuantiTect Reverse Transcription Kit (Qiagen). Taqman Gene Expression Assays (Life Technologies) and ABsolute Blue qPCR ROX Mix (ABgene) was used for probe-based qPCR assays. Primer pairs and SYBR Green ROX qPCR Mastermix (QIagen) were used to check the expression of trophoblast specific genes in sorted placenta cells. All qPCR reactions were performed on ABI 7900 HT Sequence Detection System (Life Technologies). Gene expression was determined relative to Gapdh using ΔCt method.

DMR (Differentially Methylated Regions) Analysis

Bisulfite treatment was performed using the EpiTect Bisulfite Kits (Qiagen) according to the manufacturer's recommendations. Genomic DNA PCR for promoter regions was performed and PCR products were cloned using pGEM-T Easy Vector Systems and sequenced from both ends.

Embryo Dissection, Placenta Dissociation and FACS Analysis

E14.5 embryos were dissected and imaged using Leica M205FA Automated Fluorescence Stereo Microscope. Placenta, yolk sac and embryo samples from mCherry$^+$ embryos were taken for genotyping. Dissected placentas were cut into fragments of around 1 mm diameter on ice and digested with 2.35 ml placenta digestion solution (5% FBS, 10 mM HEPES, 100 μl Enzyme D, 50 μl Enzyme R and 12.5 μl Enzyme A in HBSS according to the instruction of Lamina Propria Dissociation Kit) for 30 min at 37° C. with shaking. After digestion, the placentas were dissociated into single cells by pipetting vigorously and filtering through 70 μm cell strainer (BD Bioscience). Single cells from placenta were treated with ACK Lysing Buffer (BioWhittaker) to remove the red blood cells and resuspended in FACS buffer (BD Pharmingen) for FACS analysis or sorting. E14.5 fetal livers and fetal brains were dissociated in HBSS by pipetting vigorously and filtering through 70 μm cell strainer. All FACS analysis was performed on BD LSRFortessa Cell Analyzer (BD Biosciences). Placenta cells were sorted on MoFlo™ XDP (Beckman Coulter).

DNA Genotyping

Genomic DNA was extracted from placenta, yolk sac and embryo samples from mCherry$^+$ embryos, quantified and diluted to 10 ng/ml. DR10-EPSCs have a Cre cassette at the Rosa26 locus. A pre-designed TaqMan® Copy Number Assay was used to determine the contribution of DR10-EPSCs. AB2.2-EPSCs or ESCs have a non-functional Neo cassette at the Hprt locus. A custom-designed TaqMan® Copy Number Assay was used to determine the contribution of these cells. Genomic DNA from parental DR10-EPSCs or AB2.2 ESCs was used as the positive controls, and DNA from a wild type embryo was used as the negative control. Cre/Neo copy number was first normalized to Tert using ΔCt method (TaqMan® Copy Number Reference Assay, Life Technologies). The contribution of DR10/AB2.2 in individual placenta, embryo proper, and yolk sac sample was then determined by normalizing them to parental DR10/AB2.2 cells.

Teratoma Formation

Mouse EPSCs were suspended in EPSCM, and $5\times10^6$ cells were injected subcutaneously into both dorsal flanks of NSG mice (NOD.Cg-Prkdcscid Il2rgtm1Wjl/SzJ. The Jackson Laboratory). Four weeks after injection, teratomas were dissected, fixed overnight in 10% buffered formalin phosphate and embedded in paraffin before sectioning.

Preparing the Embryos and Foster Recipients

For the production of 8-cell stage embryos, over 8-weeks-old CD1 females were super ovulated by intraperitioneal injection of Pregnant Mare Serum Gonadotropin (PMSG, 7.5 IU each) (Intervet, PMSG-Intervet) followed 46-48 hours later by injection of human Chorionic Gonadotropin (hCG 7.5 IU each) (Intervet, Chorulon) and set up with proved studs. Vaginal plugs were checked the following morning (0.5 day post coitum, dpc), and 8-cell stage embryos were collected at 2.5 dpc and cultured in 1.0 ml KSOM (Millipore) medium containing 3.0 mg/ml BSA (Sigma) in incubator in humidified atmospheres of 5% $CO_2$ at 37° C. CD1 females were mated with vasectomized C57BL6/JCBA F1 males and used as recipients for embryos transfer at 2.5 dpc.

Injection of ESCs and EPSCs

Injections were carried out with a Nikon Eclipse TE2000-U inverted microscope unit. ESC/EPSC microinjection was performed at room temperature on the inverted lid of a 100-mm falcon culture dish in an injection drop of 1.0 ml M2 medium (Sigma). The embryo was injected with 6-8 cells per 8-cell stage embryo for bulk injection or 1 cell per embryo for single cell injection. After 45-50 embryos have been injected, the injected embryos were washed three times in KSOM (Millipore) containing 3.0 mg/ml BSA. Embryos were then transferred into a well of four-well plate containing 1.0 ml KSOM. After overnight culture, 20-25 injected embryos were transferred into both uterus of a foster recipient.

Separation of Blastomeres 8-cell stage embryos were collected from oviducts of plugged super ovulated females mated by stud males at 1.5 or 2.5 dpc. Before separating the blastomere, the embryos were cultured in 1.0 ml KSOM containing 3.0 mg/ml BSA and 5.0 µg/ml CB (Sigma, C6762) for at least half an hour. Embryos were suspended in a 100.0 µl Tyrode's Solution drop for about 15-20 seconds, and then the embryos were transferred into a new 100.0 µl Tyrode's Solution drop until zona pellucida disappeared. The embryos were transferred into a fresh 100.0 µl M2 drop immediately after zona pellucida disappeared. The embryos were washed a few times in M2 drops. The embryos were sucked and blown a few times by a blunt needle (inner diameter: 40 µm). Individual blastomeres were collected for seeding to 96-well plates.

Kinase Inhibition and Western Blot $1.0 \times 10^6$ ESCs were seeded into gelatinized wells of a 6-well plate in one of the media: M15, N2B27-2i/LIF, KSR-2i/LIF or EPSCM, respectively. After 48 hours, whole cell protein was extracted from harvested cells, and quantified using BCA assay (Thermo Scientific). Total protein (40 µg) was fractioned on 4-12% Bis-Tris Novex gel (Invitrogen) and electroblotted onto PVDF membranes, and probed with the following antibodies: pERK, ERK, pSRC, SRC, pp38, p38, pJNK, JNK and AXIN1 (all from Cell Signalling). α-Tubulin (Abcam) was used as loading control. Blots were incubated with horseradish peroxidase-coupled anti-rabbit or anti-mouse IgG and developed with ECL Prime (Amersham).

LIF Response in ESCs and EPSCs

For LIF stimulation, $1.0 \times 10^6$ cells were seeded in SPSCM for 24 hours. Cells were washed with PBS and cultured in DMEM/F12/KSR for 4 hours, then LIF was supplemented at concentration of 0.0, 0.5, 1.0, 5.0 and 10.0 ng/ml for 30 minutes. Whole cell protein was extracted for Western blot using pSTAT3 (Cell signalling) and STAT3 (BD Biosciences) antibodies. α-Tubulin (Abcam) was used as loading control.

To analyse the expression of down-stream target genes of Jak-Stat3 and MAPK signalling at transcription level after LIF stimulation, both E14Tg2a ESCs and EPSCs were deprived of LIF for 4 hours as above, LIF 1.0 ng/ml was supplemented for 1 hour, total RNA was extracted and reverse transcribed to make cDNA. qPCR was performed using Taqman Gene Expression Assays (ABI)

Wnt Signalling Detection

To investigate Wnt signalling in EPSCs, $1 \times 10^6$ cells were seeded in M15, N2B27-2i/LIF, KSR-2i/LIF and EPSCM for 48 hours, cytoplasmic and nuclear protein were extracted with a NE-PER nuclear and cytoplasmic extraction kit (Thermo Scientific) for Western blot to detect pβ-catenin (Cell Signalling), β-catenin (Sigma) and active-β-catenin (Millipore). α-Tubulin (Abcam) and H3 were used as loading control for cytoplasmic and nuclear protein respectively.

For TOPflash assay, $4 \times 10^6$ cells were co-transfeted with TOPflash and pRL-TK by Nucleofection (Amaxa). Cells were split 1:9 into a 24 well plate for 24 hours in M15, N2B272i/LIF and SPSCM for 48 hours, cell lysate was prepared for luciferase assay.

Progression of Preimplantation Embryos and Single Blastomeres in EPSCM 2C-4C stage embryos were cultured in KSOM for about 12 hours when most of them reached 8C stage under microscope. Each 8C stage embryo was transferred to one well of a 96-well STO feeder plate or gelatinized plate. Embryos were cultured in M15 or EPSCM for 8 days until some embryos hatched and formed outgrowth.

Immunostaining of early embryos was performed according to the published protocol by Dr. Jenny Nichols (U. Cambridge) with slight modification. Briefly, embryos were washed in PBS/PVP, fixed in 2.5% PFA for 15 minutes at room temperature; permeabilised in PBS/PVP/0.025% TritonX-100 for 30 minutes; blocked in PBS/PVP/0.1% BSA/0.01% Tween-20/2% Donkey serum for 1 hour at room temperature; then incubated with primary antibodies in blocking solution at 4° C. overnight; washed with blocking solution 3 times for 15 minutes each; incubated with Alexflour secondary antibodies 1 hour at room temperature; washed with blocking solution 3 times for 15 minutes each; mounted the embryos in a small drop of vectorshield with DAPI; covered with a coverslip and sealed with nail varnish. For the embryo outgrowth, cells in 96 well were fixed in 4% PFA. Blocking solution is PBS/0.1% Triton X-100/1% BAS/3% Donkey serum, the staining procedure is similar to as listed above. After secondary antibody incubation, cell nuclei were stained with DAPI and observed under fluorescence microscope. The primary antibodies used are Cdx2; Oct4(Abcam), Oct4 (Santa Cruz), Cleaved Caspase 3 (Cell Signalling), Ki-67 (Cell signalling).

For blastomere progression, 8C embryos were dissociated into single blastomeres and plated into one 96 well each on STO feeder in M15, N2B27-2i/LIF or EPSCM. The growth of blastomeres was monitored under microscope every day until day 12. The wells with outgrowth were fixed and immunostained with Cdx2 and Oct4 antibodies as mentioned above.

Placental Tissue Section Immunostaining

Paraffin embedded E14.5 placenta sections were deparaffined in Xylene, 100%, 95%, 80%, 70% and 50% ethanol for 3 minutes each, rinsed with running cold water. Antigens were retrieved in sodium citrate buffer (10 mM Sodium Citrate, 0.05% Tween-20 pH 6.0) with microwave for 15 minutes, rinsed with running cold water. The slides were then washed in PBS/0.025% Triton X-100 (PBST) 2 times, 5 minutes each, blocked in PBST/1% BSA/5% Donkey serum for 1 hour at room temperature, briefly rinse with PBST, incubated with anti-mCherry antibody (Abcam) at 4 overnight. Finally, the slides were wash with PBST 3 times, 5 minutes each and blocked for at least 15 minutes, and wash with PBST 3 times and 5 minutes each. The sections were mounted in a small drop of DAPI (Vector Shield), and covered with coverslip and sealed with nail varnish.

Reprogramming MEFs

To reprogram MEFs, episomal vectors with Oct4, c-myc, Klf4 and Sox2 (OCKS 4F, 5 μg), and Rarg, Lrh1 (RL 2F, 5.0 μg) were first mixed with $1.0 \times 10^6$ cells in OptiMEM (Invitrogen), and the cells were electroporated with Amaxa Nucleofector (Lonza, Germany). After electroporation, the cells were plated onto 10 cm dishes with STO feeder in M15 for recovery for 24 hours, medium was changed every two days, at day 7, colonies emerged at 14, medium was switched to EPSCM for another 6 days, colonies were picked into 24 well on STO feeder in EPSCM for expansion and characterization.

Chromatin Immunoprecipitation

All cells cultured in 10-cm plates were cross-linked for 12 min by 1% formaldehyde and the crosslinking was quenched by 2.5 M glycine (0.125 M final concentration). Crosslinked cells were spun at 600×g for 5 min, nuclei were prepared by consecutive washes with P1 buffer (10 mM Tris pH 8.0, 10 mM EDTA [pH 8.0], 0.5 mM EDTA, 0.25% Triton X-100) followed by P2 buffer (10 mM Tris pH 8.0, 1 mM, EDTA, 0.5 mM EGTA, 200 mM NaCl). Pellets were resuspended in 2 ml of ChIP lysis buffer (50 mM HEPES/KOH, pH=7.5, 300 mM NaCl, 1 mM EDTA, 1% Triton X-100, 0.1% DOC, 0.1% SDS, and protease inhibitors complete mini (Roche) and sonicated using BioRuptor (Diagenode) (pulsed with 15 cycles of 30 seconds sonication and 30 seconds rest). DNA was sheared to the size range between 500 and 1000 bp (confirmed on agarose gel). IgG (Cell Signalling, 2729S) and antibodies for H3K27me3 (Millipore 07-449), H3K4me3 (Active Motif, 39159) were used in ChIP.

Single-Cell RNA-Seq Library Preparation

The preparation is previously described by Brennecke et al (Brennecke et al., 2013). In brief, five thousands trypsin-dissociated mouse EPSC (DR10) are loaded onto the 10-17-μm C1 Single-Cell Auto Prep IFCs (Fluidigm) and cell capture was performed according to the manufacturer's protocol. Individual capture site was inspected under light microscope to confirm the presence of single cell. The locations of empty capture sites and sites containing multiple cells or burst cells were noted for downstream quality control during data analysis. The lysis and reverse transcription mixes were then prepared with the SMARTer PCR cDNA Synthesis kit (Clontech) and the Advantage 2 PCR kit (Clontech) according to Fluidigm recommendations. 1.0 μl of the ERCC Spike-In Control Mix (Ambion) in a 1:400 dilution was added to the lysis mix to allow control of technical variation of the library preparation protocol. Lysis and cDNA reverse transcription and PCR were performed and cDNA harvested by the C1 Single-Cell Auto Prep system according to manufacturer's settings. The success of cDNA preparation was confirmed by optimal DNA signal detected by a 2100 Bioanalyzer with high-sensitivity DNA chip (Agilent). Multiplex sequencing libraries were prepared using the Nextera XT DNA Sample Preparation Kit and the Nextera Index Kit (Illumina) according to the recommendation in the C1 Single-Cell Auto Prep manual. The libraries of individual cells were then pooled and sequenced on 4 lanes of HiSeq 2500 (Illumina) to generate 100 bp paired-end reads through the Sanger Institute in-house sequencing pipeline.

Reads Alignment and Quality Control of Dataset

Pair-end reads from both bulk and single-cell RNA-seq datasets were aligned to the *Mus musculus* genome (GRCm38.74) by STAR (version STAR_2.3.0e_r291) with specific additional parameter settings: '--outFilterMultimapScoreRange 1--outSAMstrandField intronMotif' (Dobin et al., 2013). The quantification of gene expression was performed by the htseq-count module from the HTSeq package www.huber.embl.de/users/anders/HTSeq/) with gene annotation from GTF files (GRCm38.74) with parameter "-s no" in union mode (Anders, Pyl, & Huber, 2014). The count matrix of individual cells were normalized by size factors with DESeq2 (M. Love, Anders, & Huber, 2014). As quality control in the single-cell dataset, cells with less than 500,000 counts in annotated features, expression of less than 4000 genes or high percentage (>10%) of counts mapping to mitochondria-encoded genes were removed from subsequent analysis.

Chromatin Profile Analysis

The H3K4me3, H3K27me3 and input ChIP library of EPSC lines DR25 and DR10 were prepared by the Sanger core DNA pipeline and sequenced on 2 lanes of HiSeq2500 in multiplex. The paired-end 75 bp reads were mapped to the mouse reference genome GRCm38 by Burrows-Wheeler Aligner (Li & Durbin, 2009) (bwa-0.5.10). The library of DR25 and DR10 were then merged to construct the EPSCM dataset for subsequent analysis by samtools (Li et al., 2009). H3K4me3 and H3K27me3 enriched peaks were detected by MACS (version 2.1.0) with the flag "--broad" turned on for detection of broad histone modification peaks. After filtering, 2,518,486 and 1,748,849 tags were kept for H3K27me3 and H3K4me3 peak calling. The signal track was generated by MACS (version 1.4.2) (Zhang et al., 2008) with redundancy rate set to 1 and input DNA as the control, other parameters were set according to recommendations for histone modifications from Feng et al (Feng, Liu, & Zhang, 2011 *Current Protocols in Bioinformatics,* 1-14) and visualized by the UCSC genome browser. The H3K4me3 and H3K27me3 ChIP-seq data of E14 mouse ES cells cultured in 2i/LIF and TNGA gnomic DNA control was downloaded from the NCBI GEO SuperSeries GSE23943. The BED files were then lifted over to the mm10 genome by the UCSC LiftOver web tool and shuffled and randomly sampled to U.S. Pat. Nos. 2,518,486 and 1,748,849 reads for H3K27me3 and H3K4me3 peak calling with the same parameters by MACS as described (version 2.1.0). Genes were classified as associated with H3K4me3/H3K27me3 if peaks were present in the window from 3 kb upstream of TSS to 3 kb downstream of TES. TSS and TES coordinates were obtained from Ensembl Biomart as gene start and stop sites and the +/−3 kb regions were intersected with the peak regions by Bedtools2 (version 2.19.1) (Quinlan & Hall, 2010 *Bioinformatics,* 26, 841-842). Bivalent genes were defined as genes that were both H3K4me3 and H3K27me3-associated similar to Gafni et al (Gafni et al., 2013). Comparison of H3K4me3 signals at the promoter (TSS+/−3 kb) of placental development genes were performed by ngs.plot (version 2.41.3) (Shen, Shao, Liu, & Nestler, 2014). Only the first reads of the EPSCM dataset were used for plotting after removing duplicated reads by samtools (version 0.1.18) (Li et al., 2009).

Differential Gene Expression Analysis

For the comparison of the transcriptomes of mouse EPSCs and 2i/LIF ESCs, differential expression analysis was performed with DESeq2 (M. I. Love, Huber, & Anders, 2014). Cooks distance testing was turned off to accommodate the noisy expression nature in single-cell data and counts from the ERCC spikes in the EPSCM datasets were removed from the input matrix. Differential expression with adjusted p-value <0.05 and |log 2 fold change|>1 were considered as significantly differentially expressed. Cell lines and passage numbers: DR25 and DR10, in serum, passage 5; in 2i/LIF, passage 5; in EPSCM, passage 15. DR9 and DR4, in 2i/LIF, passage 4 and in EPSCM, passage 5. AB2.2 ESCs, M15 passage 18, 2i/LIF passage 6, EPSCM passage 7. E14 ESCs, M15 passage 20, 2i/LIF passage 5, EPSCM passage 6.

Gene Ontology Enrichment Analysis

Gene ontology term enrichment analysis was performed by DAVID (Huang, Sherman, & Lempicki, 2009) (david.abcc.ncifcrf.gov/). Gene symbols were used as input gene list and the mouse genome was chosen as background.

Embryonic Stage-Enriched Gene Set Enrichment Analysis

Gene set enrichment analysis was performed with the javaGSEA application (version 2.1.0) available online (www.broadinstitute.org/gsea/downloads.jsp) with "weighted" enrichment statistics setting (Subramanian et al., 2005). The mouse pre-implantation embryonic stage-enriched gene sets were compiled by analysing the published expression count matrix from Deng et al (Deng et al., 2014). The top 500 genes that showed higher average expression than other stages after size factor normalization by DESeq2 were considered stage-enriched and used as testing gene set. The normalized count matrices of the EPSC and standard 2i/LIF ESC single-cell dataset were used as input expression dataset. Enrichment is considered significant if FDR is below 0.1 and nominal P value is below 0.05.

Estimating the Pre-Implantation Embryonic Developmental Time Frame of EPSCs

The whole transcriptome or the normalized count values of the 36 epigenetic modifiers defined by Burton et al (Burton et al., 2013 Cell Reports, 5(3), 687-701) were used to estimate the pre-implantation embryonic developmental time point of EPSCs. The expression of the selected epigenetic modifiers has been previously shown to provide superior segregation of blastomeres of different pre-implantation embryonic stages to pluripotency-associated transcription factors by single-cell qPCR (Burton et al., 2013). The normalized count matrix of the whole transcriptome or the epigenetic modifiers from the dataset of Deng et al were transformed by log 2(nCount+1) to stabilize the variance of the data and principal component analysis were performed by the prcomp( ) function in R on the transformed matrix. The scores were then used to predict the scores of EPSCs or 2i/LIF ES cells by the predict ( ) function in R.

Comparison of EPSCs, Hhex-Venus$^+$ ES Cells, MERV-TdTomato$^+$ ES Cells and In Vivo iPS Cells The raw RNA-seq data of in vivo reprogrammed iPS cells (iviPS1-6) from Abad et al, Hhex-Venus$^+$ ES cells from Morgani et al (both 2i/LIF and serum/LIF) and MERV-Tdtomato$^+$ reporter ES cells from MacFarlane et al were downloaded from GSE48364, GSE45182 and GSE33923, respectively, and aligned to GRCm38 mouse genome by STAR. Gene expression was the quantified as described above by HTSeq-count. To normalize the difference between studies and sequencing platforms, the gene expression profile of EPSCs (DR9, DR25, DR4, DR10-EPSCM), MERV-TdTomato+ ES cells and in vivo iPS cells (1-6) were quantified as the relative log 2 fold change of expression of the genes compared to 2i/LIF ES cells (DR9, DR25, DR4, DR10-2i/LIF) by DESeq2. For Hhex-Venus$^+$ ES cells, the unsorted 2i/LIF datasets (GSM1098629 and GSM1098630) were used for normalization. Genes with unavailable log 2 fold change value in DESeq2 were removed from comparison. Sequences of repeat elements (mouse and shared) were downloaded from (www.girinst.org/repbase/index.html). A custom GTF file and genome index was constructed by STAR with individual repeat class treated as individual chromosome. Reads were then realigned to the new index. Expression was quantified by HTSeq-count as described above and normalized by size factors computed by DESeq2. The relative expression of EPSCs and MERV-TdT$^+$ ES cells were then calculated relative to that of MERV-TdT$^-$ ES cell.

Protocol for EPSC Expansion, Passaging and Feeder Removal.

EPSC Expansion

Expand H-EPSCs on STO feeder plates (expressing LIF transgene)

Passaging and Feeder Removal

Aspirate media from plate and wash once with DPBS (Invitrogen, 14190)

Aspirate DPBS and add Accutase (Millipore, SCR005) to cover base of well

Place plate in incubator (37 degrees) for 5 mins

Remove plate from incubator and using P1000 assist cell detachment

Add equal volume of EPSCM (+ROCK inhibitor) to plate (ROCK inhibitor is only added during the first 24 hours to enhance the single cell survival and plating of EPSCs)

Collect the total volume and pass through a 100 μm filter into 15 ml falcon tube Centrifuge @1200 rpm for 3 minutes Aspirate supernatant and resuspend in 1 ml of EPSCM (+ROCKi)

Transfer cells to a non-gelatinized 10 cm plate containing EPSCM (+ROCKi) and place in incubator for 30 minutes.

Collect the supernatant from the plate and count the cells using trypan blue exclusion.

Neural induction from human expanded potential stem cells-protocol (following on from the EPSC Expansion and passaging and feeder removal protocol above).

Neural Induction

Aspirate supernatant and resuspend cells in Neural Induction media (+ROCKi)

Cells are differentiated on 6 well plate(s) at a cell density of 2.5-5×10$^4$ cells/cm2

Prior to cell plating, coat well with ECM gel, aspirate and discard

Plate desired cell number in Neural Induction media (+ROCKi)

During differentiation, change media after the first 24 hours, then, every 48 hours thereafter Neural rosettes will become apparent after 2.5-3 weeks of differentiation At the rosette stage, to establish NSC line, first coat new plate with ECM gel, aspirate and discard. Neural induction culture is passaged enzymatically using Accutase and split 1:1 or 1:2 in NSC-CM.

During expansion, change media every 48 hours

Cells are routinely expanded on 6 well plate(s) in NSC-CM at cell density of 0.5-5×10$^4$ cells/cm2

Neuronal Differentiation

Coat 35 mm dish with laminin (Sigma, L6274-0.5MG prepared to a working concentration 1-2 ug/cm$^2$). Place in incubator for 2 hrs prior to cell plating.

Day 0: Plate 5×10$^4$ cells/cm2 in NSC-CM

Day 1: Aspirate media, wash with PBS

Add NDM

Change media every 48 hours

Neural Induction Media

NDIFF 227 (Stem Cell Sciences, SCS-SF-NB-02)

10 ng/ml FGF-BASIC. Life Technologies Ltd. (Invitrogen), PHG0021

1 μM Dorsomorphin (Sigma, P5499-5MG)

Neural Stem Cell Culture Media (NSC-CM)
  NDIFF 227 (Stem Cell Sciences, SCS-SF-NB-02)
  10 ng/ml FGF-BASIC. Life Technologies Ltd. (Invitrogen), PHG0021
  10 ng/ml Epidermal Growth Factors (EGF). Life Technologies Ltd. (Invitrogen), PHG0311
Neuronal Differentiation Media (NDM)
  NDIFF 227 (Stem Cell Sciences, SCS-SF-NB-02)
  Prepare Extracellular matrix (ECM) gel from Engelbreth-Holm-Swarm murine sarcoma (Sigma, E1270-10ML) to working concentration by adding 1 ml ECM to 9ML KO-DMEM.
Primordial Germ Cell Induction from Human Expanded Potential Stem Cells-Protocol. (Modified from Duggal et al (2013)
(following on from the EPSC Expansion and passaging and feeder removal protocol above)
PGC Induction
  Aspirate supernatant and resuspend cells in PGCM (+ROCK inhibitor) Transfer cells to ultra-low attachment 6 well plate (1-1.5×10$^6$ cells/well). Change media every 48 hours (ROCKi is only required for the first 24-48 hrs). Allow EBs to form for 7-10 days then transfer to a gelatinized 6 well plate. Once EBs have attached to gelatin continue to culture for another 7-10 days.
Monitoring PGC Induction
  PGC Induction was assessed by serial FACS analysis. Successful differentiation was determined based on the emergence of a KIT+SSEA1+TRA1-81+ positive population. PGC transcription factors Oct4, Stella, PRDM1 (Blimp1), VASA and DAZL expression were checked using Taqman qPCR probes.
EPSCM Comprising a Ras-ERK Inhibitor, an SFK Inhibitor, a GSK3 Inhibitor, a JNK Inhibitor and a Wnt Inhibitor is Shown to Maintain Human EPSCs and Also Maintains Porcine iPSCs without Leaky Expression of Exogenous Factors.

In these examples, the EPSCM comprises a Ras-ERK inhibitor which is a Braf inhibitor. As shown in FIG. 16, the EPSCM maintains porcine iPSCs (piPSCs) without leaky expression of exogenous factors. Pig fibroblast cells were transfected with vectors expressing eight transcription factors: Oct4, Sox2, Klf4, c-Myc, Nanog, RARG, LRH1, LIN28. The factor cDNAs were cloned in the piggyBac transposon for PB mediated integration in to the genome. Expression of the reprogramming factors is inducible by adding Dox in the medium. Primary iPS colonies are then cultured in FGF2-containing medium before switching to the new medium.

Stable pig iPSC lines have been established in the new medium that express robust levels of endogenous key pluripotency genes and minimal levels of lineage marker genes. Importantly, these cells do not have detectable levels of exogenous factors. This is the first time that anyone has established such cells.

FIG. 17 shows that the EPSCM maintains human homogeneous human EPSCs.
Methods—EPSCM Composition
  In the above human and porcine experiments, the EPSCM included:
DMEM/F-12 (Gibco, 21331-020) medium supplemented with N2 (Gibco), B27 (Gibco),
human Activin (20 ng/ml; Peprotech),
LIF (1000 U/ml),
CHIRON99021 (0.2 µM; Stemgent), (GSK inhibitor)
Vitamin C (50 µg/ml, Sigma),
SB 590885 (0.2 nM, Tocris Bioscience), (Braf inhibitor)
Wh-4 (0.5 µM, Tocris Bioscience. (Inhibitor for Src).
XAV939 (5 µM), (wnt inhibitor)
SP600125 (0.8 nM, JNK inhibitor).
  Optionally, Activin 1.0 ng-100 ng/ml, 0.5% FBS for optimal cell proliferation.

REFERENCES

Yu et al (2012). Cell. Volume 150, Issue 4, p780-791
M. Abad et al. Nature Volume: 502, Pages 340-345 (Sep. 11, 2013).
T. Ishiuchi, M. E. Torres-Padilla, Curr Opin Genet Dev 23, 512 (October, 2013).
M. Zernicka-Goetz. Nat Rev Mol Cell Biol 6, 919 (December, 2005).
R. L. Gardner. Philos Trans R Soc Lond B Biol Sci 312, 163 (Dec. 17, 1985).
J. Rossant, P. P. Tam. Development 136, 701 (March, 2009).
H. Marks et al. Cell 149, 590 (Apr. 27, 2012).
Y. Yamanaka, et al. Dev Dyn 235, 2301 (September, 2006).
T. S. Macfarlan et al. Nature 487, 57 (Jul. 5, 2012).
S. M. Morgani et al. Cell Rep 3, 1945 (Jun. 27, 2013).
T. S. Macfarlan et al. Nature 487, 57 (Jul. 5, 2012).
S. M. Morgani et al. Cell Rep 3, 1945 (Jun. 27, 2013).
J. Wray, et al. Biochem Soc Trans 38, 1027 (August, 2010).
Q. L. Ying et al. Nature 453, 519 (May 22, 2008).
Thomson, J. A et al (1998). Science 282, 1145-1147.
Chung et al. Cell Stem Cell (2008), Volume 2, Issue 2, p 113-117
Nichols, J and Smith, A. (2009) Cell Stem Cell. Volume 4, Issue 6, p487-492.
Theunissen, T. W. et al. (2014). Cell Stem Cell. Volume 15, issue 4, p471-487,
Takashima et al. (2014) Cell. 11; 158(6):1254-69.
Wang W, et al. PNAS. (2011) 108; 45; 18283-8
Huang et al. (2009) Nature 461:614-620
Roberts R M, et al. Reproduction. 2014 Apr. 10; 147(5):D1-12.
Cho C H, et al. Diabetologia. 2012 December; 55(12):3284-95.
Duggal G et al. Stem Cells Dev. 2013 Dec. 1; 22(23):3141-55.
Abad M, et al. Nature. 2013 Oct. 17; 502(7471):340-5
Amita M, et al. Proc Natl Acad Sci USA. 2013 Mar. 26; 110(13):E1212-21
Chen B, et al. Nat Chem Biol. 2009 February; 5(2):100-
Themeli M, et al. Nat Biotechnol. 2013 October; 31(10): 928-33.
L. Azzolin et al. Cell 158, 157 (Jul. 3, 2014).
B. W. Doble, J. R. Woodgett. J Cell Sci 116, 1175 (Apr. 1, 2003).
M. Hemberger, et al. Hum Mol Genet 19, 2456 (Jun. 15, 2010).
R. K. Ng et al., Nat Cell Biol 10, 1280 (November, 2008).
L. Chen, et al, Cell Res 20, 982 (September, 2010).
P. J. Tesar et al., Nature 448, 196 (Jul. 12, 2007).

The invention claimed is:
1. A method for producing a population of expanded potential stem cells (EPSCs) which comprises:
  (i) providing a population of pluripotent cells; and
  (ii) culturing the population in an expanded potential stem cell medium (EPSCM), wherein the EPSCM comprises a basal medium supplemented with inhibitors consisting of an Src Kinases family (SFK) inhibitor, a GSK3 inhibitor and a tankyrase inhibitor, thereby producing a population of EPSCs.

2. The method according to claim 1, wherein the EPSCM further comprises LIF and/or IGF-II.

3. The method according to claim 1, wherein step (ii) comprises, culturing the population in the EPSCM for three to five passages thereby producing a population of EPSCs.

4. The method according to claim 1, wherein the method further comprises (iii) culturing the EPSCs in an EPSC maintenance medium comprising one or more of a Ras-ERK inhibitor, a Src Kinase family (SFK) inhibitor, a GSK3 inhibitor and a tankyrase inhibitor.

5. The method according to claim 1, wherein the method further comprises (iii) culturing the EPSCs in an EPSC maintenance medium and wherein the EPSC maintenance medium consists of a Src Kinase family (SFK) inhibitor, a GSK3 inhibitor and a tankyrase inhibitor.

6. The method according to claim 1, wherein the pluripotent cells are ESCs or iPS cells.

7. The method according to claim 1 wherein the cells are human or porcine.

\* \* \* \* \*

UNITED STATES PATENT AND TRADEMARK OFFICE
CERTIFICATE OF CORRECTION

PATENT NO. : 10,745,670 B2  
APPLICATION NO. : 15/527269  
DATED : August 18, 2020  
INVENTOR(S) : Pentao Liu et al.

Page 1 of 1

It is certified that error appears in the above-identified patent and that said Letters Patent is hereby corrected as shown below:

On the Title Page

Item (72) Inventors: Line 7:
"Pentao Liu" should be "Pengtao Liu"

Signed and Sealed this
Twentieth Day of February, 2024

Katherine Kelly Vidal
*Director of the United States Patent and Trademark Office*